(12) United States Patent
Assens et al.

(10) Patent No.: US 7,148,240 B2
(45) Date of Patent: Dec. 12, 2006

(54) AMINOALKOXYBENZOYL-BENZOFURAN OR BENZOTHIOPHENE DERIVATIVES, METHOD FOR PREPARING SAME AND COMPOSITIONS CONTAINING SAME

(75) Inventors: Jean-Louis Assens, Grabels (FR); Claude Bernhart, Saint Gely du Fesc (FR); Frédérique Cabanel-Haudricourt, Pignan (FR); Dino Nisato, Saint Georges d'Orques (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/362,138

(22) PCT Filed: Aug. 23, 2001

(86) PCT No.: PCT/FR01/02657

§ 371 (c)(1),
(2), (4) Date: Feb. 20, 2003

(87) PCT Pub. No.: WO02/16340

PCT Pub. Date: Feb. 28, 2002

(65) Prior Publication Data

US 2004/0010011 A1    Jan. 15, 2004

(30) Foreign Application Priority Data

Aug. 23, 2000   (FR) .................. 00 10833

(51) Int. Cl.
*A61K 31/445*   (2006.01)
*A61K 31/34*    (2006.01)
*C07D 333/72*   (2006.01)

(52) U.S. Cl. .............. 514/320; 514/324; 514/403; 514/443; 514/469; 514/470; 544/212; 544/358; 544/359; 544/366; 546/186; 546/193; 546/196; 546/202; 548/214; 548/452; 548/466; 548/469; 548/490; 548/491; 548/492; 548/493; 549/398; 549/399; 549/404; 549/405; 549/407; 549/408; 549/419; 549/420; 549/52; 549/55; 549/60; 549/74; 549/75; 549/76

(58) Field of Classification Search ............. 514/299, 514/324, 403, 443, 469, 470, 320; 544/212, 544/358, 359, 366; 546/112, 121, 212, 214, 546/186, 193, 196, 202; 548/214, 452, 466, 548/469, 490, 491, 492, 493; 549/399, 404, 549/405, 407, 52, 55, 398, 408, 410, 419, 549/420, 59, 60, 74, 75, 76

See application file for complete search history.

(56) References Cited

U.S. PATENT DOCUMENTS 3,248,401 A    4/1966   Tondeur et al. ............ 549/468
4,806,663 A    2/1989   Kennedy et al. ............ 549/471
5,100,911 A    3/1992   Binder et al. .............. 514/422
5,223,510 A *  6/1993   Gubin et al. ............... 514/299
6,218,414 B1   4/2001   Nisato ...................... 514/382

FOREIGN PATENT DOCUMENTS

| EP | 0338746 | 10/1989 |
|---|---|---|
| EP | 0471609 | 2/1992 |
| EP | 0617030 | 9/1994 |
| EP | 0752249 | 1/1997 |
| EP | 0835871 | 4/1998 |
| WO | WO 90/02743 | 3/1990 |
| WO | WO 94/29289 | 12/1994 |
| WO | WO 95/10513 | 4/1995 |

OTHER PUBLICATIONS

Black et al. Pharmaceutical compositions . . . CA 121:18076 (1994).*
Dodge et al. "Preparation of 3-[4-(2-heterocyclylethoxy)benzoyl . . . " CA 126:7985 (1996).*
Webster's III dictionary p. 861, 1174 (1990).*
Wyngaarden et al. "Cecil textbook of medicine" p. 247-248 (1983).*
Rubini et al. "Synthesis of isosteric . . . " Tetrhedron v.42(21) p. 6039-45 (1986).*
Patani et al. "Bioisosterism: a rational approach in drug design" Chem. Rev. v. 96 p. 3147-76 (1996).*
Grese et al. "Structure-activity relationship . . . " J. Med. Chem. 40(2) 1460167 (1997).*
Assens et al. "Aminoalkoxybenzoyl . . . " CA 136:216638 (2002).*
Martin, MJ et al, Bioorganic & Medicinal Chemistry Letters, vol. 7, No. 7, pp. 887-892 (1997).

* cited by examiner

*Primary Examiner*—Celia Chang
(74) *Attorney, Agent, or Firm*—James W. Bolcsak

(57) ABSTRACT

The invention relates to benzofuran or benzothiophene derivatives of general formula:

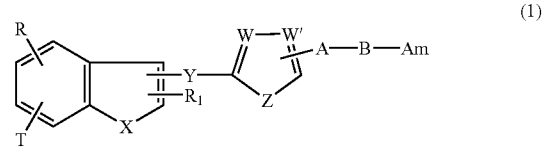

(1)

These compounds are of use as medicinal products, in particular in the treatment of pathological syndromes of the cardiovascular system.

76 Claims, No Drawings

AMINOALKOXYBENZOYL-BENZOFURAN OR BENZOTHIOPHENE DERIVATIVES, METHOD FOR PREPARING SAME AND COMPOSITIONS CONTAINING SAME

The present invention relates, in general, to novel heterocyclic derivatives and also to the process for the preparation thereof.

In particular, the invention relates to novel benzofuran or benzothiophene derivatives which can be represented by the general formula:

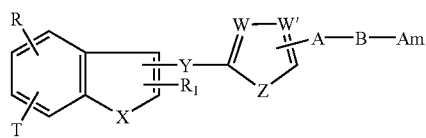

(1)

and also to their pharmaceutically acceptable salts, in which formula:

A represents —O—, —S— or

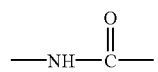

B represents a linear or branched $C_1$–$C_5$ alkylene group optionally substituted with a hydroxyl group, T represents hydrogen or a $C_1$–$C_4$ alkyl radical R represents the cyano or hydroxymethyl group
an oxime group of formula:

$R_4$—O—N=CH— in which $R_4$ represents a $C_1$–$C_4$ alkyl group
a carboxyl group of general formula:

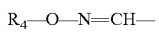

(a)

in which $R_5$ represents hydrogen or an alkali metal atom, a linear or branched $C_1$–$C_{10}$ alkyl group or a $C_3$–$C_6$ cycloalkyl group, or $R_5$ represents the group of general formula:

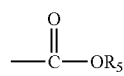

(a-1)

in which r represents 1 to 4
a carboxyl group of general formula:

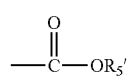

(b)

in which $R'_5$ represents a piperidinyl group optionally N-substituted with a $C_1$–$C_4$ alkyl group or one of the groups of general formula:

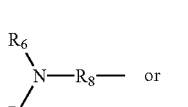

(c)

or

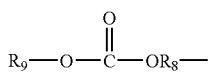

(d)

in which $R_6$ and $R_7$, which may be identical or different, represent a $C_1$–$C_4$ alkyl group, $R_8$ represents a linear or branched $C_1$–$C_6$ alkylene group, and $R_9$ represents hydrogen, an alkali metal atom or a $C_1$–$C_4$ alkyl group,
an aminocarbonyl group of formula:

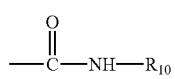

(e)

in which $R_{10}$ represents hydrogen, a $C_1$–$C_4$ alkyl, hydroxyl or amino group, a group (c) above or one of the groups:

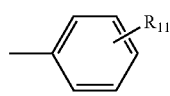

(f)

or

—$R_{12}$—$R_{11}$    (g)

in which $R_{11}$ represents a group (a) and $R_{12}$ represents a $C_1$–$C_6$ alkylene radical,
a group of formula:

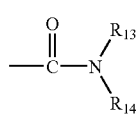

(h)

in which $R_{13}$ and $R_{14}$, which may be identical or different, represent a $C_1$–$C_4$ alkyl radical or a $C_1$–$C_4$ hydroxyalkyl group,
one of the groups of formula below:

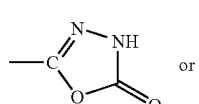

(j)

or

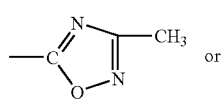

(k)

or

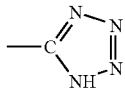

(l)

$R_1$ represents a $C_1$–$C_6$ alkyl, $C_3$–$C_6$ cycloalkyl, phenyl or benzyl group, or a group of formula;

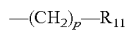

$-(CH_2)_p-R_{11}$ in which $R_{11}$ has the same meaning as previously and p represents 1 to 4, Am represents a nitrogenous group of formula:

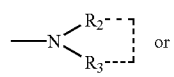

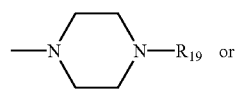 (Am$_2$)

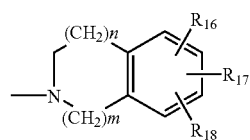 (Am$_3$)

in which:

$R_2$ represents hydrogen, a linear or branched $C_1$–$C_6$ alkyl group optionally substituted with a hydroxyl group, a group (m), a $C_3$–$C_6$ cycloalkyl group or a benzyl group, $R_3$ represents a linear or branched $C_1$–$C_6$ alkyl group optionally substituted with a hydroxyl group, a $C_3$–$C_6$ cycloalkyl group, a group (m), a benzyl group or a phenyl group of formula:

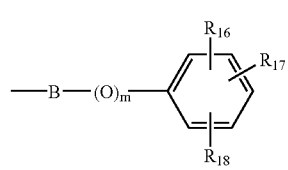 (n)

$R_{16}$, $R_{17}$ and $R_{18}$, which may be identical or different, represent hydrogen, or a hydroxyl, nitro, amino, $C_1$–$C_4$ alkoxy or $C_1$–$C_4$ alkylsulfonamido group, $R_{19}$ represents hydrogen, a $C_1$–$C_5$ alkyl group, the diphenylmethyl group, a mono-, di- or trimethylphenyl group, a mono-, di- or trimethoxyphenyl group, a group (a), a group (b) or a group (c), m and n each represent 0 or 1, $R_2$ and $R_3$, when they are taken together, represent a linear or branched $C_3$–$C_{10}$ alkylene group optionally substituted with the hydroxyl group, with a group (a) or with a group (m) and optionally interrupted by —O—, these alternatives, $R_2$ and $R_3$ which are independent or $R_2$ and $R_3$ taken together, being represented in the formula (Am$_1$) by the symbol

located between $R_2$ and $R_3$

W, W' and Z are such that:

when W and W', which are identical, represent CH, Z represents —O— or —S—, when W represents CH and W' represents C—$R_{20}$, Z represents

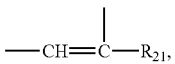

$-CH=\overset{|}{C}-R_{21}$, $R_{20}$ and $R_{21}$ being identical or different and representing hydrogen, a halogen atom, for example fluorine, chlorine or bromine, a $C_1$–$C_4$ alkyl radical, such as methyl, or a $C_1$–$C_4$ alkoxy radical, such as methoxy, X represents —O— or —S—

Y represents a —CO— or —CH$_2$— radical, or a radical of formula

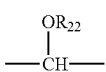 (73)

$\overset{OR_{22}}{\underset{|}{-CH-}}$ in which $R_{22}$ represents hydrogen, a $C_1$–$C_4$ alkyl radical or an acyl radical of formula:

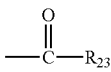 (74)

in which $R_{23}$ represents a $C_1$–$C_4$ alkyl radical, or Y represents

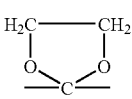

it being understood that the combination of the R, $R_1$ and Am groups contains 0, 1 or 2 groups (a), these benzofuran or benzothiophene derivatives being in the form of individual isomers or of a mixture thereof, with the exclusion of the compound methyl 2-phenyl-3-[4-(2-piperidin-1-ylethoxy)benzoyl]-benzo[b]thiophene-6-carboxylate of formula (72) below:

(72)

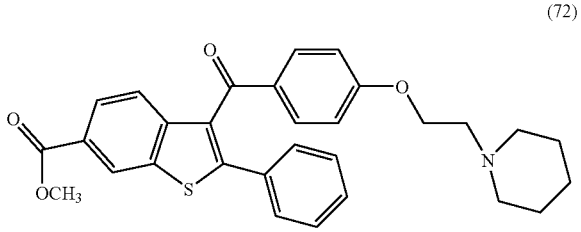

Classes of preferred compounds of the invention can be represented by the compounds of formula (1) in which:
either R represents an isopropoxycarbonyl group
or Am represents a diethylpiperidino group.

Likewise, a specific class of compounds of formula I is that in which: Y represents a —CO— radical.

Another class of preferred compounds of formula (1) is that in which:

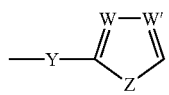

represents a benzoyl radical.

Likewise, a specific class of compounds of formula (1) is that in which the entity:

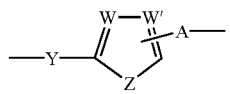

represents a 4-oxybenzoyl radical.

Likewise, the compounds of formula (1) in which X represents —O— are preferred compounds, as are those in which the chain:

is located at position 4.

Finally, the compounds of formula (1) in which $R_1$ represents n-butyl, B represents a propylene group and Am represents a diethylpiperidinyl group, in particular 3,5-diethylpiperidinyl, can also be regarded as preferred.

Compounds of formula (1) can exist in the form of optical or geometrical isomers, for example the compounds in question in which Am represents a diethylpiperidinyl group or in which R represents an —$R_4$—O—N=CH— group.

Consequently, the invention relates both to the individual isomers of the compounds of formula (1) and to mixtures thereof, in particular the racemic mixture.

The invention also relates to the pharmaceutically acceptable salts of the compounds of formula (1) formed from an organic or inorganic acid.

As examples of organic salts of this type, mention may be made of oxalate, maleate, fumarate, methanesulfonate, benzoate, ascorbate, pamoate, succinate, hexamate, bismethylenesalicylate, ethanedisulfonate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulfonate, p-toluenesulfonate and theophyllineacetate salts and the salts formed from an amino acid, such as the lysine or histidine salt.

As inorganic salts of this type, mention may be made of hydrochloride, hydrobromide, sulfate, sulfamate, phosphate and nitrate salts.

It has been found that the compounds of the invention possess noteworthy pharmacological properties, in particular antiarrhythmic properties, since they have proved to be capable of suppressing or preventing disorders of ventricular and atrial rhythm. Most of the compounds of the invention have electrophysiological properties of classes 1, 2, 3 and 4 of the Vaughan-Williams classification, which confer bradycardic, antihypertensive and anti-α-adrenergic and anti-β-adrenergic properties which are noncompetitive. In addition, most of the compounds have also displayed antioxidant properties, an affinity for sigma receptors and an ability to enhance NO synthesis.

Moreover, these compounds of the invention demonstrate inhibitory properties with respect to various hormonal agents, such as, for example, angiotensin II, arginine vasopressin, neuropeptide Y or endothelin.

These properties are capable of rendering the compounds in question very useful in the treatment of certain pathological syndromes of the cardiovascular system, in particular in the treatment of angina pectoris, hypertension, arrhythmia, in particular atrial, ventricular or supraventricular arrhythmia, or cerebral circulatory insufficiency. Likewise, the compounds of the invention can be used in the treatment of heart failure or myocardial infarction, possibly complicated by heart failure, or for the prevention of post-infarction mortality.

In the antitumor field, the compounds of the invention may be of use as potentiators of anticancer agents.

Consequently, the invention also relates to a medicinal product, characterized in that it comprises a compound derived from benzofuran or benzothiophene, or a pharmaceutically acceptable salt of the latter, according to the invention.

Consequently, the invention also relates to pharmaceutical or veterinary compositions comprising, as active principle, at least one compound of the invention in combination with a suitable excipient or pharmaceutical vehicle.

Depending on the route of administration chosen, the daily dosage for a human weighing 60 kg will lie between 2 and 2000 mg of active principle, in particular between 50 and 500 mg of active principle.

The compounds of formula (1) can be prepared according to the following methods:

I. The compounds of formula (1) in which
Y represents the —CO— group
$R_1$ comprises no carboxylic or alkali metal carboxylate group
Am represents a group ($Am_1$) or ($Am_2$), this group comprising no carboxylic or alkali metal carboxylate group, or Am represents a group ($Am_3$) in which $R_{16}$ and/or $R_{17}$ and/or $R_{18}$ are different from an amino or $C_1$–$C_4$ alkylsulfonamido group, can be obtained:

A.—When R represents a cyano or hydroxymethyl group, a group (a) in which $R_5$ represents a $C_1$–$C_{10}$ alkyl or $C_3$–$C_6$ cycloalkyl group or else the group (k), by reacting, in the presence of a basic agent such as an alkali metal hydroxide or carbonate, a ketone derivative of general formula:

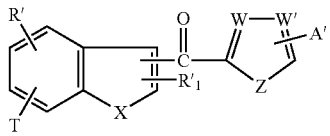
(2)

in which $R'_1$ represents a $C_1$–$C_6$ alkyl, $C_3$–$C_6$ cycloalkyl, phenyl or benzyl group or a group (m) comprising no carboxylic or alkali metal carboxylate group, T, W, W', X and Z have the same meaning as above, A' represents OH, SH or $NH_2$ and R' represents the cyano or hydroxymethyl group, the group (k) or a —$CO_2R''_5$ group, in which $R''_5$ represents a $C_1$–$C_{10}$ alkyl or $C_3$–$C_6$ cycloalkyl radical, with a compound of general formula:

$R_{24}$—B—Am' (3)

in which Am' represents a group ($Am_1$) or ($Am_2$), this group comprising no carboxylic or alkali metal carboxylate group, or else a group ($Am_3$) in which $R_{16}$ and/or $R_{17}$ and/or $R_{18}$ are different from an amino group or a $C_1$–$C_4$ alkylsulfonamido group, B has the same meaning as above and $R_{24}$ represents:

either a halogen atom, such as, for example, a chlorine atom, or a $C_1$–$C_4$ alkylsulfonyloxy or $C_6$–$C_{10}$arylsulfonyloxy radical, which makes it possible to obtain, in the free base form, the desired compounds of formula I in which A represents —O— or —S— or a halocarbonyl group, which makes it possible to obtain, in the free base form, the desired compounds of formula (1) in which A represents

Usually, the reaction takes place at the reflux temperature of the solvent used or at a temperature not exceeding 90° C., this solvent possibly being, for example, a polar solvent such as N,N-dimethylformamide or a ketone such as, for example, methyl ethyl ketone.

B.—When R represents the cyano group, an $R_4$—O—N=CH— group, a group (a) in which $R_5$ represents a $C_1$–$C_{10}$ alkyl or $C_3$–$C_6$ cycloalkyl group or else the group (k), by reacting a compound of general formula:

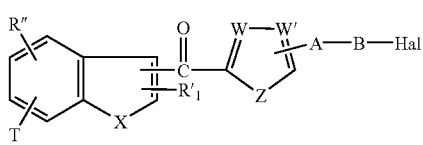
(4)

in which A, B, $R'_1$, T, X, W, W' and Z have the same meaning as above, and R" represents the cyano group, the group (k), an $R_4$—O—N=CH— group or a —$CO_2R''_5$ group in which $R''_5$ has the same meaning as above, and Hal represents a halogen atom, such as, for example, chlorine or bromine, with a compound of general formula:

H—Am' (5)

optionally in the form of a salt, for example in the hydrochloride form, in which Am' has the same meaning as above, the reaction taking place in the presence of a basic agent such as an alkali metal hydroxide or carbonate or an excess of amine of formula (5) in basic form, which gives the desired compounds of formula (1) in the free base form.

Generally, the reaction takes place at the reflux temperature of the medium and in a polar solvent, such as N,N-dimethylformamide, acetonitrile or methyl ethyl ketone, or an apolar solvent, such as benzene or toluene.

C.—When R represents the cyano group, an $R_4$—O—N=CH— group, a group (a) in which $R_5$ represents a $C_1$–$C_{10}$ alkyl or $C_3$–$C_6$ cycloalkyl group or else the group (k), by reacting a compound of general formula:

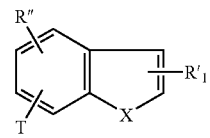
(6)

in which R", $R'_1$, T and X have the same meaning as above, with a halide of general formula:

(7)

in which A, B, Am', W, W', Z and Hal have the same meaning as above, the reaction optionally taking place in the presence of a Lewis acid, such as aluminum chloride, stannic chloride, ferric chloride or silver trifluoromethanesulfonate, which gives the desired compounds of formula (1) in the free base form.

Usually, the above reaction takes place in an apolar solvent such as a halogenated compound, for example dichloromethane or dichloroethane, and at a temperature of between ambient temperature and the reflux temperature.

Alternatively, it is possible to obtain the compounds of formula (1) in which the group Am represents a group ($Am_1$) in which $R_2$ and $R_3$ are different, by converting a secondary amine of formula (1) comprising a group ($Am_1$) of formula —NH—$R_2$, to a tertiary amine by reaction by means of a compound of general formula:

Hal-$R_3$ (8)

in which Hal represents a halogen atom, preferably bromine, and $R_3$ has the same meaning as above, the reaction preferably taking place at the reflux temperature, in the presence of a basic agent such as an alkali metal hydroxide or carbonate, which gives the desired compounds of formula (1) in the free base form.

The compounds of formula (1) in which R represents an oxime group of formula $R_4$—O—N=CH— can be in the form of stereoisomers.

The methods described above under B) and C) make it possible to obtain these oxime derivatives in the form of mixtures of isomers. However, these isomers may be produced in separate form using known methods such as, for example, chromatography or precipitation.

D.—When R represents the group (j), by reacting, preferably at the reflux temperature of the medium, a compound of general formula:

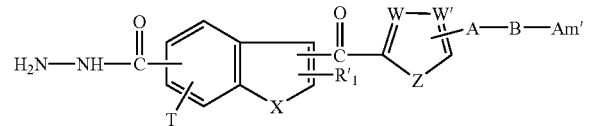
(9)

in which A, B, T, W, W', X and Z have the same meaning as above, with phosgene, which gives the desired compounds of formula (1) in the hydrochloride form, which hydrochloride can be treated, if necessary, with a basic agent such as an alkali metal hydroxide or an alkali metal carbonate, which gives the desired compounds in the free base form.

The benzofuran or benzothiophene derivatives of formula (1), which also correspond to the general formula:

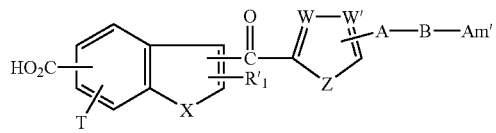
(10)

in which A, Am', B, R'$_1$, T, X, W, W' and Z have the same meaning as above, are themselves synthetic intermediates for the preparation of other compounds of formula (1) in which Y represents —CO— and Am represents a group (Am$_1$) or (Am$_2$), this group comprising no carboxylic or alkali metal carboxylate group, or else a group (Am$_3$) in which R$_{16}$ and/or R$_{17}$ and/or R$_{18}$ are different from an amine or a C$_1$–C$_4$ alkylsulfonamido group and in which R$_1$ comprises no carboxylic or alkali metal carboxylate group.

To this end, the following methods, starting from the compounds of formula (10) in question, can be employed to obtain the desired compounds of formula (1), that is to say:

E.—When R represents a group (b) in which R'$_5$ represents a group (c):

a) if this group (c) is of the primary dialkylaminoalkyl type, a compound of formula (10), after protection of the amine functional group when Am' represents a group (Am$_1$) in which R$_2$ represents hydrogen, is reacted, preferably in a polar solvent, such as N,N-dimethylformamide, and usually at a temperature of between 30 and 50° C., with an alcohol of general formula:

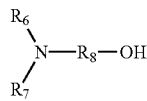
(11)

in which R$_6$ and R$_7$ have the same meaning as above and R$_8$ represents a linear C$_1$–C$_6$ alkylene group, the reaction taking place in the presence of carbonyldiimidazole and 1,8-diazabicyclo[5.4.0]undec-7-ene, and then, if necessary, the compound formed is deprotected, which gives, in the free base form, the desired compounds of formula (1);

b) if this group (c) is of the secondary or tertiary dialkylaminoalkyl type, a compound of formula (10), after protection of the amine functional group when Am' represents a group (Am$_1$) in which R$_2$ represents hydrogen, is reacted, preferably in an aprotic solvent, such as a halogenated hydrocarbon, and generally at the reflux temperature of the medium, with a halogenating agent, such as thionyl chloride, to obtain an acyl halide, which is subsequently treated, preferably at ambient temperature, with an alcohol of formula (11) above in which R$_6$ and R$_7$ have the same meaning as above and R$_8$ represents a secondary or tertiary C$_2$–C$_6$ alkylene group, and then, if necessary, the compound formed is deprotected, which gives the compounds of formula (1) in the hydrohalide form or in the free base form, when the compound of formula (10) is in excess, which hydrohalide can be treated, if necessary, with a basic agent, such as an alkali metal hydroxide or an alkali metal carbonate, to produce the desired compounds in the free base form.

F.—When R represents either a group (a) in which R$_5$ represents a C$_1$–C$_{10}$ alkyl or C$_3$–C$_6$ cycloalkyl group or a group (b) in which R'$_5$ represents a piperidinyl group optionally N-substituted with a C$_1$–C$_4$ alkyl group or in which R'$_5$ represents a group (d) comprising no carboxylic or alkali metal carboxylate group, a compound of formula (10), after protection of the amine functional group when Am' represents a group (Am$_1$) in which R$_2$ represents hydrogen, is reacted, preferably in a halogenated hydrocarbon and generally at the reflux temperature of the medium, with a halogenating agent, such as thionyl chloride, to produce an acyl halide, which is subsequently treated with an alcohol of general formula:

$$R'''_5\text{—OH} \tag{12}$$

in which R'''$_5$ represents a C$_1$–C$_{10}$ alkyl or C$_3$–C$_6$ cycloalkyl group or a group (b) in which R'$_5$ represents a piperidinyl group optionally N-substituted with a C$_1$–C$_4$ alkyl group or R'$_5$ represents a group (d) comprising no carboxylic or alkali metal carboxylate group, and then, if necessary, the compound formed is deprotected, which gives the desired compounds of formula (1) in the hydrohalide form or in the free base form when the compound of formula (10) is in excess, which hydrohalide can be treated, if necessary, with a basic agent, such as an alkali metal hydroxide or an alkali metal carbonate, to produce the desired compounds in the free base form.

G.—When R represents a group (e) in which R$_{10}$ represents a group (f) comprising no carboxylic or alkali metal carboxylate group, a compound of formula (10), after protection of the amine functional group when Am' represents a group (Am$_1$) in which R$_2$ represents hydrogen, is reacted, preferably in a halogenated hydrocarbon and generally at the reflux temperature, with a halogenating agent, such as thionyl chloride, to produce an acyl chloride, which is subsequently treated, preferably at ambient temperature, with a compound of formula:

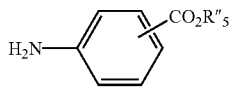

(13)

in which R″$_5$ has the same meaning as above, and then, if necessary, the compound formed is deprotected, which gives, in the free base form, the desired compounds of formula (1) in which R$_{10}$ represents a group (f) in which the R$_{11}$ group represents a group (a) in which R$_5$ represents a C$_1$–C$_4$ alkyl or C$_3$–C$_6$ cycloalkyl group.

H.—When R represents a group (e) in which R$_{10}$ represents a C$_1$–C$_4$ alkyl group, an amino group or a group (c), a compound of formula (10), after protection of the amine functional group when Am' represents a group (Am$_1$) in which R$_2$ represents hydrogen, is reacted, preferably in a halogenated hydrocarbon and generally at the reflux temperature, with a halogenating agent, such as thionyl chloride, to produce an acyl halide, which is subsequently treated, preferably at ambient temperature, with an amine of general formula:

R'$_{10}$—NH$_2$ (14)

or

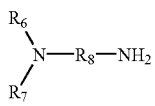

(15)

in which R$_6$, R$_7$ and R$_8$ have the same meaning as above and R'$_{10}$ represents a C$_1$–C$_4$ alkyl or amino radical, and then, if necessary, the compound formed is deprotected, which gives, optionally after basic treatment, the desired compound of formula (1) in the hydrohalide form or in the free base form when the compound of formula (10) is in excess, which hydrohalide can be treated, if necessary, with a basic agent, such as an alkali metal hydroxide or an alkali metal carbonate, to produce the desired compounds in the free base form.

I.—When R represents a group (e) in which R$_{10}$ represents a group (g) comprising no carboxylic or alkali metal carboxylate group, a compound of formula (10), after protection of the amine functional group when Am' represents a group (Am$_1$) in which R$_2$ represents hydrogen, is reacted, preferably in a polar or apolar solvent, such as N,N-dimethylformamide or a halogenated hydrocarbon, for example dichloromethane, with a salt of a compound of general formula:

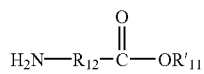

(16)

in which R$_{12}$ has the same meaning as above and R'$_{11}$ represents a C$_1$–C$_4$ alkyl or C$_3$–C$_6$ cycloalkyl radical, the reaction taking place in the presence of an acid scavenger such as an amine, for example triethylamine, and then, if necessary, the compound formed is deprotected, which gives, in the free base form, the desired compounds of formula (1) in which R$_{10}$ represents a group (g) in which the group R$_{11}$ represents a group (a) in which R$_5$ represents a C$_1$–C$_4$ alkyl or a C$_3$–C$_6$ cycloalkyl group.

J.—When R represents a group (h), by reacting a compound of formula (10), after protection of the amine functional group when Am' represents a group (Am$_1$) in which R$_2$ represents hydrogen, preferably in a halogenated hydrocarbon and generally at the reflux temperature of the medium, with a halogenating agent, such as thionyl chloride, to produce an acyl halide, which is subsequently treated with an amine of general formula:

(17)

in which R$_{13}$ and R$_{14}$ have the same meaning as above, and then, if necessary, the compound formed is deprotected, which gives a salt of the desired compound of formula (1), which is treated with a suitable basic agent, such as an alkali metal carbonate, to produce, in the free base form, the desired compounds of formula (1).

K.—When R represents a group (e) in which R$_{10}$ represents the hydroxyl group, a compound of formula (10), after protection of the amine functional group when Am' represents a group (Am$_1$) in which R$_2$ represents hydrogen, is reacted with a benzyloxyamine salt, for example the hydrochloride, in the presence of an acid scavenger, for example an amine such as triethylamine, and of benzotriazol-1-yloxytris(dimethylamino)phosphonium hexafluorophosphate, hereinafter referred to as BOP, and then, if necessary, the compound formed is deprotected, which gives benzyloxyaminocarbonyl derivatives, which are hydrogenated in the presence of a suitable catalyst, for example palladium charcoal or platinum black, to produce, in the free base form, the desired compounds of formula (1).

In the processes E. to K. above, the protection of the amine functional group of the compound of formula (10), i.e. the protection envisaged when Am' represents a group (Am$_1$) in which R$_2$ represents hydrogen, can be obtained, for example, by treatment by means of a compound which makes possible the attachment of a group which can be easily removed, in particular by means of 9-fluorenylmethyl chloroformate, and the deprotection is subsequently carried out by treatment with a secondary amine, for example piperidine or diethylamine, in a suitable solvent, for example N,N-dimethylformamide.

Other compounds of formula (1) can be used as synthetic intermediates for compounds of the invention, in particular the cyano derivatives which also correspond to the general formula:

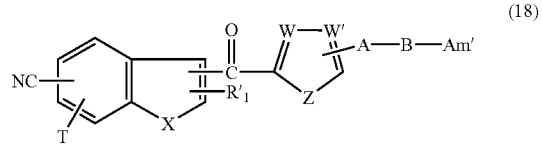

(18)

in which Am', A, B, R'$_1$, T, W, W', X and Z have the same meaning as above.

Thus, the following methods, starting with the compounds of formula (18) in question, can be employed to prepare the compounds of formula (1) in which Y represents —CO—, Am represents a group (Am$_1$) or (Am$_2$), this group comprising no carboxylic or alkali metal carboxylate group, or else a group (Am$_3$) in which R$_{16}$ and/or R$_{17}$ and/or R$_{18}$ are different from an amino group or a C$_1$–C$_4$ alkylsulfonamido group, and in which R$_1$ comprises no carboxylic or alkali metal carboxylate group, that is to say:

L.—When R represents a group (e) in which R$_{10}$ represents hydrogen, a compound of formula (18) is hydrolyzed in the presence of a strong acid, such as, for example, sulfuric acid, and generally at ambient temperature, which gives, in the free base form, the desired compounds of formula (1).

M.—When R represents the group (I), a compound of formula (18) is reacted, preferably in an aprotic solvent, such as an aromatic hydrocarbon, for example benzene or toluene, and usually at the reflux temperature of the medium, with tributylazidotin, which gives, in the free base form, the desired compounds of formula (1).

II. The compounds of formula (1) in which:

Y represents the —CO— group

R$_1$ comprises no carboxylic or alkali metal carboxylate group

Am represents a group (Am$_1$) comprising no carboxylic or alkali metal carboxylate group and in which R$_{16}$ and/or R$_{17}$ and/or R$_{18}$ represent the amino group or a C$_1$–C$_4$ alkylsulfonamido group, or else Am represents a group (Am$_3$) in which R$_{16}$ and/or R$_{17}$ and/or R$_{18}$ represent the amino group or a C$_1$–C$_4$ alkylsulfonamido group, can be obtained in the following way:

a) when R$_{16}$ and/or R$_{17}$ and/or R$_{18}$ represent the amino group, by hydrogenating, preferably at ambient temperature and at normal pressure, a nitro compound of formula:

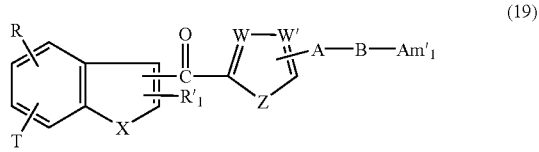

(19)

in which A, B, R'$_1$, T, W, W', X and Z have the same meaning as above, R has the same meaning as above but comprises no carboxylic or alkali metal carboxylate group, and Am'$_1$ represents either a group (Am$_1$) comprising no carboxylic or alkali metal carboxylate group and in which R$_{16}$ and/or R$_{17}$ and/or R$_{18}$ represent the nitro group, or a group (Am$_3$), in which R$_{16}$ and/or R$_{17}$ and/or R$_{18}$ represent the nitro group, in the presence of a suitable catalyst such as Raney nickel, platinum oxide or palladium oxide or zinc in hydrochloric acid medium, and preferably in a polar solvent, for example an alcohol, which gives, in the free base form, the desired compounds of formula (1).

b) When R$_{16}$ and/or R$_{17}$ and/or R$_{18}$ represents a C$_1$–C$_4$ alkylsulfonamido group, by reacting an amino compound of formula:

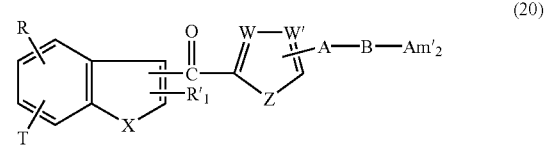

(20)

in which A, B, R'$_1$, T, W, W', X and Z have the same meaning as above, R has the same meaning as above but comprises no carboxylic or alkali metal carboxylate group, and Am'$_2$ represents either a group (Am$_1$) comprising no carboxylic or alkali metal carboxylate group and in which R$_{16}$ and/or R$_{17}$ and/or R$_{18}$ represent the amino group, or a group (Am$_3$) in which R$_{16}$ and/or R$_{17}$ and/or R$_{18}$ represent the amino group, with a halide of general formula:

Hal-SO$_2$—R'$_{16}$ (21)

or an anhydride of general formula:

(R'$_{16}$SO$_2$)$_2$O (22)

in which R'$_{16}$ represents a linear or branched C$_1$–C$_4$ alkyl radical, the reaction preferably taking place at ambient temperature and in an organic solvent, for example an aprotic solvent, and optionally in the presence of an acid acceptor, such as an amine, for example triethylamine, which gives, in the free base form, the desired compounds of formula (1).

III. The compounds of formula (1) in which:

Y represents the —CO— group the combination formed by R, R$_1$ and Am, more precisely R, R$_1$, and (Am$_1$) or (Am$_2$), comprising 1 or 2 carboxylic or alkali metal carboxylate groups, that is to say 1 or 2 groups (a) above in which R$_5$ represents hydrogen or an alkali metal atom, can be obtained:

a) when, in this formula (1), one or two of the groups R, R$_1$, and (Am$_1$) or (Am$_2$) comprise a —CO$_2$R$_5$ group in which R$_5$ represents hydrogen or an alkali metal atom, the other group(s) being different from a —CO$_2$R$_5$ group in which R$_5$ represents a C$_1$–C$_{10}$ alkyl or C$_3$–C$_6$ cycloalkyl radical, by saponifying, in the presence of a basic agent, namely an alkali metal hydroxide, for example sodium hydroxide, a compound of formula:

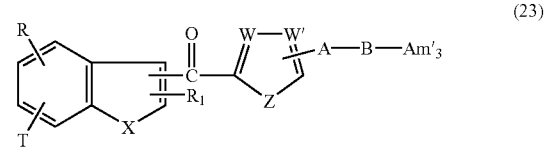

(23)

in which A, B, R, R$_1$, T, W, W', X and Z have the same meaning as above, Am'$_3$ represents a group (Am$_1$) or (Am$_2$) as defined above and R, R$_1$, and (Am$_1$) or (Am$_2$) are such that one or two of them comprise a —CO$_2$R''$_5$ group in which R''$_5$ has the same meaning as above, the other group(s) being different from a —CO$_2$R$_5$ group in which R$_5$ represents a C$_1$–C$_{10}$ alkyl or C$_3$–C$_6$ cycloalkyl radical, which gives, in the free base form, the compounds of formula (1) in which one or two of the groups R, $R_1$, and $(Am_1)$ or $(Am_2)$ comprise a —$CO_2R_5$ group in which $R_5$ represents an alkali metal atom, which compound is treated, if necessary, with a strong acid, for example hydrochloric acid, which gives, in the free base form, the desired compounds of formula (1) in which $R_5$ represents hydrogen. However, when, in this formula (1), R represents the cyano group and one of the groups $R_1$, $(Am_1)$ or $(Am_2)$ comprises a carboxylic group, it is also possible to treat, by means of tributyltin oxide, a compound of formula (1) in which Y represents —CO—, A, B, T, W, W', X and Z have the same meaning as above, R represents the cyano group, and $R_1$, $(Am_1)$ and $(Am_2)$ are such that one of them comprises a —$CO_2R''_5$ group in which $R''_5$ has the same meaning as above, to produce, in the free base form, the desired compounds of formula (1).

b) When, in this formula (1), one of two of the groups R, $R_1$, $(Am_1)$ or $(Am_2)$ comprises a —$CO_2R_5$ group in which $R_5$ represents hydrogen or an alkali metal atom, and the other comprises a —$CO_2R_5$ group in which $R_5$ represents a $C_1$–$C_{10}$ alkyl or $C_3$–$C_6$ cycloalkyl group, the third group being different from a —$CO_2R_5$ group in which $R_5$ represents a $C_1$–$C_{10}$ alkyl or $C_3$–$C_6$ cycloalkyl radical, either by hydrogenating a compound of formula:

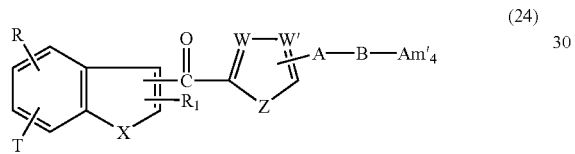

(24)

in which A, B, R, $R_1$, T, W, W', X and Z have the same meaning as above, $Am'_4$ represents a group $(Am_1)$ or $(Am_2)$ as defined above, and R, $R_1$, and $(Am_1)$ or $(Am_2)$ are such that one of them comprises a —$CO_2R''_5$ group in which $R''_5$ has the same meaning as above and another of them comprises a benzyloxycarbonyl group, the third group being different from a —$CO_2R_5$ group in which $R_5$ represents a $C_1$–$C_{10}$ alkyl or $C_3$–$C_6$ cycloalkyl radical, in the presence of a suitable catalyst, for example palladium charcoal or platinum black, and preferably in an organic solvent;

or by hydrolyzing a compound of formula:

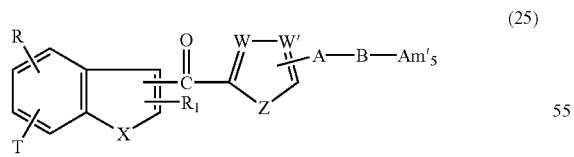

(25)

in which A, B, R, $R_1$, T, W, W', X and Z have the same meaning as above, $Am'_5$ represents a group $(Am_1)$ or $(Am_2)$ as defined above, and R, $R_1$, and $(Am_1)$ or $(Am_2)$ are such that one of them comprises a —$CO_2R''_5$ group in which $R''_5$ has the same meaning as above and another of them comprises a t-butoxy-carbonyl group, the third group being different from a —$CO_2R_5$ group in which $R_5$ represents a $C_1$–$C_{10}$ alkyl or $C_3$–$C_6$ cycloalkyl radical, in the presence of trifluoroacetic acid, and preferably in an organic solvent, for example an aprotic solvent such as methylene chloride, which makes it possible to produce the desired compounds of formula (1) in which one of two of the groups R, $R_1$, and $(Am_1)$ or $(Am_2)$ comprises a —$CO_2R_5$ group in which $R_5$ represents a $C_1$–$C_{10}$alkyl or $C_3$–$C_6$ cycloalkyl group, and the other comprises a —$CO_2R_5$ group in which $R_5$ represents hydrogen, that is to say a carboxylic group, which compounds can be treated, if necessary, with a suitable basic agent, for example an alkali metal hydroxide, to produce, in the free base form, the desired compounds of formula (1) in which one of two of the groups R, $R_1$, and $(Am_1)$ or $(Am_2)$ comprises a —$CO_2R_5$ group in which $R_5$ represents an alkali metal atom, the other a group of formula —$CO_2R_5$ in which $R_5$ represents a $C_1$–$C_{10}$ alkyl or $C_3$–$C_6$ cycloalkyl radical, which compounds can themselves be treated, if necessary, with a strong acid, for example hydrochloric acid, to produce, in the free base form, the desired compounds of formula (1) in which one of two of the groups R, $R_1$, and $(Am_1)$ or $(Am_2)$ comprises a carboxylic group, the other a —$CO_2R_5$ group in which $R_5$ represents a $C_1$–$C_{10}$ alkyl or $C_3$–$C_6$ cycloalkyl group.

IV. The compounds of formula (1) in which Y represents a group

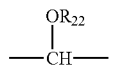

can be obtained:

a) when $R_{22}$ represents hydrogen, by reducing a compound of formula (1) in which Y represents the —CO— group, by means of an alkali metal borohydride, such as sodium borohydride, and preferably in a solvent such as an alcohol or an ether, which gives, in the free base form, the desired compounds of formula (1), b) when $R_{22}$ represents a $C_1$–$C_4$ alkyl radical or an acyl radical of formula —CO—$R_{23}$, by reacting the secondary alcohol thus formed, that is to say a compound of formula (1) in which Y represents the —CHOH— group, with:

either an alkali metal hydroxide, and then with a halide of general formula:

$R_{23}$-Hal (26)

in which Hal and $R_{23}$ have the same meaning as above, or an acyl halide of general formula:

(27)

in which Hal and $R_{23}$ have the same meaning as above, the reaction taking place in the presence of an acid acceptor such as pyridine, so as to produce, in the free base form, the desired compounds of formula (1).

Depending on the structure of the starting product, mixtures of compounds can be obtained during the reduction.

These compounds can be separated from their mixture according to conventional techniques, for example by elution chromatography.

V. The compounds of formula (1) in which Y represents the —$CH_2$— group can be prepared, preferably, by reducing a compound of formula (1) in which Y represents the —CHOH— group, by means of an alkali metal borohydride, such as sodium borohydride, in the presence of trifluoroacetic acid, and preferably in a solvent such as an alcohol, an ether or a halogenated hydrocarbon, which gives, in the free base form, the desired compounds of formula (1).

Generally, the reduction of the compounds of formula (1) in which Y represents a —CO— or —CHOH— group is carried out at a temperature of the order of $-10°$ to $+10°$ C., preferably at $0°$ C.

The compounds of formula (1) obtained in the free base form according to one or other of the methods described above can subsequently be converted to pharmaceutically acceptable salts by reaction with a suitable organic or inorganic acid, for example oxalic, maleic, fumaric, methanesulfonic, benzoic, ascorbic, pamoic, succinic, hexamic, bismethylenesalicylic, ethanedisulfonic, acetic, propionic, tartaric, salicylic, citric, gluconic, lactic, malic, cinnamic, mandelic, citraconic, aspartic, palmitic, stearic, itaconic, glycolic, p-aminobenzoic, glutamic, benzenesulfonic, p-toluenesulfonic or theophyllineacetic acid, or with lysine or histidine.

The compounds of formula (2) in which R' represents a cyano or —$CO_2R''_5$ group, and also the compounds of formula (4) in which R'' represents a cyano or —$CO_2R''_5$ group, can be prepared starting from a compound of general formula:

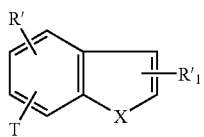

(28)

in which R' represents a cyano or —$CO_2R''_5$ group and $R'_1$, T and X have the same meaning as above, which compound is treated with a compound of general formula:

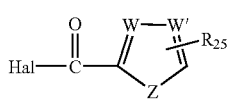

(29)

in which W, W', Z and Hal have the same meaning as above and $R_{25}$ represents a methoxy, acetylthio or nitro group or -A-B-Hal in which A, B and Hal have the same meaning as above, in the presence of a Lewis acid as catalyst, for example ferric chloride, stannic chloride or aluminum chloride, and in a solvent such as a halogenated hydrocarbon, so as to obtain a ketone of general formula:

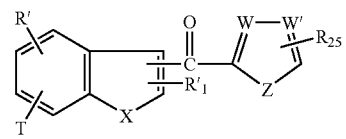

(30)

in which R' represents a cyano or —$CO_2R''_5$ group and $R'_1$, T, W, W', X, Z and $R_{25}$ have the same meaning as above, which gives:

when $R_{25}$ represents an -A-B-Hal group, desired compounds of formula (4), when $R_{25}$ represents the methoxy group, compounds which are O-demethylated in the presence of a suitable agent, such as pyridine hydrochloride, boron tribromide or aluminum chloride, to produce the compounds of the formula (2) in which A' represents OH, when $R_{25}$ represents the acetylthio group, compounds which are treated by means of a suitable basic agent, such as an alkali metal hydroxide, to produce the desired compounds of formula (2) in which A represents SH, when $R_{25}$ represents the nitro group, compounds which are reduced by hydrogenation in the presence of a suitable catalyst, such as palladium charcoal, to produce the desired compounds of formula (2) in which A' represents $NH_2$.

Alternatively, the compounds of formula (2) in which A' represents the hydroxyl group and R' represents a cyano or —$CO_2R''_5$ group can be obtained starting from a compound of formula (28) which is treated with phosgene and then with a compound of general formula:

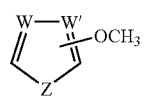

(31)

in which W, W' and Z have the same meaning as above, the reaction taking place in the presence of a Lewis acid, such as, for example, aluminum chloride or stannic chloride, to produce the ketones of formula (30) in which $R_{25}$ represents the methoxy group.

These ketones of formula (30) thus produced are then subjected to O-demethylation in the presence of a suitable agent, such as pyridine hydrochloride, boron tribromide or aluminum chloride, to finally produce the desired compounds.

The compounds of formula (2) in which A' represents the hydroxyl group and R' represents the hydroxymethyl group can be prepared starting from a compound of formula (2) in which R' represents a —$CO_2R'_5$ group, according to the sequence of stages below:

a) the ester of formula (2) in question is treated, at the reflux temperature of the medium, by means of glycol in the presence of p-toluenesulfonic acid, to form a diether of general formula:

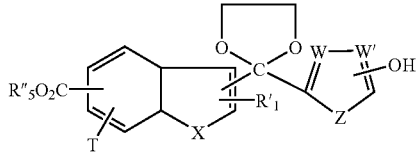

(32)

in which R'$_1$, R''$_5$, T, X, W, W' and Z have the same meaning as above, b) this compound of formula (32) is reduced by means of an alkali metal hydride such as lithium aluminum hydride, and in a solvent such as an ether, to produce a dialcohol of general formula:

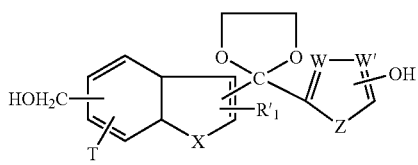

(33)

in which R'$_1$, T, X, W, W' and Z have the same meaning as above, c) the dialcohol thus obtained is deprotected by means of pyridine p-toluenesulfonate, preferably at the reflux temperature of the medium, which gives the desired compounds.

The compounds of formula (2) in which R' represents the group (k) can be obtained by treating a compound of formula (2) in which R' represents a —CO$_2$R''$_5$ group, with acetamide oxime in the presence of an alkali metal hydride, which gives the desired compounds.

The compounds of formula (4) in which R'' represents the cyano group, a —CO$_2$R''$_5$ group or the group (k) can be prepared by reacting, preferably at the reflux temperature, a compound of formula (2) in which R' represents a cyano or —CO$_2$R''$_5$ group, with a dihalogenated compound of general formula:

Hal-B-Hal  (34)

in which Hal represents a halogen atom, preferably bromine, and B has the same meaning as above, the reaction taking place in the presence of a basic agent, such as an alkali metal hydroxyl or carbonate, to give the desired compounds.

Likewise, the compounds of formula (4) in which R'' represents an R$_4$—O—N=CH— group can be obtained:

a) by reducing an ester of formula (28) in which R' represents a group (a) in which R$_5$ represents a C$_1$–C$_{10}$ alkyl or C$_3$–C$_6$ cycloalkyl radical, by means of a suitable agent, such as a hydride, for example lithium aluminum hydride, to form an alcohol of general formula:

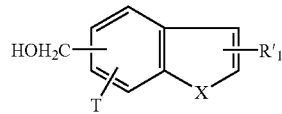

(35)

in which R'$_1$, T and X have the same meaning as above, b) by oxidizing this alcohol of formula (35) with oxalyl chloride so as to form the aldehyde of general formula:

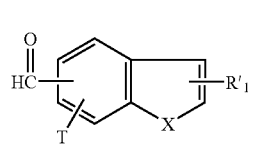

(36)

in which R'$_1$, T and X have the same meaning as above, and c) by reacting the aldehyde thus obtained, with a compound of general formula:

R$_4$—O—NH$_2$  (37)

optionally in the form of one of its salts, in an acid-scavenging solvent, for example pyridine, to form the oxime of general formula:

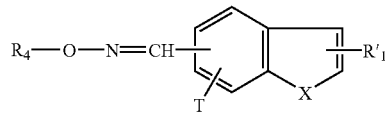

(38)

in which R'$_1$, T and R$_4$ have the same meaning as above.

The compound of formula (38) in question is then treated either with a compound of formula (29) so as to produce the desired compounds, or first with phosgene, and then with a compound of formula (31), and finally with an agent suitable for causing an O-demethylation, for example aluminum chloride, pyridine hydrochloride or boron tribromide, which gives the desired compounds.

As regards the compounds of formula (6), they can be obtained as follows:

A—The compounds of formula (6) in which R'' represents a —CO$_2$R''$_5$ group located at position 5 and R'$_1$, located at position 2, represents a C$_1$–C$_6$ alkyl, C$_3$–C$_6$ cycloalkyl, phenyl or benzyl group, can be prepared according to the sequence of stages below:

a) first, a benzoate of general formula:

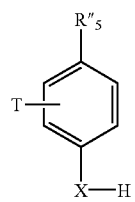

(39)

in which R″₅, T and X have the same meaning as above, is treated with methanesulfonic acid in the presence of phosphorus pentoxide and of hexamethylenetetramine, to give a formyl derivative of general formula:

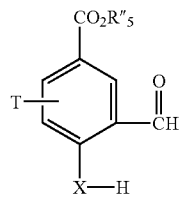
(40)

in which R″₅, T and X have the same meaning as above, b) this compound of formula (40) is subsequently reacted with an ester of general formula:

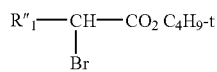
(41)

in which R″₁, represents a $C_1$–$C_6$ alkyl, $C_3$–$C_6$ cycloalkyl, phenyl or benzyl group, which gives the compounds of general formula:

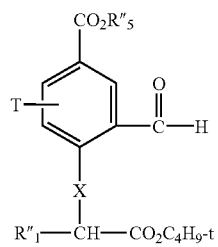
(42)

in which R″₁, R″₅, T and X have the same meaning as above, c) this ester of formula (42) is treated with formic acid or trifluoroacetic acid, which gives the acids of general formula:

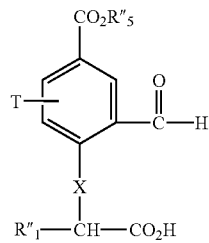
(43)

in which R″₁, R″₅, T and X have the same meaning as above, d) this compound is cyclized in the presence of benzenesulfonyl or of p-toluenesulfonyl chloride and of an acid acceptor, such as triethylamine, which gives the desired compounds of formula (6).

B—The compounds of formula (6) in which R″ represents the cyano group located at position 5, and R′₁, located at position 2, represents a $C_1$–$C_6$ alkyl, $C_3$–$C_6$ cycloalkyl, phenyl or benzyl group, can be prepared as follows:

a) first a formyl derivative of general formula:

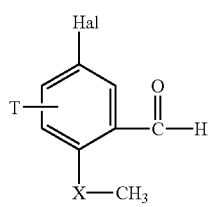
(44)

in which Hal, T and X have the same meaning as above, is treated with zinc cyanide in the presence of a suitable catalyst, for example a palladium derivative, such as tetrakis (triphenylphosphine)palladium, which gives the compounds of general formula:

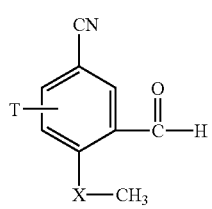
(45)

in which T and X have the same meaning as above, b) this compound of formula (45) is subsequently demethylated with lithium chloride, which gives the compound of general formula:

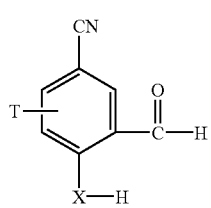
(46)

in which T and X have the same meaning as above, c) this compound of formula (46) is then treated with an ester of general formula:

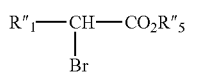
(47)

in which R"$_1$, and R"$_5$ have the same meaning as above, in the presence of a basic agent, such as an alkali metal carbonate, which gives the compounds of general formula:

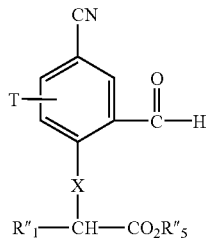

(48)

in which R"$_1$, R"$_5$ T and X have the same meaning as above, d) and e) this ester of formula (48) is saponified in the presence of a basic agent, such as an alkali metal hydroxide, and the acid thus obtained is cyclized in the presence of benzenesulfonyl or p-toluenesulfonyl chloride and of an acid acceptor, such as triethylamine, which gives the desired compounds.

C—The compounds of formula (6) in which R" represents a cyano or —CO$_2$R"$_5$ group located at position 5, and R'$_1$, located at position 2, represents a group (m) in which R$_{11}$ represents a —CO$_2$R"$_5$ group, can be obtained according to the sequence of stages below:

a) either, a cyano derivative of general formula:

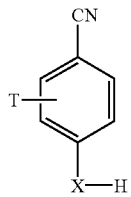

(49)

in which T and X have the same meaning as above is treated with iodine in the presence of aqueous ammonia, to form an iodo derivative of general formula:

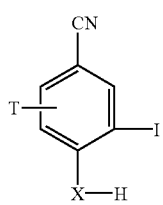

(50)

in which T and X have the same meaning as above, or, a compound of general formula:

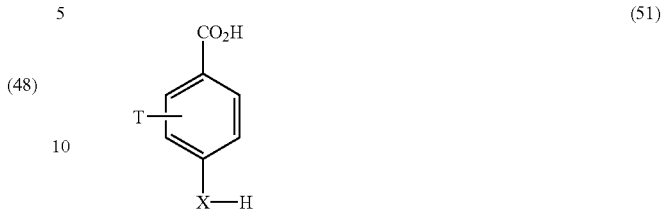

(51)

in which T and X have the same meaning as above, is first treated with an alkali metal iodide and an oxidizing agent, such as an alkali metal hypochlorite, for example sodium hypochlorite, then with a halogenating agent, such as thionyl chloride, and finally with an alcohol of general formula:

(52)

in which R"$_5$ has the same meaning as above, which gives an iodo derivative of general formula:

(53)

in which R"$_5$, T and X have the same meaning as above, b) the iodinated derivative of formula (50) or (53) is reacted with an acetylenic ester of general formula:

(54)

in which R"$_5$ and p have the same meaning as above, in the presence of a suitable catalyst, such as a palladium derivative, for example dichlorobis(triphenylphosphine)palladium, and of cuprous iodide, and in the presence of tetramethylguanidine, which gives the desired compounds of formula (6).

D—Alternatively, the compounds of formula (6) in which R" represents a cyano or —CO$_2$R"$_5$ group located at position 5, and R'$_1$, located at position 2, represents a C$_3$–C$_6$ alkyl group, can be prepared by reacting an iodinated derivative of formula (53) with an acetylenic derivative of general formula:

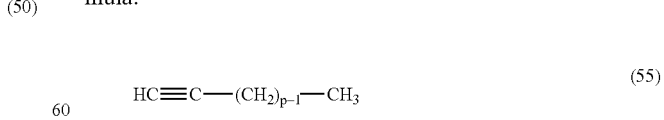

(55)

in which p has the same meaning as above, and in the presence of a suitable catalyst, such as a palladium derivative, for example tetrakis(triphenylphosphine)-palladium, and of cuprous iodide, which gives the desired compounds of formula (6).

E—The compounds of formula (6) in which R″ represents a cyano or —CO$_2$R″$_5$ group located at position 6, and R′$_1$, located at position 2, has the same meaning as above, can be obtained as follows:

a) a compound of general formula:

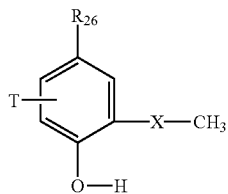

(56)

in which R$_{26}$, T and X have the same meaning as above is reacted with trifluoromethanesulfonic acid anhydride, in the presence of pyridine, to produce a compound of general formula:

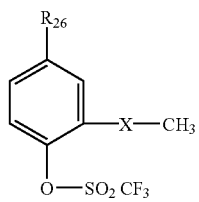

(57)

in which R$_{26}$, T and X have the same meaning as above, b) the compound thus formed is reacted with an acetylenic derivative of general formula:

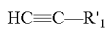

HC≡C—R′$_1$ (58)

in which R′$_1$ has the same meaning as above, in the presence of a suitable catalyst, for example a palladium derivative, such as dichlorobis(triphenyl-phosphine)palladium, and of an acid acceptor, such as triethylamine, to form the compounds of general formula:

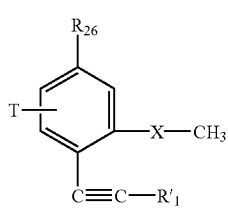

(59)

in which R′$_1$, R$_{26}$, T and X have the same meaning as above, c) this compound of formula (59) is then cyclized in the presence of boron tribromide at a temperature of less than −50° C., which gives the heterocyclic compounds of general formula:

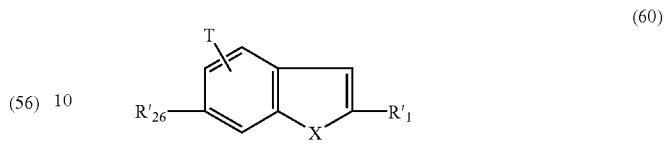

(60)

in which R′$_1$, T and X have the same meaning as above and R′$_{26}$ represents the cyano group, which gives desired compounds of formula (6), or R′$_{26}$ represents a carboxylic group, which gives an acid, d) this acid is esterified with an alcohol of formula (52), which gives desired compounds of formula (6).

F—The compounds of formula (6) in which R″ represents a cyano or —CO$_2$R″$_5$ group located at position 4, and R′$_1$, located at position 2, has the same meaning as above, can be obtained as follows:

a) a compound of general formula:

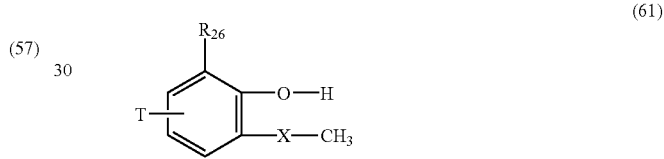

(61)

in which R$_{26}$, T and X have the same meaning as above, is reacted with trifluoromethanesulfonic anhydride, in the presence of pyridine, to produce a compound of general formula:

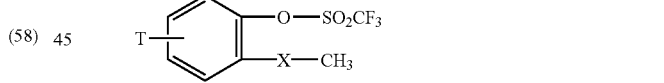

(62)

in which R$_{26}$, T and X have the same meaning as above, b) the compound thus formed is reacted with an acetylenic derivative of formula (58), in the presence of a suitable catalyst, such as a palladium derivative, for example dichlorobis(triphenylphosphine)palladium, and of an acid acceptor, such as triethylamine, to form the compounds of general formula:

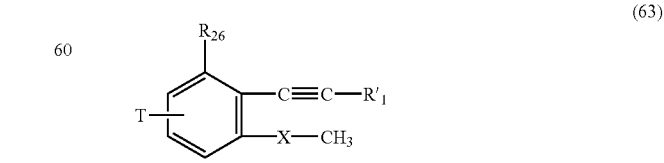

(63)

in which R′$_1$, R$_{26}$, T and X have the same meaning as above, c) this compound of formula (63) is then cyclized in the presence of boron tribromide, which gives the heterocyclic compounds of general formula:

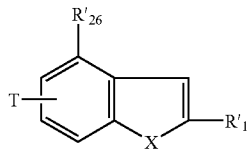

in which R'$_1$, T and X have the same meaning as above and R'$_{26}$ represents the cyano group, which gives the desired compounds of formula (6), or R'$_{26}$ represents a carboxylic group, which gives an acid, d) this acid is esterified with an alcohol of formula (52), which gives desired compounds of formula (6).

G—The compounds of formula (6) in which R" represents a cyano or —CO$_2$R"$_5$ group located at position 7, and R'$_1$, located at position 2, has the same meaning as above, can be obtained as follows:

a) an alcohol of general formula:

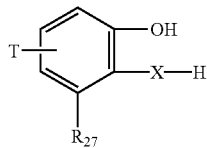

in which R$_{27}$ represents a cyano or formyl group and T and X have the same meaning as above, is treated with methyl iodide, in the presence of an alkali metal hydride, to give a compound of general formula:

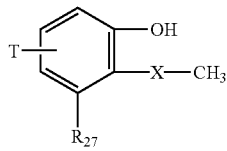

in which R$_{27}$, T and X have the same meaning as above, b) the compound thus formed is reacted with trifluoromethanesulfonic anhydride, to give a compound of general formula:

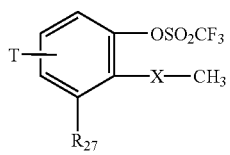

in which R$_{27}$, T and X have the same meaning as above, c) the compound thus formed is treated with a compound of formula (58), in the presence of a suitable catalyst, such as a palladium derivative, for example dichlorobis(triphenylphosphine)palladium, which produces a compound of general formula:

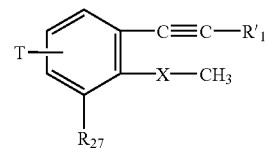

in which R'$_1$, R$_{27}$, T and X have the same meaning as above, d) the compound of formula (68) thus formed is subsequently reacted:

when R$_{27}$ represents the cyano group, with lithium chloride, to form the desired compounds of formula (6) in which R" represents the cyano group, when R$_{27}$ represents the formyl group, with an alkali metal cyanide in the presence of manganous oxide and acetic acid, to give a compound of general formula:

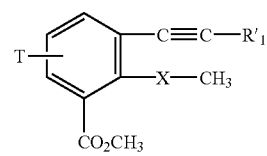

in which R$_{27}$, T and X have the same meaning as above, which is cyclized with lithium chloride, to give a mixture of ester and of acid of general formula:

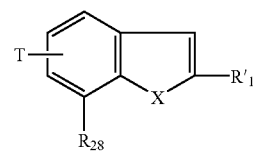

in which R$_{28}$ represents the methoxycarbonyl or carboxylic group and R'$_1$, T and X have the same meaning as above, which mixture is treated with methanol in the presence of a strong acid, such as sulfuric acid, which gives desired compounds of formula (6) in which R" represents the methoxycarbonyl group.

The other compounds of formula (6), that is to say the compounds of formula (6) in which R", located at position 7, represents a —CO$_2$R"$_5$ group, with the exception of the methoxycarbonyl group, can be obtained by saponifying an ester of formula (6) in which R", located at position 7, represents the methoxycarbonyl group, in the presence of a basic agent, such as an alkali metal hydroxide, to give a salt, which is acidified with a strong acid, such as hydrochloric acid, to give a 7-carboxybenzofuran derivative, which is esterified with an alcohol of general formula:

R'$_a$—OH (71)

in which R'$_a$ represents a C$_2$–C$_{10}$ alkyl or C$_3$–C$_6$ cycloalkyl radical, which gives desired compounds of formula (6).

H—The compounds of formula (6) in which R" represents the group (k) can be obtained by cyclizing a compound of formula (6) in which R" represents a —$CO_2R"_5$ group, by means of acetamide oxime, in the presence of an alkali metal hydride, such as sodium hydride, which gives the desired compounds.

I—The compounds of formula (6) in which R" represents an $R_4$—O—N≡CH— group in fact correspond to the compounds of formula (38), the preparation of which was described above.

Most of the other starting compounds or intermediate compounds involved in the various processes described above are known compounds or compounds which can be prepared by known methods.

For example, some of the amines of formula (3) or formula (5) are known and described in particular in U.S. Pat. No. 4,831,054 or EP 471609, or can be prepared by the methods described therein.

For example, 1-(2-chloroethyl)-4-dicyclohexylmethylpiperazine can be prepared by reacting N-dicyclohexylmethylpiperazine with ethylene oxide, to form 1-(2-hydroxyethyl)-4-dicyclohexylmethylpiperazine, which is subsequently treated with a chlorinating agent, such as thionyl chloride, to produce the desired compound.

Likewise, 1-(2-chloroethyl)-3,5-diethylpiperidine can be produced by a similar process involving the formation of 1-(2-hydroxyethyl)-3,5-diethylpiperidine from ethylene oxide and 2,5-diethylpiperidine, and then the conversion thereof using a halogenating agent, such as thionyl chloride, to produce the desired compound.

Benzofuran or benzothiophene derivatives which comprise a monoalkylamino- or dialkylaminoalkoxybenzoyl chain and which are substituted on the homocycle with an amino group, which itself may or may not be substituted, are already known. Such compounds, which have been disclosed in patent EP 0471609, have been shown to possess advantageous antiarrhythmia properties resulting in particular in pharmacological effects of Vaughan-Williams classes 1, 2, 3 and 4.

However, these benzofuran and benzothiophene derivatives exhibit low solubility in aqueous medium and low availability when administered orally.

In point of fact, it has now been discovered, in the context of the invention, that benzofuran or benzothiphene derivatives comprising an aminoalkoxybenzoyl chain and other groups attached to the heterocycle via a carbon atom exhibit a pharmacological profile similar to that of the prior compounds, while at the same time offering better metabolic stability, higher solubility and greater bioavailability when administered orally.

The results of pharmacological tests carried out for the purpose of determining the properties of the compounds of the invention with respect to the cardiovascular system are listed below.

I. Antiarrhythmic Activity

The aim of this test is to determine the ability of the compounds of the invention to provide protection against reperfusion-induced arrhythmias. To this end, use was made of the method reported by A. S. Manning et al. in Circ. Res. 1984, 55: 545–548 modified as follows:

Rats, divided into batches, are first anesthetized with sodium pentobarbital (60 mg/kg intraperitoneally), and are then intubated and maintained under assisted respiration.

A cannula for intravenous administration is subsequently inserted into their right jugular vein, an intravenous dose of the compound to be studied is administered and, 5 minutes later, a ligature loop is placed around the left anterior descending coronary artery in the immediate proximity of its origin. This artery is then occluded for 5 minutes by pulling on the ends of the ligature, so as to induce reperfusion by relaxing the tension.

The arrhythmias induced by this reperfusion are then evaluated.

A similar test is carried out with oral administration. In this case, the compound to be studied is administered 120 minutes before ligating the left anterior descending coronary artery.

The results of these tests showed that the compounds of the invention protect the treated animals in a significant manner, ranging up to 100% at doses of between 0.3 and 10 mg/kg intraveously and 10 to 90 mg/kg orally.

II. Antiadrenergic Properties

The aim of this test is to determine the ability of the compounds of the invention to reduce the increase in blood pressure induced by phenylephrine (anti-α effect) and the acceleration in heart rate induced by isoprenaline (anti-β effect) in dogs anesthetized beforehand with pentobarbital and chloralose.

For each dog, the dose of phenylephrine (5 or 10 µg/kg) which leads to an increase in arterial pressure of between 25 and 40 mm Hg and the dose of isoprenaline (0.9 or 1 µg/kg) which should lead to an increase in heart rate of between 60 and 120 beats/minute are first determined.

The doses of phenylephrine and of isoprenaline thus determined are injected alternately every 10 minutes and, after obtaining 2 successive reference responses, a dose of the compound to be studied is administered intravenously.

Anti-α Effect

The percentage reduction, by the compound of the invention, of the induced hypertension, compared to the reference hypertension obtained before injection of this compound (approximately 100 mm Hg), is recorded.

Anti-β Effect

The percentage reduction, by the compound to be studied, of the induced acceleration in heart rate is recorded.

The results of these tests show that, at doses varying from 1 to 10 mg/kg, the compounds of the invention exhibit anti-α and/or anti-β effects which result in reductions, ranging from 50% to virtually 100%, in the induced hypertension and/or in the induced increase in heart rate.

III. Atrial Fibrillation

The aim of this test is to evaluate the effectiveness of the compounds of the invention with respect to atrial fibrillation induced by permanent stimulation of the vagus nerve in dogs anesthetized according to the method described in Circulation 1993; 88: 1030–1044.

The compounds to be studied are administered at the cumulative doses of 3 and 10 mg/kg in slow intravenous infusions of 10 minutes during an episode of sustained atrial fibrillation.

At the dose of 10 mg/kg, the compounds of the invention generally convert 100% of the atrial fibrillations into a sinus rhythm and prevent the reinduction thereof in 50 to 100% of cases. At this dose, significant increases in the heart period and in the atrial effective refractory periods for various basal values of the heart period are observed.

IV. Inhibitory Effects on the Neurohormonal System

The aim of this test is to search for inhibitory effects of the compounds of the invention with respect to vasoconstrictive effects induced by various peptides such as noradrenaline (NA), angiotensin II (A-II), arginine vasopressin (AVP), neuropeptide Y (NPY) and endothelin (ET), and also with respect to tachycardic effects induced by isoprenalin (Iso), in conscious rats.

An arterial catheter (right carotid artery), for measuring the arterial pressure, and a venous catheter (right jugular vein), for injecting the product to be studied, are implanted, 24 hours before the test, in male Sprague Dawley rats weighing approximately 300 g. On the following day, the rats are placed in cylindrical cages and the arterial catheter is connected to a pressure sensor via a revolving joint on a pendulum. This pressure sensor is itself connected to a polygraph for recording the arterial pressure.

The action of the compounds of the invention, administered intravenously, is then investigated with respect to vasoconstrictive effects induced by NA (1 µg/kg), A-II (100 µg/kg) and AVP (40 µg/kg) at the respective doses of either 3, 10 and 30 mg/kg or 1.3 to 10 mg/kg, and solely at the dose of 10 mg/kg with respect to vasoconstrictive effects induced by NPY (6 µg/kg) and ET (0.5 µg/kg), or tachycardic effects induced by Iso (1 µg/kg).

First, the various peptide agonists are solubilized in 0.9% physiological saline and the compound to be studied is solubilized in a suitable solvent. These peptides are subsequently injected as a bolus in a volume of 0.05 ml/kg, 30 and 10 minutes before intravenous administration of 0.1 ml/kg of a solution of the compound to be studied or of solvent. These peptide injections are subsequently repeated 10, 30, 60 and 120 minutes after administration of the compound to be studied. Depending on the duration of action of the compound to be tested, these injections can optionally be repeated every 30 minutes without ever exceeding 5 hours in total.

The variations in arterial pressure after administration of a given peptide are then evaluated by measuring, at various times, the difference between the maximum effect induced by the peptide angonist and the basal value of the arterial pressure. The results obtained show that NA, A-II, AVP, NPY and ET induce respective increases in the arterial pressure of 45±3, 40±3, 30±2 and 34±4 mmHg, and Iso induces an increase in the heart rate of 209±7 beats per minute.

In addition, it is observed that the compounds of the invention antagonize in a dose-dependent manner the vasoconstrictive effects induced by NA, A-II and AVP. They also antagonize the effects induced by NPY and ET, and the increase in heart rate induced by Iso. At the highest doses, the maximum inhibition obtained after 15 minutes ranges between 40 and 80% and the duration of action is at least greater than or equal to 30 minutes.

V. Toxicity

The toxicity of the compounds of the invention has proved to be compatible with their therapeutic use.

The pharmaceutical compositions according to the invention can be provided in any form suitable for administration in human or veterinary therapy. For example, the pharmaceutical compositions of the present invention can be formulated for oral, sublingual, subcutaneous, intramuscular, intravenous, transdermal or rectal administration. As regards the administration unit, this can take the form, for example, of a tablet, a sugar-coated tablet, a capsule, a hard gelatin capsule, a powder, a suspension, a syrup or granules for oral administration, of a suppository for rectal administration or of a solution or suspension for parenteral administration.

The pharmaceutical compositions of the invention may comprise, per administration unit, for example, from 50 to 500 mg by weight of active ingredient for oral administration, from 50 to 200 mg of active ingredient for rectal administration and from 50 to 150 mg of active ingredient for parenteral administration.

Depending on the route of administration chosen, the pharmaceutical or veterinary compositions of the invention will be prepared by combining at least one of the compounds of formula (1), or a pharmaceutically acceptable salt of this compound, with a suitable excipient, the latter possibly consisting, for example, of at least one ingredient selected from the following substances: lactose, starches, talc, magnesium stearate, polyvinylpyrrolidone, alginic acid, colloidal silica, distilled water, benzyl alcohol or sweetening agents.

When the compositions are tablets, these tablets can be treated such that they exhibit sustained or delayed activity and that they continually release a predetermined amount of active principle.

The following nonlimiting examples illustrate the preparation of the compounds and compositions of the invention:

EXAMPLE 1

Methyl 2-butyl-3-[4-[3-dibutylaminopropoxy]benzoyl]-1-benzofuran-5-carboxylate

A. Methyl 3-formyl-4-hydroxybenzoate 2 g of phosphoric anhydride and 40 ml of methanesulfonic acid are placed in a three-necked round-bottomed flask. The mixture is heated to approximately 85° C., the heating is then stopped and an intimate mixture of 7.6 g (0.05 mol) of methyl 4-hydroxybenzoate and of 10.22 g (0.073 mol) of hexamethylenetetramine is added in fractions, at a temperature of 85° C. to 90° C.

Once the addition has been completed, the mixture is heated at 85°/90° C. for 2 hours and allowed to cool to 70° C., and then 60 ml of water are added. The mixture is allowed to gradually return to ambient temperature, and then extracted with ethyl acetate. It is then washed with water, an aqueous sodium bicarbonate solution, water, a potassium acid sulfate solution, again with water to neutrality and, finally, with a saturated sodium chloride solution.

In this way, 6.73 g of desired compound are obtained in the crude form.

Yield: 75% M.p.: 80–81° C.

B. tert-Butyl 2-bromohexanoate 25.16 g (0.129 mol) of 2-bromohexanoic acid are dissolved in 200 ml of benzene containing 1 ml of N,N-dimethylformamide. The solution is cooled by means of a water/ice mixture and 32.8 g (2 equivalents) of oxalyl chloride in 50 ml of benzene are added dropwise at a temperature of approximately 7° C. The mixture is stirred for 1 hour under cold conditions and then allowed to return to ambient temperature. The solvent is evaporated off. The acid chloride obtained is then dissolved in 500 ml of dichloromethane, and is then added, at a temperature of less than 10° C., to a mixture of 120 g (12.5 equivalents) of tert-butanol and of 24.9 g (1.75 equivalent) of triethylamine.

The mixture is allowed to return to ambient temperature and is washed with 500 ml of water and then with 100 ml of 3% hydrochloric acid. The dichloromethane is evaporated off and the residue is then taken up with diethyl ether and washed with water, an aqueous sodium bicarbonate solution, water, a potassium sulfate solution, water and, finally, with a saturated sodium chloride solution. Distillation is then carried out under reduced pressure.

In this way, 25 g of desired compound is obtained.

Yield: 77% B.p.: 104–107° C. (20 mmHg)

C. tert-Butyl 2-[(2-formyl-4-methoxycarbonyl)phenoxy]hexanoate 6.73 g (37 mmol) of methyl 3-formyl-4-hydroxybenzoate and 10.32 g (1.1 equivalent) of tert-butyl 2-bromohexanoate are dissolved in 100 ml of N,N-dimethylformamide.

6.45 g (1.25 equivalent) of potassium carbonate are then added and the mixture is heated in a water bath (approximately at 80° C.) for 3 hours. The N,N-dimethylformamide is then evaporated off. The residue is taken up with ethyl acetate and washed with a 3% solution of potassium acid sulfate, with water and with a saturated sodium chloride solution. Purification is carried out by chromatography on silica (eluent: 100/2 dichloromethane/ethyl acetate).

In this way, 11.4 g of desired compound are obtained.

Yield: 88%

D. 2-[(2-Formyl-4-methoxycarbonyl)phenoxy]hexanoic acid

A mixture of 17.16 g of tert-butyl 2-[(2-formyl-4-methoxycarbonyl)phenoxy]hexanoate and 100 ml of formic acid are stirred at ambient temperature for 24 hours. The mixture is then diluted with water and extracted with ethyl acetate. Washing is carried out with water until a neutral pH is obtained, and then with a saturated sodium chloride solution.

In this way, 14.7 g of desired compound are obtained.

Yield: 100%

E. Methyl 2-butyl-1-benzofuran-5-carboxylate 52.5 ml of benzenesulfonyl chloride dissolved in 250 ml of toluene are added to a mixture of 141.6 ml of triethylamine in 250 ml of toluene. Heating is carried out at 80° C. and then 85.3 g of 2-[(2-formyl-4-methoxycarbonyl)phenoxy]hexanoic acid dissolved in 500 ml of toluene are added, dropwise, at a temperature of less than or equal to 90° C.

Once the addition has been completed, the heating is continued for 0.5 hour, and the mixture is allowed to return to ambient temperature and is diluted with ethyl acetate. Washing is then carried out with water, a potassium acid sulfate solution, water, a sodium bicarbonate solution, water and a saturated sodium chloride solution. Distillation is then carried out under reduced pressure.

In this way, 28.4 g of desired compound are obtained.

Yield: 39% relative to the methyl 4-hydroxybenzoate B.p.: 126–132° C. (0.03 mbar)

F. Methyl 2-butyl-3-(4-methoxybenzoyl)-1-benzofuran-5-carboxylate

Under argon, 45.6 g (0.28 mol) of ferric chloride are dissolved in 270 ml of dichloroethane and then 32.51 g (0.14 mol) of methyl 2-butyl-1-benzofuran-5-carboxylate dissolved in 180 ml of dichloroethane are added at approximately 10° C. 48.2 g (0.28 mol) of anisoyl chloride dissolved in 180 ml of dichloroethane are subsequently added, at between 10 and 15° C. The mixture is allowed to return to ambient temperature and then stirred for 5 hours at this temperature. The reaction mixture is poured onto an ice/water mixture and the precipitate is then filtered off.

The filtrate is separated by settling, and the aqueous phase is extracted with dichloromethane. The organic phases are washed with a sodium bicarbonate solution, water and a saturated sodium chloride solution, and then purification is carried out by crystallization.

In this way, 48.84 g of desired compound are obtained.

Yield: 95% M.p.: 75–78° C.

G. Methyl 2-butyl-3-(4-hydroxybenzoyl)-1-benzofuran-5-carboxylate 48.84 g of methyl 2-butyl-3-(4-methoxybenzoyl)-1-benzofuran-5-carboxylate and 55 g of aluminum chloride are dissolved in 550 ml of toluene. Heating is carried out at 60° C., in a water bath, for 2 hours and then toluene is separated off by settling.

The residue is dissolved in tetrahydrofuran, ice is added and the mixture is stirred for 2 hours. Separation is carried out by settling and the aqueous phase is extracted with ethyl acetate. The 3 organic phases are pooled and washing is carried out with water and then with a saturated aqueous sodium chloride solution. Purification is then carried out by crystallization from diisopropyl ether.

In this way, 26.45 g of desired compound are obtained.

Yield: 56% M.p.: 152–153° C.

H. Methyl 2-butyl-3-[4-(3-dibutylamino)propoxy]-benzoyl]-1-benzofuran-5-carboxylate 2.14 g (6 mmol) of methyl 2-butyl-3-(4-hydroxybenzoyl)-1-benzofuran-5-carboxylate, 1.25 g (6 mmol) of 3-chloro-1-(dibutylamino)propane and 1 g of potassium carbonate are dissolved in 35 ml of methyl ethyl ketone. The mixture is brought to reflux for 22 hours, dilution is performed with water and extraction is carried out with ethyl acetate. Washing is carried out with a saturated sodium chloride solution and purification is carried out by chromatography on silica (eluent: 5/5 hexane/ethyl acetate).

In this way, 2.95 g of desired compound are obtained in the free base form.

Yield: 94%

Nuclear magnetic resonance (NMR) spectrum: standard

EXAMPLE 2

Methyl 2-butyl-3-[4-[3-(dibutylamino)propoxy]benzoyl]-1-benzofuran-5-carboxylate oxalate 1.957 g of methyl 2-butyl-3-[4-[3-(dibutylamino)propoxy]benzoyl]-1-benzofuran-5-carboxylate and 0.338 g (1 equivalent) of oxalic acid are dissolved in methanol.

Evaporation is carried out, the residue is taken up in diethyl ether, and trituration then evaporation are performed. Drying is subsequently carried out under vacuum.

In this way, 2.13 g of desired compound are obtained.

Yield: 93% M.p.: 82–84° C.

NMR spectrum: standard

The following compound was prepared by following the same process as above (Example 1 and Example 2):

Methyl 2-butyl-6-methyl-3-[4-[3-(1-piperidinyl) propoxy]benzoyl]-1-benzofuran-5-carboxylate hydrochloride (Example 3).

M.p.: 181–183° C. (diethyl ether) NMR spectrum: standard

EXAMPLE 4

Cyclohexyl 2-butyl-3-[4-[3-(dibutylamino)propoxy] benzoyl]-1-benzofuran-5-carboxylate oxalate A mixture of 3.25 g of 2-butyl-3-[4-[3-(dibutylamino) propoxy]benzoyl]-1-benzofuran-5-carboxylic acid and 3 ml of thionyl chloride in 60 ml of chloroform is brought to reflux for 1 hour. It is concentrated to dryness and then successive operations of taking up in diethyl ether and concentrating are carried out, which gives an acyl chloride, which is subsequently used in crude form. 50 ml of cyclohexanol are then added and heating is carried out at 100° C. for 2 hours. After cooling, distillation is carried out under vacuum in order to remove the cyclohexanol. The nondissolved fraction is chromatographed on silica (eluent: chloromethane/methanol: 98/2) and the main fraction is taken up in a dilute aqueous solution of sodium carbonate. Extraction with diethyl ether, drying and concentrating are carried out, which makes it possible to obtain the desired product in the free base form, which is salified by adding oxalic acid in absolute ethanol.

In this way, 2.203 g of desired compound are recovered. Yield: 50.6% M.p.: 96° C. NMR spectrum: standard

EXAMPLE 5

2-Butyl-3-[4-[3-(dibutylamino)propoxy]benzoyl]-N-hydroxy-1-benzofuran-5-carboxamide oxalate A. 2-Butyl-3-[4-[3-(dibutylamino)propoxy]benzoyl]-N-benzyloxy-1-benzofuran-5-carboxamide 2.45 g of 2-butyl-3-[4-[3-(dibutylamino)propoxy]benzoyl]-1-benzofuran-5-carboxylic acid, 0.855 g (1.1 equivalent) of benzyloxyamine hydrochloride, 2.36 g (1.1 equivalent) of BOP and 2 ml (approximately 3 equivalents) of triethylamine are reacted in 70 ml of dichloromethane. The mixture is stirred for 1 hour at room temperature and evaporated, and the residue is taken up in ethyl acetate. The extracts are then washed with water, a potassium acid sulfate solution, water, a sodium bicarbonate solution, water until a neutral pH is obtained, and then with a saturated sodium chloride solution.

In this way, approximately 3 g of crude desired compound are obtained.

B. 2-Butyl-3-[4-[3-(dibutylamino)propoxy]benzoyl]-N-hydroxy-1-benzofuran-5-carboxamide oxalate 3.24 g of 2-butyl-3-[4-[3-(dibutylamino)propoxy]benzoyl]-N-benzyloxy-1-benzofuran-5-carboxamide in 100 ml of methanol are hydrogenated in the presence of 5% palladium charcoal, at ambient temperature and at normal pressure. Filtration over diatomaceous earth and evaporation are carried out. Purification is then carried out by chromatography on silica (eluent: 90/10/0.5 dichloromethane/methanol/aqueous ammonia), which gives 1.82 g (yield: 66%) of the desired product in the base form.

1.565 g of the base thus obtained are subsequently introduced into a solution of 0.270 g of oxalic acid in methanol. Evaporation is carried out, the residue is taken up with diethyl ether, and this is allowed to crystallize.

In this way, the desired compound is obtained in the form of an amorphous powder.

NMR spectrum: standard

EXAMPLE 6

Methyl 2-butyl-3-[4-[3-[(2,2-dimethylpropyl)amino] propoxy]benzoyl]-1-benzofuran-5-carboxylate 16.73 g of methyl 2-butyl-3-[4-(3-bromopropoxy)benzoyl]-1-benzofuran-5-carboxylate, 15.52 g (5 equivalents) of neopentylamine and 19.7 g of potassium carbonate are introduced into 200 ml of dimethyl sulfoxide.

The mixture is stirred at ambient temperature for 18 hours, evaporation is carried out, the residue is taken up in water, and extraction is carried out with ethyl acetate. Washing is subsequently carried out twice with water and then with a saturated sodium chloride solution. Purification is then carried out by chromatography on silica (eluent: 95/5 dichloromethane/methanol) and crystallization from heptane is allowed to take place.

In this way, 10.6 g of desired compound are obtained.

Yield: 62.5% M.p.: 61–63° C. NMR spectrum: standard

EXAMPLE 7

2-Butyl-3-[4-[3-(dibutylamino)propoxy]benzoyl]-N, N-diethyl-1-benzofuran-5-carboxamide oxalate 2.27 g of 2-butyl-3-[4-[3-(dibutylamino)propoxy]benzoyl]-1-benzofuran-5-carboxylic acid and 2.5 ml of thionyl chloride are introduced into 50 ml of chloroform.

The mixture is brought to reflux for 1 hour and evaporation is carried out. The residue is taken up in diethyl ether and evaporation is carried out twice. The residue is subsequently dissolved in 50 ml of dichloromethane and 1.61 g of N,N-diethylamine dissolved in 10 ml of dichloromethane are added.

Evaporation is carried out, the residue is taken up in a potassium carbonate solution and extraction is then carried out with diethyl ether. Washing is subsequently carried out with water and a saturated sodium chloride solution and purification is carried out by chromatography on silica (eluent: 95/5 dichloromethane/methanol), which gives 1.65 g (yield: 66%) of desired compound in the free base form. 1.62 g of the base thus obtained and 0.259 g of oxalic acid are subsequently dissolved in methanol, and then evaporation is carried out. The residue is taken up in diethyl ether and crystallization is allowed to take place. Filtration, washing with diethyl ether and drying under vacuum are carried out.

In this way, 1.54 g of desired compound are obtained in the form of a solid.

NMR spectrum: standard

EXAMPLE 8

[2-(Dimethylamino)ethanol]2-butyl-3-[4-[3-(dibutylamino)propoxy]benzoyl]-1-benzofuran-5-carboxylate oxalate Under a nitrogen atmosphere, 1.93 g (3.8 mmol) of 2-butyl-3-[4-[3-(dibutylamino)propoxy]benzoyl]-1-benzofuran-5-carboxylic acid and 0.615 g of carbonyldiimidazole are mixed in 20 ml of N,N-dimethylformamide. The reaction medium is heated at 40° C. for 1 hour, and then 0.583 g of 1,8-diazabicyclo-[5.4.0]undec-7-ene, followed by 0.678 g (7.60 mmol) of 2-(dimethylamino)ethanol, are added. The mixture is maintained at 40° C. for 18 hours and is then concentrated to dryness. Extraction is subsequently carried out with ethyl acetate, the extract is washed with water and a saturated sodium chloride solution and purification is carried out by chromatography on silica (eluent: 90/10 dichloromethane/methanol), to produce 1.47 g of desired product in the base form, which base is then treated with a solution of oxalic acid in absolute ethanol.

In this way, 1.122 g of desired compound are recovered in the form of an amorphous solid.

Yield: 66.8% NMR spectrum: standard

EXAMPLE 9

Methyl 3-{[(2-butyl-3-{4-[3-(dibutylamino)propoxy]benzoyl}-1-benzofuran-5-yl)carbonyl]amino}propanoate 2.54 g (5 mmol) of 2-butyl-3-[4-[3-(dibutylamino)propoxy]benzoyl]-1-benzofuran-5-carboxylic acid, 0.768 g (5.5 mmol) of 2-(methoxycarbonyl)ethylamine hydrochloride, 2.3 ml (16.5 mmol) of triethylamine and 2.43 g (5.5 mmol) of BOP are introduced into 50 ml of dichloromethane containing 15 ml of N,N-dimethylformamide. The reaction medium is stirred at ambient temperature for 2 hours, evaporation is carried out and the residue is extracted with ethyl acetate. Washing is then carried out with water, a potassium acid sulfate solution, water, a sodium bicarbonate solution, water until a neutral pH is obtained, and a saturated sodium chloride solution. Purification is subsequently carried out by chromatography on silica (eluent: 100/3 dichloromethane/methanol).

In this way, 2.1 g of desired compound are obtained.
Yield: 71% NMR spectrum: standard

EXAMPLE 10

3-{[(2-Butyl-3-{4-[3-(dibutylamino)propoxy]benzoyl}-1-benzofuran-5-yl)carbonyl]amino}propionic acid 2 g of methyl 3-{[(2-butyl-3-{4-[3-(dibutylamino)propoxy]benzoyl}-1-benzofuran-5-yl)-carbonyl]amino}propanoate and 0.270 g (2 equivalents) of sodium hydroxide are introduced into a mixture of 50 ml of dioxane, then 10 ml of methanol and 10 ml of water. The mixture is stirred for 2 hours at ambient temperature, evaporation is carried out, and then the residue is taken up in water. Acidification with dilute hydrochloric acid, until a pH of approximately 5 is obtained, extraction with dichloromethane and washing with a saturated sodium chloride solution are then carried out. Purification is subsequently carried out by chromatography on silica (eluent: 100/7 dichloromethane/methanol).

In this way, 1.55 g of desired compound are obtained in the form of an amorphous solid.

Yield: 79% NMR spectrum: standard

EXAMPLE 11

2-Butyl-3-[4-[3-(dibutylamino)propoxy]benzoyl]-1-benzofuran-5-carboxamide 3.5 g of 2-butyl-3-[4-[3-dibutylamino)propoxy]benzoyl]-5-cyano-1-benzofuran are mixed in 35 ml of concentrated sulfuric acid.

The reaction medium is stirred at ambient temperature for 24 hours and is then poured onto ice. Basification, under cold conditions, with sodium hydroxide and extraction with dichloromethane are carried out. Washing with a saturated sodium chloride solution and purification by crystallization from heptane are then carried out.

In this way, 2.68 g of desired compound are obtained.
Yield: 74% M.p.: 90–92° C. NMR spectrum: standard

EXAMPLE 12

2-Butyl-3-[4-[3-(dibutylamino)propoxy]benzoyl]-5-(1H-tetrazol-5-yl)-1-benzofuran 3.26 g of 2-butyl-3-[4-[3-(dibutylamino)propoxy]benzoyl]-5-cyano-1-benzofuran and 4.5 g (approximately 2 equivalents) of tributyltin azide are introduced into 80 ml of toluene. The mixture is refluxed for 90 hours, the solvent is evaporated off and the residue is chromatographed on silica (eluent: 92/8 dichloromethane/methanol). Crystallization from diisopropyl ether is subsequently allowed to take place.

In this way, 3.05 g of desired compound are obtained.
Yield: 86% M.p.: 145–147° C. NMR spectrum: standard

EXAMPLE 13

2-Butyl-3-[4-[3-(dibutylamino)propoxy]benzoyl]-1-benzofuran-5-carbohydrazide 2.16 g (4.3 mmol) of 2-butyl-3-[4-[3-(dibutylamino)propoxy]benzoyl]-1-benzofuran-5-carboxylic acid and 2.5 ml of thionyl chloride are introduced into 50 ml of chloroform. The mixture is brought to reflux for 1 hour, and evaporation is carried out.

The residue is taken up in diethyl ether and the solvent is evaporated off. These two operations are repeated. The acyl chloride thus formed is taken up in 15 ml of tetrahydrofuran, and this solution is added dropwise to a solution of 1 ml of hydrazine hydrate at 98% in 15 ml of tetrahydrofuran. The reaction medium is stirred at ambient temperature and then evaporation is carried out. Extraction with ethyl acetate and washing with water are carried out. Purification is subsequently carried out by chromatography on silica (eluent: 85/5/0.2 dichloromethane/methanol/aqueous ammonia).

In this way, 1.13 g of desired compound are obtained.
Yield: 41% NMR spectrum: standard

EXAMPLE 14

5-(2-Butyl-3-[4-[3-(dibutylamino)propoxy]benzoyl]-1-benzofuran-6-yl)-1,3,4-oxadiazol-2-(3H)-one hydrochloride 1.13 g of 2-butyl-3-[4-[3-(dibutylamino)propoxy]benzoyl]-1-benzofuran-5-carbohyrazide are dissolved in 20 ml of chloroform and this solution is added dropwise to a solution of 2.2 g of phosgene in 30 ml of chloroform. The mixture is brought to reflux for 6 hours. After the mixture has returned to ambient temperature, washing is carried out first with water, until a neutral pH is obtained, and subsequently with a saturated sodium bicarbonate solution.

In this way, 0.535 g of desired compound is obtained after crystallization from diethyl ether.

Yield: 45% NMR spectrum: standard

EXAMPLE 15

2-Butyl-3-[4-[3-(dibutylamino)propoxy]benzoyl]-1-benzofuran-5-carbaldehyde (E)-O-methyloxime oxalate

A. 2-Butyl-5-hydroxymethylbenzofuran 2.32 g (0.01 mol) of methyl 2-butyl-1-benzofuran-5-carboxylate in 20 ml of diethyl ether are added dropwise to 0.400 g of lithium aluminum hydride in 20 ml of diethyl ether, and the mixture is then brought to the reflux temperature of ether.

Once the addition has been completed, the mixture is stirred for 1 hour at ambient temperature. The mixture is cooled in an ice/water mixture, hydrolysis is carried out by means of a 1N hydrochloric acid solution and separation is carried out by settling. Extraction with diethyl ether and washing with water and a saturated sodium chloride solution are carried out.

In this way, 1.92 g of desired compound are obtained.
Yield: 94%

B. 2-Butyl-1-benzofuran-5-carbaldehyde 3.17 g (0.025 mol) of oxalyl chloride in 50 ml of dichloromethane are cooled to −60° C., and 3.67 g (0.054 mol) of dimethyl sulfoxide in 20 ml of dichloromethane are then added. The mixture is stirred for 10 minutes and 3.43 g (17 mmol) of 2-butyl-5-hydroxymethyl-1-benzofuran in 50 ml of dichloromethane are then added. Stirring is carried out for 15 minutes, 15.7 ml (0.113 mol) of triethylamine are added and the mixture is allowed to return to ambient temperature. Water is added and separation is carried out by settling. Extraction is carried out with dichloromethane. Washing is then carried out with water, a potassium acid sulfate solution, until a neutral pH is obtained, with water, a sodium carbonate solution, water and, finally, with a saturated sodium chloride solution.

In this way, the desired compound is obtained, which is used in crude form.

C. 2-Butyl-1-benzofuran-5-carbaldehyde (E)-O-methyloxime 2.07 g of 2-butyl-1-benzofuran-5-carbaldehyde, 1.38 g of methoxyamine hydrochloride and 1.57 g of pyridine are added to 25 ml of methanol. The mixture is stirred for 1.5 hours at ambient temperature, evaporation is carried out and the residue is taken up in diethyl ether. Washing is carried out with water, a potassium acid sulfate solution, water and a saturated sodium chloride solution. Purification is subsequently carried out by chromatography on silica (eluent: 1/1 dichloromethane/heptane).

In this way, 1.96 g of desired compound are obtained.
Yield: 83%

D. 2-Butyl-3-[4-(3-bromopropoxy)benzoyl]-1-benzofuran-5-carbaldehyde (E)-O-methyloxime Under argon, 6.94 g (2 equivalents) of ferric chloride are introduced into 40 ml of dichloroethane. 4.91 g (21 mmol) of 2-butyl-1-benzofuran-5-carbaldehyde (E)-O-methyloxime dissolved in 25 ml of dichloroethane are then added, at around +10° C., and 11.89 g (2 equivalents) of 1-chlorocarbonyl-4-(3-bromopropoxy)benzene in 25 ml of dichloromethane are then introduced at between +10 and +15° C. The mixture is allowed to return to ambient temperature and is then stirred for 5 hours at ambient temperature. It is then poured onto an ice/water mixture, the precipitate is filtered off and the filtrate is separated out by settling. Purification is then carried out by chromatography on silica (eluent: dichloromethane).

In this way, the desired compound is obtained, that is to say 2.74 g of (E) isomer (yield: 27.5%) and 2.05 g of (Z) isomer.

M.p.: 78–81° C.

E. 2-Butyl-3-[4-[3-(dibutylamino)propoxy]benzoyl]-1-benzofuran-5-carbaldehyde (E)-O-methyloxime oxalate 2.3 g (5 mmol) of 2-butyl-3-[4-(3-bromopropoxy)benzoyl]-1-benzofuran-5-carbaldehyde (E)-O-methyloxime, 1.28 g (2 equivalents) of dibutylamine, 1.38 g (2 equivalents) of potassium carbonate and 0.75 g (1 equivalent) of sodium iodide are added to 25 ml of acetonitrile. The mixture is brought to reflux for 4 hours and evaporated. Extraction is carried out with ethyl acetate and washing is carried out with water and a saturated sodium chloride solution. Purification is subsequently carried out by chromatography on silica (eluent: 100/2.5 dichloromethane/methanol), which gives 2.24 g (yield: 88%) of desired compound in the base form.

2.0 g of base thus obtained and 0.361 g of oxalic acid are then added to methanol and evaporation is carried out. The residue is taken up in diethyl ether and crystallization is allowed to take place.

In this way, 2.25 g of desired compound are obtained.
Yield: 92% M.p.: 97–99° C. NMR spectrum: standard

EXAMPLE 16

2-Butyl-3-[4-[3-(dibutylamino)propoxy]benzoyl]-5-hydroxymethyl-1-benzofuran oxalate

A. Methyl 2-butyl-3-[2-(4-hydroxyphenyl)-1,3-dioxolan-2-yl]-1-benzofuran-5-carboxylate A mixture of 4.93 g (14 mmol) of methyl 2-butyl-3-(4-(ethylene glycol hydroxy)benzoyl)-1-benzofuran-5-carboxylate, 2.17 g and 0.500 g of p-toluenesulfonic acid in 250 ml of benzene is brought to reflux. Dilution is carried out with diethyl ether and washing is carried out with a sodium bicarbonate solution, water and a sodium chloride solution. Drying and evaporation are carried out.

B. 2-Butyl-5-hydroxymethyl-3-[2-(4-hydroxy-phenyl)-1,3-dioxolan-2-yl]-1-benzofuran The crude product obtained in the preceding step, dissolved in 50 ml of tetrahydrofuran, is added dropwise to 1.4 g of lithium aluminum hydride in 50 ml of tetrahydrofuran.

The mixture is stirred for 2 hours at ambient temperature, hydrolysis is carried out with a dilute solution of hydrochloric acid, until pH=3 is obtained, and separation is carried out by settling. Extraction with diethyl ether and then washing with water and a saturated sodium chloride solution are carried out.

In this way, the desired compound is obtained, which is used in the crude form. However, this compound can be purified by chromatography on silica (eluent: 100/2.5 dichloromethane/methanol).

M.p.: 100–101° C.

C. 2-Butyl-3-(4-hydroxybenzoyl)-5-hydroxymethyl-1-benzofuran

A solution formed by the crude product obtained in the preceding step and 0.8 g of pyridine p-toluenesulfonate in 100 ml of acetone containing 10 ml of water is brought to reflux for 3 hours. Evaporation is carried out and the residue is taken up in a diethyl ether/water mixture. The precipitate obtained is filtered off and is washed with water and diethyl ether, which gives a first crop of the desired product.

The organic phase is separated out by settling, and washing is carried out with water, a sodium bicarbonate solution, water and a sodium chloride solution.

Drying and evaporation are carried out, the residue is taken up with diethyl ether and filtration is carried out, which gives a second crop of the desired product.

In this way, 3.37 g of desired compound are obtained after crystallization from diethyl ether.

Yield: 74% M.p.: 180–182° C.

D. 2-Butyl-3-[4-[3-(dibutylamino)propoxy]benzoyl]-5-hydroxymethyl-1-benzofuran oxalate 1.68 g of 2-butyl-3-(4-hydroxybenzoyl)-5-hydroxymethyl-1-benzofuran, 1.18 g of 1-chloro-3-(dibutylamino)propane and 0.960 g of potassium carbonate are dissolved in 70 ml of methyl ethyl ketone. The mixture is brought to reflux for 6 hours, water is added and separation is carried out by settling. Extraction with ethyl acetate and washing with a saturated sodium chloride solution are carried out. Purification is subsequently carried out by chromatography on silica (eluent: 95/5 dichloromethane/methanol), which gives the desired compound in the free base form.

2.50 g of the base thus obtained are subsequently mixed with 0.455 g of oxalic acid in methanol, evaporation is carried out and the residue is taken up in diethyl ether. Crystallization is allowed to take place, and filtration and washing with diethyl ether are carried out.

In this way, 2.57 g of desired compound are obtained.

Yield: 85.5% NMR spectrum: standard

EXAMPLE 17

2-Butyl-3-[4-[3-(cis-3,5-diethyl-1-piperidinyl)propoxy]benzoyl-5-(3-methyl-1,2,4-oxadiazol-5-yl]-1-benzofuran

A. 2-Butyl-3-(4-hydroxybenzoyl)-5-(3-methyl-1,2,4-oxadiazol-5-yl)-1-benzofuran 1.018 g of acetamide oxime, 0.660 g of sodium hydride, 6 g of molecular sieve and 60 ml of tetrahydrofuran are placed, under argon, in a three-necked round-bottomed flask. Heating is carried out at 60° C. for 1 hour, 4.03 g of methyl 2-butyl-3-(4-hydroxy-benzoyl)-1-benzofuran-5-carboxylate dissolved in 50 ml of tetrahydrofuran are added and the mixture is brought to reflux for 3 hours. The mixture is diluted with water, a sodium chloride solution is added and extraction is carried out with ethyl acetate. Washing is carried out with a saturated sodium chloride solution.

In this way, 3.4 g of desired compound are obtained in the crystallized form.

Yield: 79% M.p.: 180–182° C.

B. 2-Butyl-3-[4-(3-bromopropoxy)benzoyl]-5-(3-methyl-1,2,4-oxadiazol-5-yl)-1-benzofuran 4.26 g (0.0113 mol) of compound obtained in the preceding step, 11.44 g (5 equivalents) of 1,3-dibromopropane and 1.88 g (1.2 equivalents) of potassium carbonate are mixed in 100 ml of methyl ethyl ketone. The mixture is brought to reflux for 3 hours and is evaporated. The residue is taken up in water and extraction is carried out with ethyl acetate. Washing is carried out with a saturated sodium chloride solution and purification is carried out by chromatography on silica (eluent: 100/3 dichloromethane/methanol).

In this way, 3.58 g of desired compound are obtained.

Yield: 64% M.p.: 85–87° C.

C. 2-Butyl-3-[4-[3-(cis-3,5-diethyl-1-piperidinyl)propoxy]benzoyl-5-(3-methyl-1,2,4-oxadiazol-5-yl]-1-benzofuran 3.4 g of compound obtained in the preceding step, 1.21 g (1.1 equivalents) of cis-3,5-diethylpiperidine hydrochloride, 1.03 g (1 equivalent) of sodium iodide and 2.83 g (3 equivalents) of potassium carbonate are introduced into 100 ml of acetonitrile. The mixture is brought to reflux for 6 hours, diluted with water and separated by settling. Extraction with ethyl acetate and washing with a saturated sodium chloride solution are carried out. Purification is subsequently carried out by chromatography on silica (eluent: 100/2.5 dichloromethane/methanol and 20% aqueous ammonia: 2 drops).

In this way, 2.55 g of desired compound are obtained.

Yield: 67% M.p.: 81–83° C. (after recrystallization from heptane) NMR spectrum: standard

EXAMPLE 18

Methyl 2-butyl-3-[4-[3-(cis-3,5-dimethyl-1-piperidinyl)propoxy]benzoyl]-1-benzofuran-6-carboxylate hydrochloride

A. Isopropyl 3-methoxy-4-trifluoromethanesulfon-yloxybenzoate 2.1 g (0.01 mol) of isopropyl 3-methoxy-4-hydroxybenzoate and 0.3 g (1.1 equivalents) of pyridine are introduced into 20 ml of dichloromethane. A solution of 3.1 g (1.1 equivalents) of trifluoromethanesulfonic anhydride in 10 ml of dichloromethane are then added dropwise, at between 0° C. and 5° C. The mixture is allowed to return to ambient temperature and is stirred for 0.5 h at this temperature, and evaporation is carried out. Extraction with ethyl acetate and washing with water, dilute hydrochloric acid, a sodium bicarbonate solution, water and, finally, a saturated sodium chloride solution are carried out.

In this way, 3.22 g of desired compound are obtained.
Yield: 94%

B. Isopropyl 3-methoxy-4-(1-hexyn-1-yl)benzoate 3.18 g (9.3 mmol) of compound obtained in the preceding step, 1.52 g (2 equivalents) of 1-hexine, 6.5 ml (approximately 5 equivalents) of triethylamine and 0.325 g (0.05 equivalent) of dichlorobis(triphenylphosphine)palladium are introduced into 25 ml of N,N-dimethylformamide. The mixture is heated at 90° C. for 2 hours, diluted with water, and dilute hydrochloric acid is added. Extraction with diethyl ether and washing with water and a saturated sodium chloride solution are carried out. Purification is subsequently carried out by chromatography on silica (eluent: 1/1 dichloromethane/heptane).

In this way, 1.35 g of desired compound are obtained.
Yield: 53%

C. 2-Butyl-1-benzofuran-6-carboxylic acid 9.62 g (35 mmol) of compound obtained in the preceding step are introduced into 200 ml of dichloromethane and the mixture is cooled to approximately −70° C. 70 ml (2 equivalents) of a solution of 1M boron tribromide in dichloromethane are then added. The mixture is allowed to return to ambient temperature and is stirred for 1 hour at ambient temperature. It is cooled by means of an ice/water mixture and hydrolysis is carried out. Extraction with dichloromethane and washing with water and a saturated sodium chloride solution are carried out. Purification is subsequently carried out by chromatography on silica (eluent: 100/3 dichloromethane/methanol).

In this way, 2.5 g of desired compound are obtained.
Yield: 32.7% M.p.: 102–104° C.

D. Methyl 2-butyl-1-benzofuran-6-carboxylate 2.5 g of compound obtained in the preceding step are introduced into 80 ml of methanol and 1 ml of concentrated sulfuric acid is added. The mixture is brought to reflux for 6 hours and evaporated. Extraction with diethyl ether and washing with water, a sodium bicarbonate solution, water and a saturated sodium chloride solution are carried out.

In this way, 2.60 g of desired compound are obtained.
Yield: 98%

E. Methyl 2-butyl-3-[4-(3-bromopropoxy)benzoyl]-1-benzofuran-6-carboxylate 2.60 g (11 mmol) of compound obtained in the preceding step and 4.58 g (1.5 equivalents) of 4-(3-bromopropoxy) benzoyl chloride are introduced into 150 ml of dichloromethane. 2.2 ml of stannic chloride in 50 ml of dichloromethane are then added, at a temperature of 15 to 20° C. The mixture is stirred at ambient temperature for 72 hours, poured onto an ice/water mixture and filtered, and evaporation is carried out. Extraction with ethyl acetate and washing with a sodium carbonate solution, with water and with a saturated sodium chloride solution are carried out. Purification is then carried out by chromatography on silica (eluent: 100/2 dichloromethane/ethyl acetate).

In this way, 3.95 g of desired compound are obtained.
Yield: 76%

F. Methyl 2-butyl-3-[4-[3-(cis-3,5-dimethyl-1-piperidinyl)propoxy]benzoyl]-1-benzofuran-6-carboxylate hydrochloride 3.9 g (8.2 mmol) of compound obtained in the preceding step, 1.36 g (1.1 equivalents) of cis-3,5-diethylpiperidine hydrochloride, 1.25 g (1 equivalent) of sodium iodide and 3.42 g (3 equivalents) of potassium carbonate are introduced into 100 ml of acetonitrile. The mixture is brought to reflux for 3 hours, diluted in water and separated by settling. Extraction is carried out with ethyl acetate. Purification is then carried out by chromatography on silica (eluent: 100/3/0.1 dichloromethane/methanol/ammonia), which gives 3.36 g (yield: 81%) of desired compound in the base form (NMR spectrum: standard).

3.30 g of base thus obtained are then dissolved in diethyl ether and a solution of hydrogen chloride in diethyl ether is added. Filtration and then washing with diethyl ether are carried out. Purification is subsequently carried out by crystallization from diethyl ether.

In this way, 2.74 g of desired compound are obtained.
Yield: 77% M.p.: 169–171° C. NMR spectrum: standard The following compound was prepared by following the same protocol as above:

Methyl 2-butyl-3-[4-(1-piperidinyl)propoxy]benzoyl]-1-benzofuran-6-carboxylate hydrochloride
(Example 19)

M.p.: 176–178° C. NMR spectrum: standard

EXAMPLE 20

Methyl 2-butyl-3-(4-{2-[methyl(4-nitrophenethyl)amino]-ethoxy}benzoyl)-1-benzofuran-5-carboxylate 4.3 g (9.36 mmol) of methyl 2-butyl-3-[4-(3-bromopropoxy)benzoyl]-1-benzofuran-6-carboxylate are introduced into 50 ml of acetonitrile and 1.7 g (9.36 mmol) of N-methyl-N-(4-nitrophenyl)ethylamine, 1.4 g (9.36 mmol) of sodium iodide and 2.58 g (18.7 mmol) of potassium carbonate are then added.

The mixture is brought to reflux for 18 hours, concentrated to dryness and extracted with ethyl acetate. Washing is carried out with water and a saturated sodium chloride solution, and then purification is carried out by chromatography on silica (eluent: 99/1 and then 97/3 dichloromethane/methanol).

In this way, 5.0 g of desired compound are obtained.
Yield: 95.6% NMR spectrum: standard

EXAMPLE 21

Methyl 3-(4-{2-[(4-aminophenethyl)(methyl)
amino]-ethoxy}benzoyl)-2-butyl-1-benzofuran-5-
carboxylate 5.0 g of compound obtained in the preceding example are introduced into 100 ml of absolute ethanol and a catalytic amount of Raney nickel is added.

Hydrogenation is subsequently carried out under normal pressure and at ambient temperature. When the reaction no longer evolves, filtration over diatomaceous earth and rinsing with absolute ethanol are performed. Concentration is carried out, followed by purification by chromatography on silica (eluent: 97/3 and then 95/5 dichloromethane/methanol).

In this way, 3.57 g of desired compound are obtained.
Yield: 75.5% NMR spectrum: standard

EXAMPLE 22

Methyl 2-butyl-3-{4-[2-(methyl{4-[(methylsulfo-
nyl)-amino]phenethyl}amino)ethoxy]benzoyl}-1-
benzofuran-5-carboxylate 3.57 g (6.75 mmol) of compound obtained in the preceding step and 2.59 g (14.9 mmol) of methanesulfonic anhydride are introduced into 200 ml of dichloromethane. The mixture is stirred at ambient temperature for 18 hours and concentrated to dryness. The residue is taken up with a 2N sodium bicarbonate solution and extraction is carried out with ethyl acetate. Washing is carried out with water and a sodium chloride solution, followed by purification by chromatography on silica (eluent: 97/3 and then 50/50 dichloromethane/methanol and, finally, pure methanol).

In this way, 2.928 g of desired compound are obtained.
Yield: 71.5% NMR spectrum: standard

EXAMPLE 23

Methyl 3-(5-cyano-3-{4-[3-(dibutylamino)propoxy]-
benzoyl}-1-benzofuran-2-yl)propanoate oxalate A. 3-Iodo-4-hydroxybenzonitrile 11.9 g (0.1 mol) of 4-hydroxybenzonitrile are dissolved in 250 ml of methanol and 250 ml of 20% aqueous ammonia are added. A solution of 31.75 g of iodine in 250 ml of methanol is then added dropwise, with care, due to the explosive nature of the reaction. After addition, the mixture is stirred for 2 hours at ambient temperature. The methanol is evaporated off, dilution is carried out in water and acidification with a hydrochloric acid solution is performed until pH=2 to 3 is obtained. Extraction with ethyl acetate and washing with water, a sodium thiosulfate solution and a saturated sodium chloride solution are subsequently carried out.

In this way, 24.73 g of desired compound are obtained.
M.p.: 144–146° C.

The compound below was prepared using the same process as above:

Isopropyl 3-iodo-4-hydroxybenzoate

B. Methyl 3-(5-cyano-1-benzofuran-2-yl)propanoate 19.38 g (79 mmol) of compound obtained in the preceding step, 9.81 g (1.1 equivalents) of methyl 4-pentanoate, 0.750 g (0.05 equivalent) of copper iodide, 2.77 g of dichlorobis(triphenylphosphine)-palladium and 100 ml (10 equivalents) of tetramethylguanidine are introduced into 125 ml of N,N-dimethylformamide. The mixture is stirred at ambient temperature for 20 hours, diluted with 1000 ml of water and extracted with 600 ml of ethyl acetate. Washing is carried out with water, dilute hydrochloric acid, water and a saturated sodium chloride solution. Purification is subsequently carried out by chromatography on silica (eluent: 100/1 dichloromethane/ethyl acetate).

In this way, 9.93 g of desired compound are obtained.
Yield: 59% M.p.: 91–92° C.

The following compound was obtained by following the same process as above:

Methyl 3-(5-isopropoxycarbonyl-1-benzofuran-2-yl)
propanoate

M.p.: 62–64° C.

C. Methyl 3-[5-cyano-3-(4-methoxybenzoyl)-1-
benzofuran-2-yl]propanoate 9.91 g of compound obtained in the preceding step in 50 ml of dichloroethane are added, at around +10° C., to a solution of 11.46 g (1.5 equivalents) of ferric chloride in 80 ml of dichloroethane maintained under argon, and then 12.03 g (1.5 equivalents) of anisoyl chloride in 50 ml of dichloroethane are introduced, at a temperature of +10 to +15° C. The mixture is allowed to return to ambient temperature and is then stirred, at this temperature, for 5 hours. It is poured onto an ice/water mixture, the precipitate is filtered off and the filtrate is separated out by settling. The aqueous phase is extracted with dichloromethane and the organic phases are washed, which organic phases are purified by chromatography on silica (eluent: 100/2 dichloromethane/ethyl acetate).

In this way, 10.78 g of desired compound are obtained.
Yield: 64% M.p.: 95–98° C.

D. Methyl 3-[5-cyano-3-(4-hydroxybenzoyl)-1-ben-
zofuran-2-yl]propanoate 9.73 g of compound obtained in the preceding step and 10.8 g of aluminum chloride are introduced into 350 ml of toluene. The mixture is heated at 80° C. for 6 hours and then separated by settling. The residue is taken up in tetrahydrofuran and ice is added gently. Separation is carried out by settling, the aqueous phase is extracted with ethyl acetate and the three organic phases are pooled. Washing is carried out with water, followed by purification by chromatography on silica (eluent: 95/5 and then 90/10 dichloromethane/ethyl acetate.

In this way, 5.57 g of desired compound are obtained.
Yield: 95% M.p.: 156–158° C.-

E. Methyl 3-(5-cyano-3-{4-[3-(dibutylamino)-propoxy]benzoyl}-1-benzofuran-2-yl)propanoate oxalate 4.54 g (13 mmol) of compound obtained in the preceding step, 2.95 g (1.1 equivalents) of 3-chloro-1-(dibutylamino) propane and 2.16 g (1.2 equivalents) of potassium carbonate are introduced into 70 ml of methyl ethyl ketone. The mixture is brought to reflux for 6 hours, then dilution with water and extraction with ethyl acetate are carried out. Washing is carried out with a saturated sodium chloride solution, followed by purification by chromatography on silica (eluent: 5/5 heptane/ethyl acetate, 95/3 and then 90/10 dichloromethane/methanol), which gives 6.65 g of the desired compound in the free base form. A 2.32 g sample of this base is taken and introduced into methanol. 0.416 g of oxalic acid is added thereto and evaporation is carried out. The residue is taken up in diethyl ether and evaporation is carried out. Purification is subsequently carried out by crystallization from diethyl ether.

In this way, 2.4 g of desired compound are obtained.

Yield: 87% M.p.: 76–79° C. NMR spectrum: standard

The product below is obtained by following the same process as above, but using hydrochloric acid instead of oxalic acid:

Methyl 3-(4-{3-[cis-3,5-diethylpiperidinyl]propoxy}benzoyl)-2-(3-methoxy-3-oxopropyl)-1-benzofuran-5-carboxylate hydrochloride (Example 24)

Yield: 81% M.p.: 166–169° C. (after crystallization from diethyl ether)

NMR spectrum: standard

EXAMPLE 25

2-Butyl-5-cyano-3-[4-[3-(dibutylamino)propoxy]benzoyl]-1-benzofuran oxalate

A. 2-Methoxy-5-cyanobenzaldehyde

A mixture of 40.63 g of 2-methoxy-5-bromo-benzaldehyde, 13.35 g of zinc cyanide and 8.7 g of tetrakis(triphenylphosphine)palladium in 240 ml of deoxygenated N,N-dimethylformamide is heated, under argon, for 3 hours. The mixture is allowed to return to ambient temperature and extraction is carried out with 600 ml of toluene. Washing is subsequently carried out with twice 600 ml of 2N aqueous ammonia and then with a saturated sodium chloride solution. Purification is then carried out by crystallization from diisopropyl ether.

In this way, 30.2 g of desired compound are obtained.

Yield: 99% M.p.: 115–118° C.

B. 2-Hydroxy-5-cyanobenzaldehyde 31.08 g of compound obtained in the preceding step and 24.52 g of lithium chloride are introduced into 500 ml of N,N-dimethylformamide. The mixture is brought to reflux for 2 hours and the solvent is evaporated off. The residue is taken up in a potassium acid sulfate solution and extraction is carried out with ethyl acetate. Washing is then carried out with water and a saturated sodium chloride solution.

In this way, 24.5 g of desired compound are obtained.

Yield: 86%

C. Methyl 2-(2-formyl-4-cyanophenoxy)hexanoate 24.5 g of compound obtained in the preceding step, 47.52 g of methyl 2-bromohexanoate and 28.8 g of potassium carbonate are placed in 400 ml of N,N-dimethylformamide. The mixture is heated at approximately 80° C. for 1.5 hours and the solvent is evaporated off. The residue is taken up in a potassium acid sulfate solution and extraction is carried out with ethyl acetate. Washing is then carried out with water and a saturated sodium chloride solution.

In this way, 53.6 g of desired compound are obtained in the crude form.

M.p.: 77–79° C.

D. 2-(2-Formyl-4-cyanophenoxy)hexanoic acid 53.6 g of crude compound obtained in the preceding step and 8.6 g of sodium hydroxide are introduced into 320 ml of methanol containing 200 ml of dioxane and 160 ml of water. The mixture is stirred for 1.5 hours at ambient temperature and evaporation is carried out. The residue is taken up in water containing concentrated hydrochloric acid and extraction is carried out with ethyl acetate. Washing is then carried out with water and a saturated sodium chloride solution.

In this way, 52.1 g of desired compound are obtained in the crude form.

E. 2-Butyl-5-cyano-1-benzofuran 47.66 g of benzenesulfonyl chloride are introduced into 100 ml of toluene and 68.23 g of triethylamine in 50 ml of toluene are added. The mixture is heated to 80° C. and then 52.1 g of compound obtained in the preceding step dissolved in 400 ml of toluene are added dropwise at a temperature of less than 90° C. As soon as the addition is finished, the heating is continued for 0.5 hours and then the mixture is allowed to turn to ambient temperature. Washing is carried out with water and the aqueous phase is extracted with toluene. The pooled organic phases are agitated with 100 ml of 2N sodium hydroxide and separation is carried out by settling. Extraction with toluene and washing with water, a potassium bisulfate solution, water and a saturated sodium chloride solution are carried out. Purification is then carried out by chromatography on silica (eluent: dichloromethane).

In this way, 19.94 g of desired compound are obtained.

Overall yield for the 5 steps: 53%

F. 2-Butyl-5-cyano-3-(4-methoxybenzoyl)-1-benzofuran 32.43 g (2 equivalents) of ferric chloride are introduced into 200 ml of dichloroethane, under argon. 19.92 g of compound obtained in the preceding step are then added, at around 10° C., and 34.36 g (2 equivalents) of anisoyl chloride dissolved in 200 ml of dichloroethane are then introduced at a temperature of between +10 and +15° C. The mixture is allowed to return to ambient temperature and stirred at this temperature for 16 hours. It is poured onto an ice/water mixture and filtration is carried out over sintered glass. The filtrate is separated by settling, the aqueous phase is extracted with dichloromethane and the organic phases are mixed. Washing is carried out with a dilute sodium bicarbonate solution, water and a saturated sodium chloride solution. Purification is subsequently carried out by chromatography on silica (eluent: dichloromethane).

In this way, 24.87 g of desired compound are obtained.

Yield: 74.5%

G. 2-Butyl-5-cyano-3-(4-hydroxybenzoyl)-1-benzofuran 16.27 g of compound obtained in the preceding step and 19.9 g of aluminum chloride are introduced into 200 ml of toluene. The mixture is heated at 60° C. for 2 hours and the toluene is separated by settling. The residue is dissolved in tetrahydrofuran and a water/ice mixture is added. The mixture is stirred for 1 hour and separated by settling, and the aqueous phase is extracted with ethyl acetate. The 3 organic phases are then mixed and washing is carried out with water and a sodium chloride solution. Purification is subsequently carried out by crystallization from heptane.

In this way, 14.05 g of desired compound are obtained.
Yield: 90% M.p.: 152–153° C.

H. 2-Butyl-5-cyano-3-[4-[3-(dibutylamino)-propoxy]benzoyl]-1-benzofuran 2.02 g of compound obtained in the preceding step, 1.45 q of 3-chloro-1-(dibutylamino)propane and 1.06 g of potassium carbonate are introduced into 30 ml of methyl ethyl ketone. The mixture is brought to reflux for 6 hours and water is added. The mixture is separated by settling and the aqueous phase is extracted with ethyl acetate. The pooled aqueous phases are washed with a saturated sodium chloride solution and extraction is carried out with ethyl acetate. Purification is subsequently carried out by chromatography on alumina (eluent: 95/5 heptane/ethyl acetate), which gives the desired compound in the free base form (2.25 g; yield: 72%). 1.86 g of this base compound and 0.343 g of oxalic acid dissolved in methanol are then mixed. The mixture is evaporated and diethyl ether is added. The mixture is stirred for a few hours, and filtration and washing with diethyl ether are carried out. Crystallization is then allowed to take place.

In this way, 2.11 g of desired compound of oxalate are obtained.
Yield: 96% M.p.: 85–87° C. NMR spectrum: standard

EXAMPLE 26

Methyl 3-{[(2-butyl-3-{4-[3-(neopentylamino)propoxy]-benzoyl}-1-benzofuran-5-yl)carbonyl]amino}propanoate

A. Methyl 2-butyl-3-{4-[3-[(N-neopentyl-N-tert-butoxycarbonyl)amino]propoxy]benzoyl}-1-benzofuran-5-carboxylate 8.57 g (18 mmol) of 2-butyl-3-[4-[3-(neopentylamino)propoxy]benzoyl]-5-methoxycarbonyl-benzofuran and 4.29 g (1.1 equivalents) of tert-butoxy-carboxylic acid anhydride are introduced into 100 ml of chloroform. The mixture is brought to reflux for 3 hours and then evaporation is carried out.

In this way, the desired product is obtained in the crude form.

B. 2-Butyl-3-{4-[3-[(N-neopentyl-N-tert-butoxycarbonyl)amino]propoxy]benzoyl}-1-benzofuran-5-carboxylic acid The crude product obtained in the preceding step is dissolved in 200 ml of dioxane containing 40 ml of methanol and 40 ml of water. 1.45 g (approximately 2 equivalents) of sodium hydroxide are added and the mixture is then stirred at ambient temperature for 48 hours. Evaporation is carried out, the residue is taken up in water and a potassium hydrogen sulfate solution is used to acidify. Extraction with ethyl acetate and washing with water and a saturated sodium chloride solution are carried out.

In this way, 11.23 g of desired product are obtained in the crude form.
Yield: 100%

C. Methyl 3-{[(2-butyl-3-{4-[3-[(N-neopentyl-N-tert-butoxycarbonyl)amino]propoxy]benzoyl}-1-benzofuran-5-yl)carbonyl]amino}propanoate 7.48 g of crude product obtained in the preceding step, 2 q (1.1 equivalents) of methyl 3-aminopropanoate hydrochloride, 4.5 g of triethylamine and 6.32 g (1.1 equivalents) of BOP are introduced into 150 ml of dichloromethane. The mixture is stirred for 3 hours at ambient temperature and then evaporation is carried out. Extraction with ethyl acetate and washing with water, a potassium hydrogen sulfate solution, water, a sodium carbonate solution, water and, finally, a saturated sodium chloride solution are carried out. Purification is subsequently carried out by chromatography on silica (eluent: 85/15 dichloromethane/ethyl acetate).

In this way, 6.2 g of desired product are obtained in the crude form. Global yield of the 3 steps: 79.5%

D. Methyl 3-{[(2-butyl-3-{4-[3-(neopentylamino)propoxy]benzoyl}-1-benzofuran-5-yl)carbonyl]amino}propanoate 6.15 g of product obtained in the preceding step are dissolved in 50 ml of dichloromethane. The solution is cooled by means of an ice/water bath and 50 ml of trifluoroacetic acid are added. The mixture is stirred at ambient temperature for 1 hour, evaporation is carried out, and the residue is taken up in diethyl ether. Evaporation is carried out two more times. Purification is then carried out by chromatography on silica (eluent: 100/5/0.2 dichloromethane/methanol/aqueous ammonia).

In this way, 4.5 g of desired compound are obtained.
Yield: 78%

EXAMPLE 27

Methyl 2-{[(2-butyl-3-{4-[3-(dibutylamino)propoxy]-benzoyl}-1-benzofuran-5-yl)carbonyl]amino}benzoate oxalate 6.28 g (0.012 mol) of 2-butyl-3-[4-[3-(dibutylamino)propoxy]benzoyl]-1-benzofuran-5-carboxylic acid are dissolved in 150 ml of chloroform. 6 ml of thionyl chloride are then added and the mixture is brought to reflux for 3 hours. Evaporation is carried out then the residue is taken up in diethyl ether, 3 times. The crude acyl chloride thus formed is subsequently introduced into 130 ml of dichloromethane and 9 g (0.06 mol) of 2-methoxycarbonylaniline are added. The reaction medium is maintained at ambient temperature for 12 hours and evaporation is carried out. Extraction with ethyl acetate and washing with a dilute potassium carbonate solution, water and a sodium chloride solution are carried out. Purification is then carried out by chromatography on silica (eluent: 96/4 dichloromethane/methanol), which gives 5.26 g of desired product in the base form (yield: 68%). 2 g (3.1 mmol) of base product thus obtained are then dissolved in 15 ml of absolute ethanol and 0.281 g (3.1 mmol) of oxalic acid is dissolved in 10 ml of absolute ethanol. The two solutions are mixed and evaporation is carried out. The residue is taken up in diethyl ether and crystallization is allowed to take place. The precipitate formed is filtered off and dried.

In this way, 1.9 g of desired compound are obtained.
Yield: 84% M.p.: 89° C. NMR spectrum: standard

EXAMPLE 28

2-{[(2-Butyl-3-{4-[3-(dibutylamino)propoxy]benzoyl}-1-benzofuran-5-yl)carbonyl]amino}benzoic acid hydrochloride 3.26 g (5.1 mmol) of methyl 2-{[(2-butyl-3-{4-[3-(dibutylamino)propoxy]benzoyl}-1-benzofuran-5-yl]carbonyl]amino}benzoate oxalate are dissolved in 20 ml of dioxane.

0.407 g (10 mmol) of sodium hydroxide in 4 ml of water containing 4 ml of methanol are added. The medium is then left to stand at ambient temperature for 4 hours and then filtered. Extraction with ethyl acetate and then washing with water, a 1N hydrochloric acid solution, water and a sodium chloride solution are carried out. Purification is subsequently carried out by chromatography on silica (eluent: 96/4 dichloromethane/methanol).

In this way, 2.06 [lacuna] of desired product are obtained.
Yield: 61% M.p.: 109° C. NMR spectrum: standard

EXAMPLE 29

Isopropyl 2-butyl-3-(4-{3-[cis-3,5-diethylpiperidinyl]-propoxy}benzyl)-1-benzofuran-5-carboxylate oxalate 3.19 g (4.89 mmol) of isopropyl 2-butyl-3-(4-{3-[cis-3,5-diethylpiperidinyl]propoxy}benzoyl)-1-benzofuran-5-carboxylate are introduced into 50 ml of isopropanol and then 1 spoonful of palladium charcoal at 10% and a few drops of concentrated hydrochloric acid are added successively. Hydrogenation is subsequently carried out under normal pressure for 48 hours at 45° C. The mixture is pulled dry over diatomaceous earth, and the product is rinsed with isopropanol, filtered and concentrated. Purification is then carried out by chromatography on silica (eluent: dichloromethane/methanol), which gives 1.533 g (yield: 49.1%) of the desired compound in the base form.

1.32 g (2.41 mmol) of base compound thus obtained are introduced into a minimal amount of ethanol to ensure dissolution thereof and 0.217 g (2.41 mmol) of oxalic acid is added. The mixture is concentrated and triturated in diethyl ether, and the product is filtered and dried. Purification is then carried out by crystallization.

In this way, 1.203 g of desired compound are obtained.
Yield: 78.3% M.p.: 148–149° C. NMR spectrum: standard

EXAMPLE 30

Methyl 2-butyl-3-[4-(cis-3,5-dimethyl-1-piperidinyl)-propoxy]benzoyl]-1-benzofuran-4-carboxylate hydrochloride A) Methyl 2-hydroxy-3-methoxybenzoate 25.5 g (0.152 mol) of 2-hydroxy-3-methoxy-benzoic acid are introduced into 250 ml of methanol containing 1 ml of sulfuric acid. The mixture is brought to reflux for 4 days, concentrated to dryness and then extracted with ethyl acetate. Washing is then carried out with water, a 10% sodium carbonate solution, water and a sodium chloride solution.

In this way, 25.2 g of desired compound are obtained.
Yield: 91.2% M.p.: 68–69° C.

B) Methyl 2-trifluoromethanesulfonyloxy-3-methoxybenzoate 25 g (0.137 mol) of compound obtained in the preceding step are introduced into 200 ml of dichloromethane and 11.93 g (0.151 mol) of pyridine are added. A mixture of 42.6 g (0.151 mol) of triflic anhydride in 200 ml of dichloromethane is then added, at a temperature of 0° C. to 5° C. The mixture is stirred at ambient temperature for 3 hours, concentrated to dryness and extracted with diethyl ether. Washing is then carried out with water, dilute hydrochloric acid, water, a dilute sodium bicarbonate solution, water and a sodium chloride solution. Purification is then carried out by chromatography on silica (eluent: 5/5 dichloromethane/heptane).

In this way, 19.36 g of desired compound are obtained.
Yield: 54.9%

C) Methyl 2-(1-hexynyl)-3-methoxybenzoate 19.26 g (74.9 mmol) of compound obtained in the preceding step are introduced into 200 ml of N,N-dimethylformamide and then 12.3 g (16.85 ml; 149.7 mmol) [lacuna], 37.94 g (52.2 ml; 375 mmol) of triethylamine and 2.62 g (3.74 mmol) of dichlorobis-(triphenylphosphine)palladium are added. The mixture is heated at 90° C. for 3 hours, then diluted with water and extracted with diethyl ether. Washing is then carried out with dilute hydrochloric acid, water and a sodium chloride solution. Purification is then carried out by chromatography on silica (eluent: 5/5 dichloromethane/heptane and then dichloromethane).

In this way, 6.1 g of desired compound are obtained.
Yield: 33.1%

D) Methyl 2-butyl-1-benzofuran-4-carboxylate 5.45 g (22.1 mmol) of compound obtained in the preceding step are introduced into 100 ml of dichloromethane. 44.5 ml of a molar solution of bromine tribromide in dichloromethane are then added, at a temperature of approximately –5° C. The mixture is stirred at ambient temperature for 4 hours, and then water is added with care, while maintaining the temperature below 30° C. The mixture is subsequently extracted with dichloromethane and purification is carried out by chromatography on silica (eluent: dichloromethane).

In this way, 2 g of the desired compound are obtained.
Yield: 39%

E) Methyl 2-butyl-3-[4-(3-bromopropoxy)benzoyl]-1-benzofuran-4-carboxylate 4 g (17.2 mmol) of the compound obtained in the preceding step are introduced into 50 ml of dichloroethane and 7.2 g (25.8 mmol) of 4-(3-bromopropoxy)benzoyl chloride are added. 3.44 ml (25.8 mmol) of tin tetrachloride are then added, at between 150 and 20° C. The mixture is stirred for 18 hours and diluted with dichloromethane. This mixture is washed with water and an aqueous sodium chloride solution and concentrated, and the product is taken up with ethyl acetate. Washing is then carried out several times with a dilute aqueous solution of sodium bicarbonate, with water and then with a sodium chloride solution. The product is dried and concentrated. Purification is then carried out by chromatography on silica (eluent: dichloromethane).

In this way, 5.66 g of desired compound are obtained.

Yield: 69.5%

F) Methyl 2-butyl-3-[4-(cis-3,5-dimethyl-1-piperidinyl)propoxy]benzoyl]-1-benzofuran-4-carboxylate hydrochloride 2.8 g (5.9 mmol) of compound obtained in the preceding step are introduced into 100 ml of acetonitrile and then 0.979 g (1.1 equivalents) of cis-3,5-diethylpiperidine hydrochloride, 0.899 g (1 equivalent) of sodium iodide and 2.46 g (3 equivalents) of potassium carbonate are added. The mixture is brought to reflux for 2 hours and then diluted with ethyl acetate. Washing is carried out with water and a sodium chloride solution, and then purification is carried out by chromatography on silica (eluent: 98/2/0.1 dichloromethane/methanol/aqueous ammonia), which gives 2.137 g (yield: 71.6%) of the desired compound in the free base form.

2.117 g of this base compound are then dissolved in the minimum amount of diethyl ether, and the amount of diethyl ether, containing hydrogen chloride, required to cause complete precipitation of the hydrochloride is then added. The hydrochloride formed is filtered and then dried.

In this way, 2.078 [lacuna] of the desired compound are obtained.

Yield: 91.56% M.p.: 135–136° C. NMR spectrum: standard

Methyl 2-butyl-3-[4-(3-(1-piperidinyl)propoxy]benzoyl]-1-benzofuran-4-carboxylate oxalate (Example 31) was prepared using the same process as above.

M.p.: 160° C. NMR spectrum: standard

EXAMPLE 32

3-(5-Cyano-3-[4-[3-(dibutylamino)propoxy]benzoyl]-1-benzofuran-2-yl)propanoic acid hydrochloride A mixture of 3.55 g of methyl 3-(5-cyano-3-[4-[3-(dibutylamino)propoxy]benzoyl]-1-benzofuran-2-yl)propanoate and 4.08 g (1 equivalent) of tributyltin oxide is heated at 100° C. for 2.5 hours. It is diluted with water and extracted with ethyl acetate, and the extract is concentrated, which gives 3.17 g (yield: 91.5%) of desired compound in the base form.

3.1 g of this base compound are then dissolved in ethyl acetate, a solution of hydrogen chloride in diethyl ether is added until a slightly acid pH is obtained, and crystallization from the ethyl acetate is allowed to take place. The product is filtered, washed with ethyl acetate and dried under vacuum.

In this way, 2.35 g of desired compound are obtained.

Yield: 70.5% M.p.: 165–168° C. (ethyl acetate) NMR spectrum: standard

EXAMPLE 154

(2-Butyl-3-(2-[4-(2-dibutylaminoethoxy)phenyl]-1,3-dioxolan-2-yl)benzofuran-5-yl)methanol Oxalate A. Methyl 3-(2-[4-(2-bromoethoxy)phenyl]-1,3-dioxolan-2-yl)-2-butylbenzofuran-5-carboxylate 10.0 g (0.022 mol) of methyl 3-[4-(2-bromoethoxy)benzoyl]-2-butylbenzofuran-5-carboxylate, 3.39 g (0.055 mol) of ethylene glycol, 890 mg of para-toluenesulfonic acid (pTsA) and 100 ml of benzene are brought to reflux for 3 days, eliminating the water formed using a Dean-Stark apparatus. The mixture is evaporated to dryness and the residue is chromatographed on a column of silica, eluting with DCM (dichloromethane) and then a DCM/ethyl acetate (99/1) mixture. 5 g of the pure desired compound are thus isolated.

B. (3-(2-[4-(2-Bromoethoxy)phenyl]-1,3-dioxolan-2-yl)-2-butylbenzofuran-5-yl)methanol 4.87 g (0.097 mol) of the compound obtained in the preceding step A are dissolved in 20 ml of anhydrous THF, under argon, and the mixture is cooled to −70° C. 32 ml of a solution of diisobutylaluminum hydride (DIBAL) in toluene are added at this temperature. After the addition has been completed, the mixture is stirred for a further 1 hour at −70° C. 1 ml of methanol is then added, at −70° C., and then, when gas is no longer being given off, water is added. Filtration is carried out through celite. The gel and celite are washed 3 times with ethyl acetate. The organic phase is separated by settling and the aqueous phase is then reextracted with ethyl acetate. The pooled organic phases are washed with water and an aqueous NaCl solution. Drying is carried out over $Na_2SO_4$. Purification is carried out by chromatography on silica (eluent: DCM/ethyl acetate at 92/8).

In this way, a total of 3.25 g of the desired compound are obtained.

C. (2-Butyl-3-(2-[4-(2-dibutylaminoethoxy)-phenyl]-1,3-dioxolan-2-yl)benzofuran-5-yl)-methanol 3.25 g of the compound obtained in the preceding step, 2.64 g of dibutylamine, 1.02 g of sodium iodide, 2.83 g of potassium carbonate and 50 ml of acetonitrile are mixed, and the mixture is refluxed for 3 hours. It is evaporated to dryness, the residue is taken up with ethyl acetate and washing is carried out with water and an aqueous NaCl solution. Drying is carried out over $Na_2SO_4$. Purification is carried out by chromatography on silica (eluent: DCM/methanol at 95/5).

In this way, 1.84 g of the desired compound are obtained.

D. 2-Butyl-3-(2-[4-(2-dibutylaminoethoxy)-phenyl]-1,3-dioxolan-2-yl)benzofuran-5-yl)methanol oxalate 1.84 g of the compound obtained in the preceding step C and 313 mg of oxalic acid in 20 ml of methanol are mixed. The mixture is evaporated. After trituration in ether, the powder is filtered over sintered glass. Drying is carried out under vacuum.

In this way, 1.7 g of the desired compound are obtained.

NMR spectrum: standard; see below

EXAMPLE 155

Isopropyl 2-butyl-3-[4-(3-dibutylamino-2-hydroxypropoxy)benzoyl]benzofuran-5-carboxylate oxalate

A. Isopropyl 2-butyl-3-(4-oxiranylmethoxy-benzoyl)benzofuran-5-carboxylate

A mixture of 3.15 g of isopropyl 2-butyl-3-(4-hydroxybenzoyl)benzofuran-5-carboxylate, 25 ml of isopropanol, 15 ml of epibromohydrin and 365 mg (1.1 equivalents) of NaOH is brought to reflux for 1 hour. The mixture is evaporated, and the residue is taken up with water and extracted 3 times with ethyl acetate. The extract is washed with water and then with a saturated NaCl solution. Drying is carried out over $Na_2SO_4$ and the product is concentrated. Purification is carried out by chromatography on silica (eluent: ethyl acetate/dichloromethane).

In this way, 3.15 g of the desired compound are obtained.

B. Isopropyl 2-butyl-3-[4-(3-dibutylamino-2-hydroxypropoxy)benzoyl]benzofuran-5-carboxylate 3.15 g of the compound obtained in the preceding step A, 3.15 g of dibutylamine and 20 ml of acetonitrile are mixed and the mixture is brought to reflux for 16 hours. The solvent is evaporated off and purification is carried out by chromatography on silica (eluent: ethyl acetate/dichloromethane and then methanol/dichloromethane).

In this way, 3.6 g of the desired compound are obtained.

C. Isopropyl 2-butyl-3-[4-(3-dibutylamino-2-hydroxypropoxy)benzoyl]benzofuran-5-carboxylate oxalate 3.6 g of the compound obtained in the preceding step B and 585 mg of oxalic acid in methanol are mixed. The mixture is evaporated. After trituration in ether, the powder is filtered over sintered glass. Drying is carried out under vacuum.

In this way, 2.1 g of the desired compound are obtained.
M.p.: 87–88° C. NMR spectrum: standard

EXAMPLE 158

2-Piperidin-1-ylethyl 2-butyl-3-[4-(3-piperidin-1-ylpropoxy)benzoyl]benzofuran-5-carboxylate hydrochloride

A. 2-Piperidin-1-ylethyl 2-butyl-3-[4-(3-piperidin-1-ylpropoxy)benzoyl]benzofuran-5-carboxylate 7.5 g (0.016 mol) of 2-butyl-3-[4-(3-piperidin-1-ylpropoxy)benzoyl]benzofuran-5-carboxylic acid are dissolved in 50 ml $CHCl_3$. 15 ml of $SOCl_2$ are added. The mixture is brought to reflux for 3 hours. Evaporation is carried out and the residue is taken up three times in ether. The product is taken up in 50 ml of DCM. 2.34 ml of 2-(N-piperidyl)-1-ethanol (2.27 g; 0.0176 mol) are added and the mixture is stirred for 24 hours at ambient temperature. Evaporation is carried out, the residue is taken up with ethyl acetate and the mixture is washed with water, a solution of NaOH, $H_2O$ and a solution of NaCl. Purification is carried out by chromatography on silica (eluent: DCM/methanol/$NH_4OH$: 92/8/0.5).

In this way, 2.32 g of the desired compound are obtained.
Yield: 25%

B. 2-Piperidin-1-ylethyl 2-butyl-3-[4-(3-piperidin-1-ylpropoxy)benzoyl]benzofuran-5-carboxylate hydrochloride 2.3 g (0.004 mol) of the compound obtained in the preceding step A are dissolved in a mixture of ether and ethyl acetate. A solution of hydrochloric acid dissolved in ether is added. The mixture is evaporated, the residue is taken up in ether and filtration is carried out.

In this way, 2.02 g of the desired compound are obtained.
Yield: 78%

The compounds listed below were prepared using the processes described in the preceding examples. For each of these compounds, the NMR spectra proved to be in accordance with the described structures.

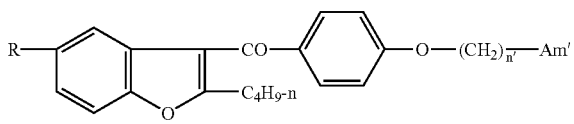

| R | Am' | n' | Characteristics | Ex. |
|---|---|---|---|---|
| H₃C—N⟨piperidine⟩—O—CO— | —N(C₄H₉)₂ | 3 | Oxalate | 33 |
| H₅C₂—O—CO— | 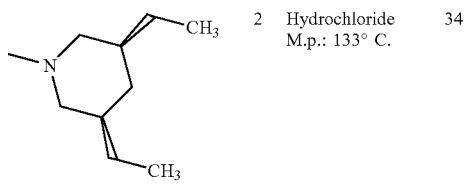 | 2 | Hydrochloride M.p.: 133° C. | 34 |

-continued

R—[benzofuran]—CO—[C6H4]—O—(CH2)n'—Am'
(benzofuran 2-position: C4H9-n)

| R | Am' | n' | Characteristics | Ex. |
|---|---|---|---|---|
| H5C2O—CO— | N-methyl-3,5-bis(ethylidene)piperidine | 3 | Hydrochloride M.p.: 164° C. | 35 |
| methyl 4-acetamidobenzoate group | —N(C4H9)2 | 3 | Oxalate | 36 |
| H5C2—NH—CO— | —N(C4H9)2 | 3 | Oxalate M.p.: 85° C. | 37 |
| neo-H11C5—O—CO— | —N(C4H9)2 | 3 | Oxalate M.p.: 102° C. | 38 |
| cyclopentyl-O-CO— | —N(C4H9)2 | 3 | Oxalate M.p.: 99° C. | 39 |
| i-H9C4—O—CO— | —N(C4H9)2 | 3 | Oxalate M.p.: 98° C. | 40 |
| (i-H7C3)2—CH—CO— | N-methyl-3,5-bis(ethylidene)piperidine | 3 | Oxalate M.p.: 105° C. | 41 |
| t-H9C4—CO2— | N-methyl-3,5-bis(ethylidene)piperidine | 3 | Oxalate M.p.: 166° C. | 42 |
| cyclopentyl-O-CO— | N-methyl-3,5-bis(ethylidene)piperidine | 3 | Oxalate (amorphous white solid) | 43 |
| n-H7C3—CO2— | —N(C4H9)2 | 3 | Oxalate (amorphous solid) | 44 |
| (CH3)2N—CH2—C(CH3)2—O—CO— | —N(C4H9)2 | 3 | Oxalate (amorphous solid) | 45 |
| (CH3)2N—(CH2)2—NH—CO— | —N(C4H9)2 | 3 | Oxalate | 46 |

-continued

[Structure: R-substituted benzofuran with 2-$C_4H_9$-n, 3-CO-O-C6H4-O-(CH2)$_{n'}$-Am']

| R | Am' | n' | Characteristics | Ex. |
|---|---|---|---|---|
| $H_5C_2-CO_2-$ | N-methylpiperidine | 3 | Hydrochloride M.p.: 161–163° C. | 47 |
| $H_5C_2-CO_2-$ | N-methylpiperidine | 2 | Hydrochloride M.p.: 147–1503° C. | 48 |
| $(CH_3)_2N-(CH_2)_2-CO_2-$ | N-methyl-3,5-bis(ethylidene)piperidine | 3 | Dioxalate (solid) | 49 |
| $(CH_3)_2N-(CH_2)_2-CO_2-$ | N-methylpiperidine | 3 | Dihydrochloride (solid) | 50 |
| $CH_3O_2C-(CH_2)_2-NH-CO-$ | $-N(C_4H_9)_2$ | 3 | Oxalate (amorphous solid) | 51 |
| $HOCH_2-$ | N-methylpiperidine | 2 | Oxalate (amorphous solid) | 52 |
| $HOCH_2-$ | N-methylpiperidine | 3 | Hydrochloride M.p.: 173–175° C. | 53 |
| 3-(methoxycarbonyl)-N-acetylanilino | $-N(C_4H_9)_2$ | 3 | Oxalate M.p.: 80° C. | 54 |
| 3-carboxy-N-acetylanilino | $-N(C_4H_9)_2$ | 3 | Base M.p.: 130° C. | 55 |
| 4-carboxy-N-acetylanilino | $-N(C_4H_9)_2$ | 3 | Hydrochloride M.p.: 142° C. | 56 |

-continued

Structure: R-[5-benzofuran]-3-CO-O-C6H4-O-(CH2)n'-Am', with 2-C4H9-n

| R | Am' | n' | Characteristics | Ex. |
|---|---|---|---|---|
| H5C2O2C—O—CH(CH3)—CO2— | —N(C4H9)2 | 3 | Oxalate M.p.: 86° C. | 57 |
| HO-CH2CH2-N(COCH3)-CH2CH2-OH (N,N-bis(2-hydroxyethyl)acetamido) | —N(C4H9)2 | 3 | Solid M.p.: 89–91° C. | 150 |
| H5C2—CO2— | 1-methyl-3,5-bis(ethylidene)piperidinyl | 2 | Hydrochloride Solid M.p.: 133–134° C. | 156 |
| Piperidinyl-CH2CH2-O-C(O)CH3 | N-methylpiperidinyl | 3 | Hydrochloride Solid | 158 |
| HOOC— | N-methylpyrrolidinyl | 3 | Hydrochloride Amorphous | 162 |

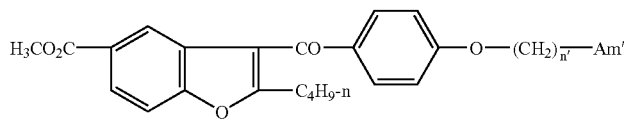

| Am' | n' | Characteristics | Ex. |
|---|---|---|---|
| —N(C4H9-n)2 | 2 | Oxalate M.p.: 88° C. | 58 |
| —N(CH3)(CH2CH2OH)(CH2CH2CH2-C6H4-NO2) | 2 | Oxalate M.p.: 124° C. | 59 |
| —N(piperazinyl)-CH3 | 3 | Base M.p.: 66–68° C. | 60 |

-continued
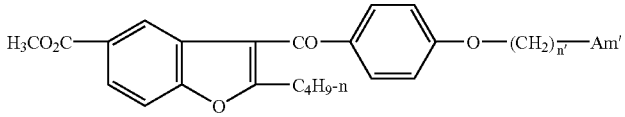
| Am' | n' | Characteristics | Ex. |
|---|---|---|---|
| 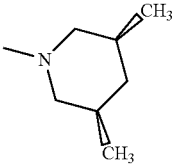 | 2 | Hydrochloride M.p.: 153° C. | 61 |
| 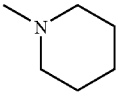 | 2 | Hydrochloride M.p.: 122° C. | 62 |
| 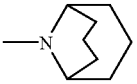 | 3 | Hydrochloride M.p.: 147° C. | 63 |
| —N(C$_2$H$_5$)$_2$ | 2 | Hydrochloride M.p.: 112° C. | 64 |
| —N(C$_2$H$_5$)$_2$ | 3 | Hydrochloride M.p.: 105° C. | 65 |
| 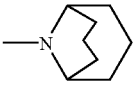 | 2 | Oxalate M.p.: 185° C. | 66 |
| 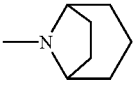 | 3 | Oxalate M.p.: 142° C. | 67 |
| 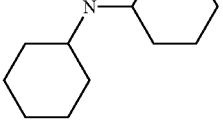 | 3 | Oxalate M.p.: 155° C. | 68 |
| 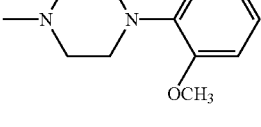 | 3 | Oxalate (amorphous powder) | 69 |
| 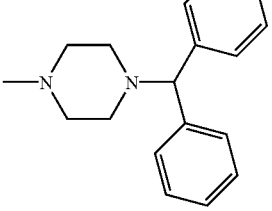 | 3 | Oxalate M.p.: 116° C. | 70 |
|  | 2 | Base M.p.: 124° C. | 71 |

-continued

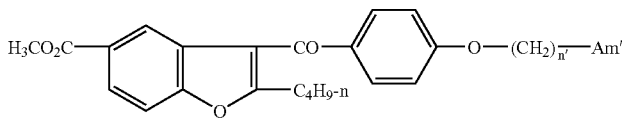

| Am' | n' | Characteristics | Ex. |
|---|---|---|---|
| [2-methyl-6,7-dimethoxy-1,2,3,4-tetrahydroisoquinolin-yl] | 3 | Oxalate<br>M.p.: 159° C. | 72 |
| [1-methyl-3,5-bis(ethylidene)piperidinyl] | 3 | Hydrochloride<br>M.p.: 135° C. | 73 |
| [1-methyl-3,5-bis(ethylidene)piperidinyl] | 2 | Hydrochloride<br>M.p.: 161° C. | 74 |
| [1-methyl-3-ethylidene-5-ethylpiperidinyl] | 2 | Hydrochloride<br>M.p.: 133° C. | 75 |
| [1-methyl-3-ethylidene-5-ethylpiperidinyl] | 3 | Oxalate<br>(amorphous<br>powder) | 76 |
| [1-methyl-3,5-bis(methylene)piperidinyl] | 3 | Hydrochloride<br>M.p.: 141° C. | 77 |
| [N-methyl-azabicyclic] | 3 | Oxalate (solid) | 78 |
| —NH—CH₂CH₂—O—(2-methoxyphenyl) | 3 | Oxalate<br>M.p.: 150–152° C. | 79 |

-continued

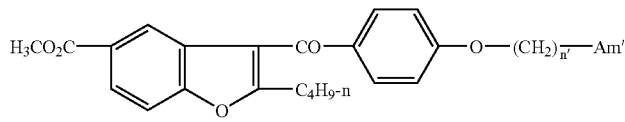

| Am' | n' | Characteristics | Ex. |
|---|---|---|---|
| ![N-ethyl-N-cyclohexyl] | 3 | Oxalate (solid) | 80 |
| ![N-methylpyrrolidine] | 2 | Hydrochloride M.p.: 108–110° C. | 81 |
| ![3,5-dimethylene-N-methylpiperidine] | 2 | Hydrochloride Solid M.p.: 153–156° C. | 157 |
| ![N-methylpyrrolidine] | 3 | Hydrochloride Solid M.p.: 131–133° C. | 159 |

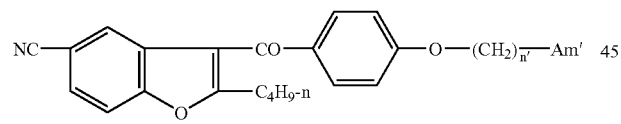

| Am' | n' | Characteristics | Ex. |
|---|---|---|---|
| —N(C₄H₉-n)—(CH₂)₄—CH₂OH | 3 | Oxalate (amorphous solid) | 82 |
| —NHC₄H₉-n | 3 | Hydrochloride M.p.: 176° C. | 83 |
| 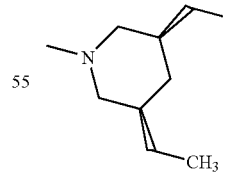 | 2 | Oxalate M.p.: 148° C. | 84 |

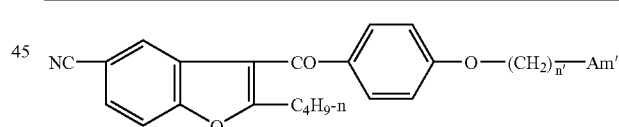

| Am' | n' | Characteristics | Ex. |
|---|---|---|---|
| ![3,5-diethylidene-N-methylpiperidine] | 3 | Oxalate M.p.: 161° C. | 85 |
| —N(C₄H₉-n)—(CH₂)₃—CO₂CH₃ | 3 | Oxalate (amorphous solid) | 86 |

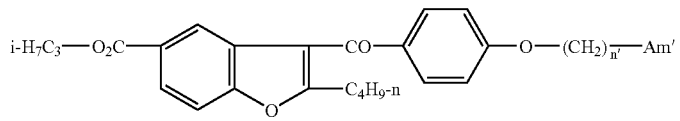

| Am' | n' | Characteristics | Ex. |
|---|---|---|---|
| —N(C₄H₉-n)₂ | 3 | Oxalate<br>M.p.: 94° C. | 87 |
| (N,N-dimethyl-2-(3,4-dimethoxyphenyl)ethylamino) | 3 | Oxalate<br>M.p.: 85° C. | 88 |
| (N-methyl-3,4-dimethoxybenzylamino) | 3 | Hydrochloride<br>(amorphous solid) | 89 |
| (4-methylpiperazinyl-N,N-diethylaminoethyl) | 3 | Trihydrochloride<br>M.p.: 242° C. | 90 |
| (N-methylcyclohexylamino) | 3 | Oxalate<br>M.p.: 163° C. | 91 |
| (N-methylbenzylamino) | 3 | Hydrochloride<br>(amorphous solid) | 92 |
| (N-methyl-2-(3,4-dimethoxyphenyl)ethylamino) | 3 | Hydrochloride<br>(amorphous solid) | 93 |
| (N-methyl-2-(2-methoxyphenoxy)ethylamino) | 3 | Hydrochloride<br>M.p.: 116° C. | 94 |
| (N-methyl-N-cyclohexyl-cyclohexylamino) | 2 | Oxalate<br>M.p.: 71° C.<br>(amorphous powder) | 95 |
| (morpholino) | 3 | Base<br>M.p.: 94° C. | 96 |

-continued

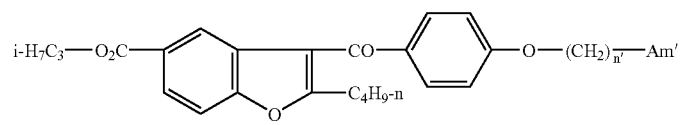

| Am' | n' | Characteristics | Ex. |
|---|---|---|---|
| (N-methylpiperidine with two =CH-CH3 groups) | 5 | Oxalate M.p.: 120° C. | 97 |
| (N-methylpiperidine with two =CH-CH3 groups) | 4 | Oxalate M.p.: 121° C. | 98 |
| dicyclohexyl(methyl)amine | 3 | Hydrochloride M.p.: 129° C. | 99 |
| —N(1-methylpiperidin-4-yl)—OH | 3 | Oxalate (amorphous white solid) | 100 |
| N-methylpiperidine | 3 | Hydrochloride M.p.: 158° C. | 101 |
| —NH—C$_4$H$_9$-n | 2 | Oxalate M.p.: 188° C. | 102 |
| —NH—C$_4$H$_9$-n | 3 | Oxalate M.p.: 170° C. | 103 |
| —N(C$_4$H$_9$-n)$_2$ | 2 | Oxalate (amorphous white solid) | 104 |
| quinuclidine | 2 | Oxalate M.p.: 86° C. | 105 |
| quinuclidine | 2 | Hydrochloride M.p.: 89° C. | 106 |
| quinuclidine | 3 | Hydrochloride M.p.: 179° C. | 107 |
| quinuclidine | 3 | Oxalate M.p.: 150° C. | 108 |

-continued

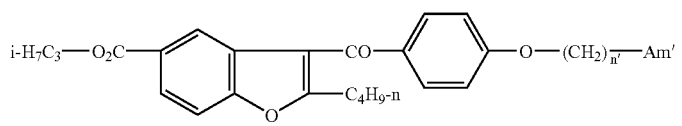

| Am' | n' | Characteristics | Ex. |
|---|---|---|---|
| 1-methyl-3,5-bis(ethylidene)piperidine | 2 | Hydrochloride M.p.: 156° C. | 109 |
| 1-methyl-3,5-bis(ethylidene)piperidine | 3 | Oxalate M.p.: 127° C. | 110 |
| 1-methyl-3,5-bis(ethylidene)piperidine | 3 | Hydrochloride M.p.: 86° C. | 111 |
| 1-methyl-3,5-dimethylidenepiperidine (trans) | 3 | Hydrochloride M.p.: 161° C. | 112 |
| 1-methyl-3,5-dimethylidenepiperidine | 3 | Hydrochloride M.p.: 172° C. | 113 |
| 1-methyl-3-ethylidene-5-ethylpiperidine | 3 | Hydrochloride M.p.: 146° C. | 114 |
| 1-methyl-3,3-diethylpiperidine | 3 | Hydrochloride M.p.: 154° C. | 115 |

-continued

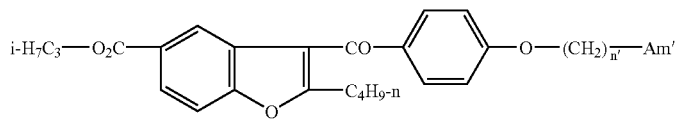

| Am' | n' | Characteristics | Ex. |
|---|---|---|---|
| (1-methyl-5-ethyl-3-ethylidenepiperidine) | 3 | Hydrochloride M.p.: 117° C. | 116 |
| (ethyl 1-methylpiperidine-4-carboxylate) | 3 | Hydrochloride (solid) | 117 |

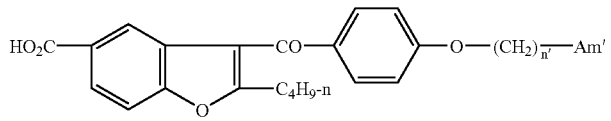

| Am' | n' | Characteristics | Ex. |
|---|---|---|---|
| (6,7-dimethoxy-2-methyl-1,2,3,4-tetrahydroisoquinoline) | 3 | Base (amorphous solid) | 118 |
| (1-methyl-4-(2-methoxyphenyl)piperazine) | 3 | Base M.p.: 108° C. | 119 |
| (N-(2-hydroxyethyl)-N-methyl-3-(4-nitrophenyl)propylamine) | 2 | Base M.p.: 80° C. | 120 |
| (1-methyl-4-(diphenylmethyl)piperazine) | 2 | Base (amorphous white solid) | 121 |

-continued

Structure: HO₂C-[benzofuran with C₄H₉-n at 2-position]-CO-O-[phenyl]-O-(CH₂)ₙ'-Am'

| Am' | n' | Characteristics | Ex. |
|---|---|---|---|
| 1-methyl-3,5-bis(ethylidene)piperidine | 2 | Base (amorphous white solid) | 122 |
| 1-methyl-3,5-bis(ethylidene)piperidine | 3 | Base (amorphous white solid) | 123 |
| 1-methylquinuclidine | 2 | Hydrochloride (solid) | 124 |
| 4-methylpiperazin-1-yl (N-methylpiperazine) | 3 | Base M.p.: 95° C. | 125 |
| 1-methylpiperidine | 2 | Base (amorphous solid) | 126 |
| 1-methylpiperidine | 3 | Base (amorphous solid) | 127 |
| —N(C₂H₅)₂ | 2 | Base M.p.: 73° C. | 128 |
| 4-[2-(diethylamino)ethyl]piperazin-1-yl | 3 | Trihydrochloride M.p.: >200° C. (degradation) | 129 |
| —NH-CH₂CH₂-O-(2-methoxyphenyl) | 3 | Hydrochloride M.p.: 156° C. | 130 |
| 1,3,5-trimethylpiperidine (stereo) | 3 | Base (amorphous powder) | 131 |
| 1-methyl-3,3-diethylpiperidine | 3 | Hydrochloride M.p.: 106° C. | 132 |

-continued

[Structure: HO₂C-benzofuran(C₄H₉-n)-CO-O-C₆H₄-O-(CH₂)n'-Am']

| Am' | n' | Characteristics | Ex. |
|---|---|---|---|
| N-methyl-3,5-dimethylenepiperidine | 3 | Hydrochloride M.p.: 116° C. | 133 |
| N-methylmorpholine | 3 | Base M.p.: 85° C. | 134 |
| N-methyl-3,5-di(ethylidene)piperidine | 5 | Base M.p.: 167° C. | 135 |
| N-methyl-N-cyclohexylcyclohexylamine | 2 | Hydrochloride M.p.: 173° C. | 136 |
| N-methyl-3,5-di(ethylidene)piperidine | 4 | Base M.p.: 100° C. | 137 |
| azabicyclic amine | 3 | Hydrochloride (solid) | 138 |
| azabicyclic amine | 3 | Hydrochloride M.p.: 191° C. | 139 |
| N-methyl-N-cyclohexylcyclohexylamine | 3 | Hydrochloride (amorphous powder) | 140 |
| N-methylazabicyclic | 2 | Hydrochloride (solid) | 141 |
| —N(C₄H₉)₂ | 2 | Base (amorphous solid) | 142 |
| —N(C₄H₉)₂ | 3 | Hydrochloride (amorphous powder) | 143 |

-continued
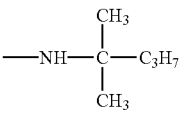
| Am' | n' | Characteristics | Ex. |
|---|---|---|---|
|  | 3 | Hydrochloride (amorphous powder) | 144 |
| —N(C$_2$H$_5$)$_2$ | 3 | Base M.p.: 83° C. | 145 |
| 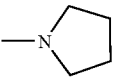 | 2 | Hydrochloride M.p.: 188–190° C. | 146 |
| —NH—C$_5$H$_9$-neo | 3 | Base M.p.: 188° C. | 147 |
| 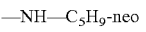 | 2 | Base (amorphous solid) | 148 |
The compounds listed below were also prepared.
| Compound | Characteristics | Example |
|---|---|---|
| 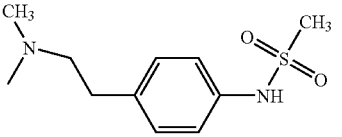 | Oxalate Solid M.p.: 130° C. | 152 |
| 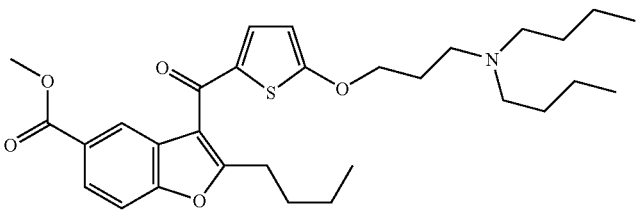 | Oil | 153 |
| 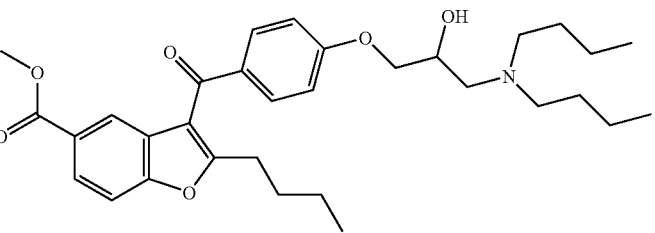 | Oxalate Ice (NMR spectrum below) | 154 |

-continued

| Compound | Characteristics | Example |
|---|---|---|
| (structure) | Oxalate Powder M.p.: 87–88° C. | 155 |
| (structure) | Hydrochloride Solid M.p.: 140–142° C. | 160 |
| (structure) | Hydrochloride Solid M.p.: 141–143° C. | 161 |

EXAMPLE 149

A capsule containing the following ingredients was prepared according to known pharmaceutical techniques:

| Ingredient | Mg |
|---|---|
| Compound of the invention | 100.0 |
| Starch | 99.5 |
| Colloidal silica | 0.5 |

$^1$H NMR Spectra at 200 MHz

EXAMPLE 153

Solvent: DMSO

δ (ppm): 6.9–8.2 (unresolved peak, 7H); 4.85 (broad singlet, 1H); 3.7–4.3 (unresolved peak, 6H); 2.2–3.0 (unresolved peak, 8H); 0.6–1.8 (unresolved peak, 21H)

EXAMPLE 154

Solvent: DMSO

δ (ppm): 6.7–7.5 (unresolved peak, 7H); 4.45 (singlet, 2H); 3.7–4.3 (unresolved peak, 6H); 3.2–3.5 (unresolved peak, 2H); 2.95 (broad double doublet, 4H); 2.80 (triplet, 2H); 0.7–3.3 (unresolved peak, 21H)

EXAMPLE 158

Solvent: DMSO

δ (ppm): 6.9–8.2 (unresolved peak, 7H); 2.6–4.8 (unresolved peak, 16H); 0.9–2.3 (unresolved peak, 18H); 0.78 (triplet, 3H)

EXAMPLE 162

Solvent: DMSO

δ (ppm): 6.9–8.2 (unresolved peak, 7H); 3.0–4.4 (unresolved peak, 8H); 2.80 (triplet, 2H); 1.0–2.3 (unresolved peak, 10H); 0.78 (triplet, 3H)

What is claimed is:

1. Benzofuran or benzothiophene compounds of general formula:

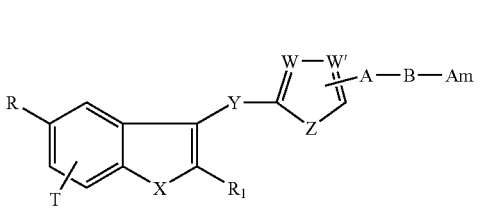

and also their pharmaceutically acceptable salts, in which formula:

A represents —O—, —S— or

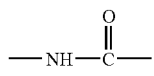

B represents a linear or branched $C_1$–$C_5$ alkylene group optionally substituted with a hydroxyl group, T represents hydrogen or a $C_1$–$C_4$ alkyl radical R represents the cyano or hydroxymethyl group an oxime group of formula:

$R_4$—O—N=CH— in which $R_4$ represents a $C_1$–$C_4$ alkyl group a carboxyl group of general formula:

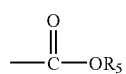 (a)

in which $R_5$ represents hydrogen or an alkali metal atom, a linear or branched $C_1$–$C_{10}$ alkyl group or a $C_3$–$C_6$ cycloalkyl group, or $R_5$ represents the group of general formula:

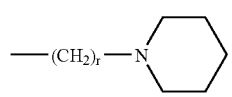 (a-1)

in which r represents 1 to 4 a carboxyl group of general formula:

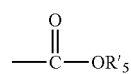 (b)

in which $R'_5$ represents a piperidinyl group optionally N-substituted with a $C_1$–$C_4$ alkyl group or one of the groups of general formula:

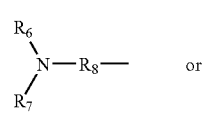 (c)

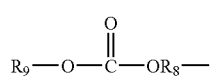 (d)

in which $R_6$ and $R_7$, which may be identical or different, represent a $C_1$–$C_4$ alkyl group, $R_8$ represents a linear or branched $C_1$–$C_6$ alkylene group, and $R_9$ represents hydrogen, an alkali metal atom or a $C_1$–$C_4$ alkyl group, an aminocarbonyl group of formula:

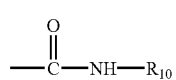 (e)

in which $R_{10}$ represents hydrogen, a $C_1$–$C_4$ alkyl, hydroxyl or amino group, a group (c) above or one of the groups:

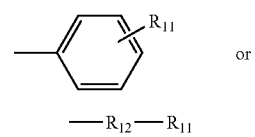 (f)

or

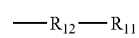 (g)

in which $R_{11}$ represents a group (a) and $R_{12}$ represents a $C_1$–$C_6$ alkylene radical, a group of formula:

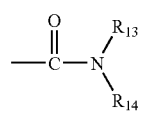 (h)

in which $R_{13}$ and $R_{14}$, which may be identical or different, represent a $C_1$–$C_4$ alkyl radical or a $C_1$–$C_4$ hydroxyalkyl group, one of the groups of formula below:

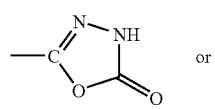 (j)

or

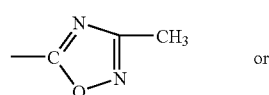 (k)

or

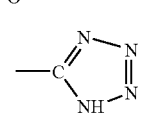 (l)

$R_1$ represents a $C_1$–$C_6$ alkyl, or a group of formula:

—(CH$_2$)$_p$—R$_{11}$  (m)

in which $R_{11}$ has the same meaning as previously and p represents 1 to 4,

Am represents a nitrogenous group of formula:

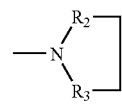 (Am$_1$)

in which:

$R_2$ represents hydrogen, a linear or branched $C_1$–$C_6$ alkyl group optionally substituted with a hydroxyl group, a group (m), a $C_3$–$C_6$ cycloalkyl group or a benzyl group, $R_3$ represents a linear or branched $C_1$–$C_6$ alkyl group optionally substituted with a hydroxyl group, a $C_3$–$C_6$ cycloalkyl group, a group (m), a benzyl group or a phenyl group of formula:

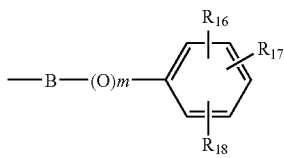
(n)

$R_{16}$, $R_{17}$ and $R_{18}$, which may be identical or different, represent hydrogen, or a hydroxyl, nitro, amino, $C_1$–$C_4$ alkoxy or $C_1$–$C_4$ alkylsulfonamido group, m in represents 0 or 1, $R_2$ and $R_3$, when they ore taken together, represent a linear or branched $C_3$–$C_{10}$ alkylene group optionally substituted with the hydroxyl group, with a group (a) or with a group (m) and optionally interrupted by —O—, W, W' and Z are such that:
when W and W', which are identical, represent CH, Z represents —O— or —S—,
when W represents CH and W' represents C—$R_{20}$, Z represents

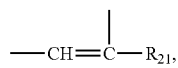

$R_{20}$ and $R_{21}$ being identical or different and representing hydrogen, a halogen atom, a $C_1$–$C_4$ alkyl radical, or a $C_1$–$C_4$ alkoxy radical, X represents —O— or —S—, Y represents a —CO— or —CH$_2$— radical, or a radical of formula

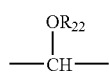
(73)

in which $R_{22}$ represents hydrogen, a $C_1$–$C_4$ alkyl radical or an acyl radical of formula:

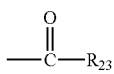
(74)

in which $R_{23}$ represents a $C_1$–$C_4$ alkyl radical, or Y represents

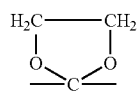

it being understood that the combination of the R, $R_1$ and Am groups contains 0, 1 or 2 groups (a), these benzofuran or benzothiophene derivatives being in the form of individual isomers or of a mixture thereof,
thereof.

2. Benzofuran or benzothiophene derivatives according to claim 1, in which R represents the isopropoxycarbonyl group.

3. Benzofuran or benzothiophene derivatives according to claim 2, in which Am represents a diethylpiperidinyl group.

4. Benzofuran or benzothiophene derivatives according to claim 3, in which Y represents the —CO— radical.

5. Benzofuran or benzothiophene derivatives according to claim 4, in which

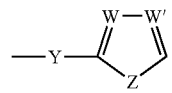

represents the benzoyl radical.

6. Benzofuran or benzothiophene derivatives according to claim 5, in which:

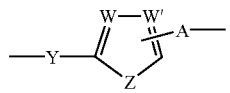

represents the 4-oxybenzoyl radical.

7. Benzofuran or benzothiophene derivatives according to claim 6, in which the chain:

A-B-Am is located at position 4.

8. Benzofuran or benzothiophene derivatives according to claim 7, in which $R_1$ represents n-butyl, B represents the propylene group and Am represents a diethylpiperidinyl group.

9. Benzofuran or benzothiophene derivatives according to claim 8, in which the diethylpiperidinyl group is the 3,5-diethylpiperidinyl group.

10. Benzofuran or benzothiophene derivatives according to claim 1, in which the pharmaceutically acceptable salt is chosen from oxalate, maleate, fumarate, methanesulfonate, benzoate, ascorbate, pamoate, succinate, hexamate, bismethylenesalicylate, ethanedisulfonate, acetate, propionate, tartrate, salicylate, citrate, gluconate, lactate, malate, cinnamate, aspartate, palmitate, stearate, itaconate, glycolate, p-aminobenzoate, glutamate, benzenesulfonate, p-toluenesulfonate and theophyllineacetate salts and the salts formed from an amino acid.

11. Benzofuran or benzothiophene compounds according to claim 1 in which the pharmaceutically acceptable salt is chosen from the hydrochloride, hydrobromide, sulfate, sulfamate, phosphate and nitrate salts.

12. Benzofuran or benzothiophene compounds according to claim 9 in which the pharmaceutically acceptable salt is chosen from oxalate, maleate, fumarate, methanesulfonate, benzoate, ascorbate, pamoate, succinate, hexamate, bismethylenesalicylate, ethanedisulfonate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulfonate, p-toluenesulfonate and theophyllineacetate salts and the salts formed from an amino acid.

13. Benzofuran or benzothiophene compounds according to claim 9 in which the pharmaceutically acceptable salt is chosen from hydrochloride, hydrobromide, sulfate, sulfamate, phosphate and nitrate salts.

14. Benzofuran or benzothiophene compounds according to claim 10 in which the salt formed from an amino acid is a lysine or histidine salt.

15. Benzofuran or benzothiophene compounds according to claim 12 in which the salt formed from an amino acid is a lysine or histidine salt.

16. Process for the preparation of benzofuran or benzothiophene derivatives according to claim 1, in which Y represents the —CO— group, $R_1$ and $(Am_1)$ comprise no carboxylic or alkali metal carboxylate group, $R_{16}$ and/or $R_{17}$ and/or $R_{18}$ are different from the amino group or from a $C_1$–$C_4$ alkylsulfonamido group and R represents a cyano or hydroxymethyl group, the group (k) or a group (a) in which $R_5$ represents a $C_1$–$C_{10}$ alkyl or $C_3$–$C_6$ cycloalkyl group, wherein a ketone compound of general formula:

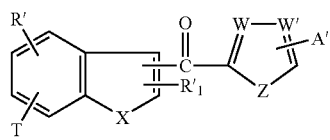

(2)

in which $R'_1$ represents a $C_1$–$C_6$ alkyl, $C_3$–$C_6$ cycloalkyl, phenyl or benzyl group or a group (m) comprising no carboxylic or alkali metal carboxylate group, T, W, W', X and Z have the same meaning as in claim 1, A' represents OH, SH or $NH_2$ and R' represents a cyano or hydroxymethyl group, the group (k) or a —$CO_2R''_5$ group in which $R''_5$ represents a $C_1$–$C_{10}$ alkyl or $C_3$–$C_6$ cycloalkyl radical, is reacted, in the presence of a basic agent, with a compound of general formula:

$R_{24}$-B-Am' (3)

in which Am' represents a group $(Am_1)$ as defined in claim 1, this group comprising no carboxylic or alkali metal carboxylate group, —$R_{16}$ and/or $R_{17}$ and/or $R_{18}$ are different from an amino group or a $C_1$–$C_4$ alkylsulfonamido group, B has the same meaning as in claim 1 and $R_{24}$ represents:

either a halogen atom, or a $C_1$–$C_4$ alkylsulfonyloxy or $C_6$–$C_{10}$arylsulfonyloxy radical, which makes it possible to obtain, in the free base form, the desired compounds in which A represents —O— or —S—, or a halocarbonyl group, which makes it possible to obtain, in the free base form, the desired compounds in which A represents —NH—CO—, the compounds in the free base form thus obtained possibly being, if necessary, treated with a suitable organic or inorganic acid, to form a pharmaceutically acceptable salt.

17. Process for the preparation of benzofuran or benzothiophene derivatives according to claim 1, in which Y represents the —CO— group, $R_1$ and $(Am_2)$ comprise no carboxylic or alkali metal carboxylate group, $R_{16}$ and/or $R_{17}$ and/or $R_{18}$ are different from the amino group or from a $C_1$–$C_4$ alkylsulfonamido group and R represents the cyano group, the group (k), an $R_4$—O—N═CH— group or a group (a) in which $R_5$ represents a $C_1$–$C_{10}$ alkyl or $C_3$–$C_6$ cycloalkyl group, wherein a compound of general formula:

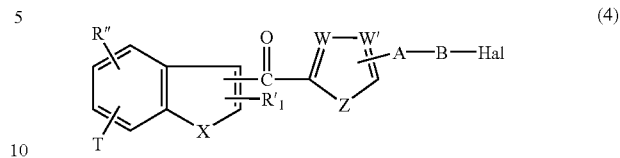

(4)

in which A, B, T, X, W, W' and Z have the same meaning as in claim 1, $R_{11}$ represents a $C_1$–$C_6$ alkyl group, a $C_3$–$C_6$ cycloalkyl, phenyl or benzyl group or a group (m) comprising no carboxylic or alkali metal carboxylate group and R" represents the cyano group, the group (k), an $R_4$—O—N═CH— group or a —$CO_2R''_5$ group in which $R''_5$ represents a $C_1$–$C_{10}$ alkyl or $C_3$–$C_6$ cycloalkyl group and Hal represents a halogen atom, is reacted with a compound of general formula:

H-Am' (5)

optionally in the form of a salt, in which Am' represents a group $(Am_1)$ or $(Am_2)$ as defined in claim 1, this group comprising no carboxylic or alkali metal carboxylate group, $R_{16}$ and/or $R_{17}$ and/or $R_{18}$ are different from an amino group or a $C_1$–$C_4$ alkylsulfonamido group, the reaction taking place in the presence of a basic agent or an excess of amine of formula (5) in the basic form, which gives the desired compounds in the free base form, which base can be reacted, if necessary, with a suitable organic or inorganic acid, to form a pharmaceutically acceptable salt.

18. Process for the preparation of benzofuran or benzothiophene derivatives according to claim 1, in which Y represents the —CO— group, $R_1$ and $(Am_1)$ comprise no carboxylic or alkali metal carboxylate group, $R_{16}$ and/or $R_{17}$ and/or $R_{18}$ are different from the amino group or from a $C_1$–$C_4$ alkylsulfonamido group and R represents the cyano group, an $R_4$—O—N═CH— group, a group (a) in which $R_5$ represents a $C_1$–$C_{10}$ alkyl or $C_3$–$C_6$ cycloalkyl group or else the group (k), wherein a compound of general formula:

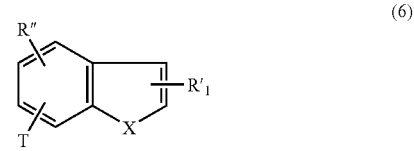

(6)

in which T and X have the same meaning as in claim 1, R" represents the cyano group, the group (k), an $R_4$—O—N═CH— group or a —$CO_2R''_5$ group in which $R''_5$ represents a $C_1$–$C_{10}$ alkyl or $C_3$–$C_6$ cycloalkyl group and $R'_1$ represents a $C_1$–$C_6$ alkyl group, a $C_3$–$C_6$ cycloalkyl, phenyl or benzyl group or a group (m) comprising no carboxylic or alkali metal carboxylate group, is reacted with a halide of general formula:

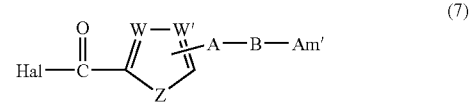

(7)

in which A, B, W, W' and Z have the same meaning as in claim 1, Hal represents a halogen atom and Am' represents a group (Am$_1$) as defined in claim 1, this group comprising no carboxylic or alkali metal carboxylate group, R$_{16}$ and/or R$_{17}$ and/or R$_{18}$ are different from an amino group or a C$_1$–C$_4$ alkylsulfonamido group, the reaction optionally taking place in the presence of a Lewis acid, which gives the desired compounds in the free base form, which base can be reacted, if necessary, with an organic or inorganic acid, to form a pharmaceutically acceptable salt.

19. Process for the preparation of benzofuran or benzothiophene derivatives according to claim 1, in which Y represents the —CO— group, R$_1$ and (Am$_1$) comprise no carboxylic or alkali metal carboxylate group, R$_{16}$ and/or R$_{17}$ and/or R$_{18}$ are different from the amino group or from a C$_1$–C$_4$ alkylsulfonamido group and R represents the group (j), wherein a compound of formula:

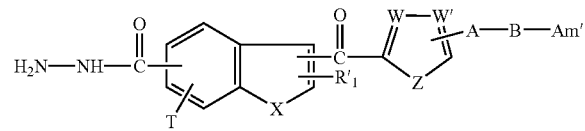

(9)

in which A, B, T, W, W', X and Z have the same meaning as in claim 1, R'$_1$ represents a C$_1$–C$_6$ alkyl, C$_3$–C$_6$ cycloalkyl, phenyl or benzyl group or a group (m) comprising no carboxylic or alkali metal carboxylate group and Am' represents a group (Am$_1$) as defined in claim 1, this group comprising no carboxylic or alkali metal carboxylate group, R$_{16}$ and/or R$_{17}$ and/or R$_{18}$ are different from an amino group or a C$_1$–C$_4$ alkylsulfonamido group, is reacted with phosgene, which gives the desired compounds in the hydrochloride form, which hydrochloride can be treated, if necessary, with a basic agent, such as an alkali metal hydroxide or an alkali metal carbonate, which gives the desired compounds in the free base form, which base can be reacted, if necessary, with an organic or inorganic acid, to form a pharmaceutically acceptable salt.

20. Process for the preparation of benzofuran or benzothiophene derivatives according to claim 1, in which Y represents the —CO— group, R$_1$ and (Am$_1$) comprise no carboxylic or alkali metal carboxylate group, R$_{16}$ and/or R$_{17}$ and/or R$_{18}$ are different from the amino group or from a C$_1$–C$_4$ alkylsulfonamido group and R represents a group (b) in which R'$_5$ represents a group (c) of the primary dialkylaminoalkyl type, wherein a compound of formula:

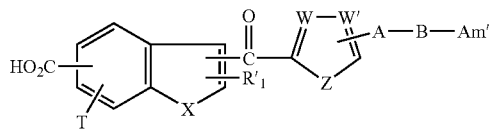

(10)

in which A, B, T, X, W, W', X and Z have the same meaning as in claim 1, R$_{11}$ represents a C$_1$–C$_6$ alkyl, C$_3$–C$_6$ cycloalkyl, phenyl or benzyl group or a group (m) comprising no carboxylic or alkali metal carboxylate group and Am' represents a group (Am$_1$) as defined in claim 1, this group comprising no carboxylic or alkali metal carboxylate group, R$_{16}$ and/or R$_{17}$ and/or R$_{18}$ are different from an amino group or a C$_1$–C$_4$ alkylsulfonamido group, after protection of the amino functional group when Am' represents a group (Am$_1$) in which R$_2$ represents hydrogen, is reacted with an alcohol of general formula:

(11)

in which R$_6$ and R$_7$ have the same meaning as in claim 1 and R$_8$ represents a linear C$_1$–C$_8$ alkylene group, the reaction taking place in the presence of carbonyldiimidazole and 1,8-diazabicyclo[5.4.0]undec-7-ene, and then, if necessary, the compound formed is deprotected, which gives the desired compounds in the free base form, which base can be treated, if necessary, with a suitable organic or inorganic acid, to produce a pharmaceutically acceptable salt.

21. Process for the preparation of benzofuran or benzothiophene derivatives according to claim 1, in which Y represents the —CO— group, R$_1$ and (Am$_1$) comprise no carboxylic or alkali metal carboxylate group, R$_{16}$ and/or R$_{17}$ and/or R$_{18}$ are different from the amino group or from a C$_1$–C$_4$ alkylsulfonamido group and R represents a group (b) in which R'$_5$ represents a group (c) of the secondary or tertiary dialkylaminoalkyl type, wherein a compound of formula:

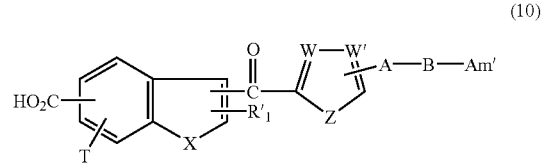

(10)

in which A, B, T, X, W, W' and Z have the same meaning as in claim 1, R'$_1$ represents a C$_1$–C$_6$ alkyl, C$_3$–C$_6$ cycloalkyl, phenyl or benzyl group or a group (m) comprising no carboxylic or alkali metal carboxylate group and Am' represents a group (Am$_1$) as defined in claim 1, this group comprising no carboxylic or alkali metal carboxylate group, R$_{16}$ and/or R$_{17}$ and/or R$_{18}$ are different from an amino group or a C$_1$–C$_4$ alkylsulfonamido group, after protection of the amino functional group when Am' represents a group (Am$_1$) in which R$_2$ represents hydrogen, is reacted with a halogenating agent, to produce an acyl halide, which is subsequently treated with an alcohol of formula:

(11)

in which R$_6$ and R$_7$ have the same meaning as in claim 1 and R$_8$ represents a secondary or tertiary C$_2$–C$_6$ alkylene group, and then, if necessary, the compound formed is deprotected, which gives the desired compounds in the hydrohalide form or in the free base form when the compound of formula (10) is in excess, which hydrohalide can be treated, if necessary, with a basic agent, such as an alkali metal hydroxide or an alkali metal carbonate, to produce the desired compounds in the free base form, the free base thus formed possibly being, if necessary, treated with a suitable organic or inorganic acid, to produce a pharmaceutically acceptable salt.

22. Process for the preparation of benzofuran or benzothiophene derivatives according to claim 1, in which Y represents the —CO— group, $R_1$ and $(Am_1)$ comprise no carboxylic or alkali metal carboxylate group, $R_{16}$ and/or $R_{17}$ and/or $R_{18}$ are different from the amino group or from a $C_1$–$C_4$ alkylsulfonamido group and R represents either a group (a) in which $R_5$ represents a $C_1$–$C_{10}$ alkyl or $C_3$–$C_6$ cycloalkyl group, or a group (b) in which $R'_5$ represents a piperidinyl group optionally N-substituted with a $C_1$–$C_4$ alkyl group or in which $R'_5$ represents a group (d) comprising no carboxylic or alkali metal carboxylate group, wherein a compound of formula:

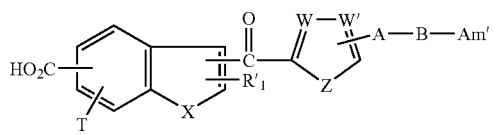

(10)

in which A, B, T, X, W, W' and Z have the same meaning as in claim 1, $R'_1$ represents a $C_1$–$C_6$ alkyl, $C_3$–$C_6$ cycloalkyl, phenyl or benzyl group or a group (m) comprising no carboxylic or alkali metal carboxylate group and Am' represents a group $(Am_1)$ as defined in claim 1, this group comprising no carboxylic or alkali metal carboxylate group, $R_{16}$ and/or $R_{17}$ and/or $R_{18}$ are different from an amino group or a $C_1$–$C_4$ alkylsulfonamido group, after protection of the amino functional group when Am' represents a group $(Am_1)$ in which $R_2$ represents hydrogen, is reacted with a halogenating agent, to produce an acyl halide, which is subsequently treated with an alcohol of general formula:

R'''$_5$—OH (12)

in which R'''$_5$ represents a $C_1$–$C_{10}$ alkyl or $C_3$–$C_6$ cycloalkyl group or a group (b) in which $R'_5$ represents a piperidinyl group optionally N-substituted with a $C_1$–$C_4$ alkyl group or $R'_5$ represents a group (d) comprising no carboxylic or alkali metal carboxylate group, and then, if necessary, the compound formed is deprotected, which gives the desired compounds in the hydrohalide form or in the free base form when the compound of formula (10) is in excess, which hydrohalide can be treated, if desired, with a basic agent, such as an alkali metal hydroxide or an alkali metal carbonate, to produce the desired compounds in the free base form, the free base thus formed possibly being, if necessary, treated with a suitable organic or inorganic acid, to produce a pharmaceutically acceptable salt.

23. Process for the preparation of benzofuran or benzothiophene derivatives according to claim 1, in which Y represents the —CO— group, $R_1$ and $(Am_1)$ comprise no carboxylic or alkali metal carboxylate group, $R_{16}$ and/or $R_{17}$ and/or $R_{18}$ are different from the amino group or from a $C_1$–$C_4$ alkylsulfonamido group and R represents a group (e) in which $R_{10}$ represents a group (f) comprising no carboxylic or alkali metal carboxylate group, wherein a compound of formula:

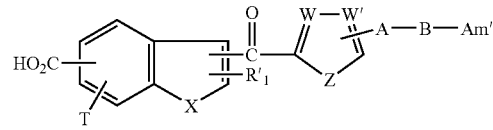

(10)

in which A, B, T, X, W, W' and Z have the same meaning as in claim 1, $R'_1$ represents a $C_1$–$C_6$ alkyl, $C_3$–$C_6$ cycloalkyl, phenyl or benzyl group or a group (m) comprising no carboxylic or alkali metal carboxylate group and Am' represents a group $(Am_1)$ as defined in claim 1, this group comprising no carboxylic or alkali metal carboxylate group, $R_{16}$ and/or $R_{17}$ and/or $R_{18}$ are different from an amino group or a $C_1$–$C_4$ alkylsulfonamido group, after protection of the amine functional group when Am' represents a group $(Am_1)$ in which $R_2$ represents hydrogen, is reacted with a halogenating agent, to produce an acyl chloride, which is subsequently treated with a compound of formula:

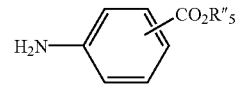

(13)

in which R''$_5$ represents a $C_1$–$C_{10}$ alkyl or $C_3$–$C_6$ cycloalkyl radical, and then, if necessary, the compound formed is deprotected, which gives, in the free base form, the desired compounds in which $R_{10}$ represents a group (f) in which the $R_{11}$ group represents a group (a) in which $R_5$ represents a $C_1$–$C_4$ alkyl or $C_3$–$C_6$ cycloalkyl group, the free base thus formed possibly being, if necessary, treated with a suitable organic or inorganic acid, to form a pharmaceutically acceptable salt.

24. Process for the preparation of benzofuran or benzothiophene derivatives according to claim 1, in which Y represents the —CO— group, $R_1$ and $(Am_1)$ comprise no carboxylic or alkali metal carboxylate group, $R_{16}$ and/or $R_{17}$ and/or $R_{18}$ are different from the amino group or from a $C_1$–$C_4$ alkylsulfonamido group and R represents a group (e) in which $R_{10}$ represents a $C_1$–$C_4$ alkyl group, an amino group or a group (c), wherein a compound of formula:

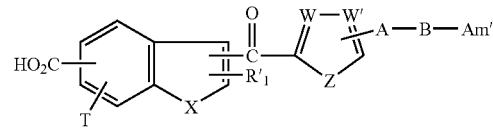

(10)

in which A, B, T, X, W, W' and Z have the same meaning as in claim 1, $R'_1$ represents a $C_1$–$C_6$ alkyl, $C_3$–$C_6$ cycloalkyl, phenyl or benzyl group or a group (m) comprising no carboxylic or alkali metal carboxylate group and Am' represents a group $(Am_1)$ as defined in claim 1, this group comprising no carboxylic or alkali metal carboxylate group, $R_{16}$ and/or $R_{17}$ and/or $R_{18}$ are different from an amino group or a $C_1$–$C_4$ alkylsulfonamido group, after protection of the amine functional group when Am' represents a group $(Am_1)$ in which $R_2$ represents hydrogen, is reacted with a halogenating agent, to produce an acyl halide, which is subsequently treated with an amine of general formula:

 (14)

or

 (15)

in which $R_6$, $R_7$ and $R_8$ have the same meaning as in claim 1 and $R'_{10}$ represents a $C_1$–$C_4$ alkyl or amino radical, and then, if necessary, the compound formed is deprotected, which gives, optionally after basic treatment, the desired compound of formula (1) in the hydrohalide form or in the free base form when the compound of formula (10) is in excess, which hydrohalide can be treated, if necessary, with a basic agent, such as an alkali metal hydroxide or an alkali metal carbonate, to produce the desired compounds in the free base form, which base can, if necessary, be reacted with a suitable organic or inorganic acid, to form a pharmaceutically acceptable salt.

25. Process for the preparation of benzofuran or benzothiophene derivatives according to claim 1, in which Y represents the —CO— group, $R_1$ and $(Am_1)$ comprise no carboxylic or alkali metal carboxylate group, $R_{16}$ and/or $R_{17}$ and/or $R_{18}$ are different from the amino group or from a $C_1$–$C_4$ alkylsulfonamido group and R represents a group (e) in which $R_{10}$ represents a group (g) comprising no carboxylic or alkali metal carboxylate group, wherein a compound of formula:

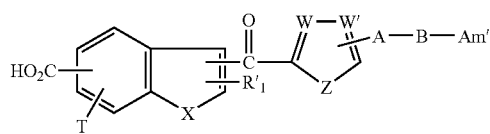 (10)

in which A, B, T, X, W, W' and Z have the same meaning as in claim 1, $R'_1$ represents a $C_1$–$C_6$ alkyl, $C_3$–$C_6$ cycloalkyl, phenyl or benzyl group or a group (m) comprising no carboxylic or alkali metal carboxylate group and Am' represents a group $(Am_1)$ as defined in claim 1, this group comprising no carboxylic or alkali metal carboxylate group, $R_{16}$ and/or $R_{17}$ and/or $R_{18}$ are different from an amino group or a $C_1$–$C_4$ alkylsulfonamido group, after protection of the amine functional group when Am' represents a group $(Am_1)$ in which $R_2$ represents hydrogen, is reacted with a salt of a compound of general formula:

 (16)

in which $R_{12}$ has the same meaning as in claim 1 and $R'_{11}$ represents a $C_1$–$C_4$ alkyl or $C_3$–$C_6$ cycloalkyl radical, the reaction taking place in the presence of an acid scavenger, and then, if necessary, the compound formed is deprotected, which gives, in the free base form, the desired compounds in which $R_{10}$ represents a group (g) in which the $R_{11}$ group represents a group (a) in which $R_5$ represents a $C_1$–$C_4$ alkyl or $C_3$–$C_6$ cycloalkyl group, the free base thus formed possibly being, if necessary, treated with a suitable organic or inorganic acid, to produce a pharmaceutically acceptable salt.

26. Process for the preparation of benzofuran or benzothiophene derivatives according to claim 1, in which Y represents the —CO— group, $R_1$ and $(Am_1)$ comprise no carboxylic or alkali metal carboxylate group, $R_{16}$ and/or $R_{17}$ and/or $R_{18}$ are different from the amino group or from a $C_1$–$C_4$ alkylsulfonamido group and R represents a group (h), wherein a compound of formula:

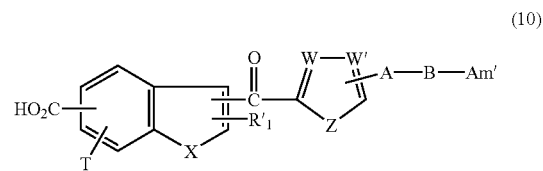 (10)

in which A, B, T, X, W, W' and Z have the same meaning as in claim 1, $R'_1$ represents a $C_1$–$C_6$ alkyl, $C_3$–$C_6$ cycloalkyl, phenyl or benzyl group or a group (m) comprising no carboxylic or alkali metal carboxylate group and Am' represents a group $(Am_1)$ as defined in claim 1, this group comprising no carboxylic or alkali metal carboxylate group, $R_{16}$ and/or $R_{17}$ and/or $R_{18}$ are different from an amino group or a $C_1$–$C_4$ alkylsulfonamido group, after protection of the amine functional group when Am' represents a group $(Am_1)$ in which $R_2$ represents hydrogen, is reacted with a halogenating agent, to produce an acyl halide, which is subsequently treated with an amine of general formula:

 (17)

in which $R_{13}$ and $R_{14}$ have the same meaning as in claim 1, and then, if necessary, the compound formed is deprotected, which gives a salt of the desired compound, which is treated with a suitable basic agent, to produce, in the free base form, the desired compounds, the free base thus formed possibly being, if necessary, treated with an organic or inorganic acid, to produce a pharmaceutically acceptable salt.

27. Process for the preparation of benzofuran or benzothiophene derivatives according to claim 1, in which Y represents the —CO— group, $R_1$ and $(Am_1)$ comprise no carboxylic or alkali metal carboxylate group, $R_{16}$ and/or $R_{17}$ and/or $R_{18}$ are different from the amino group or from a $C_1$–$C_4$ alkylsulfonamido group and R represents a group (e)

in which $R_{10}$ represents the hydroxyl group, wherein a compound of formula:

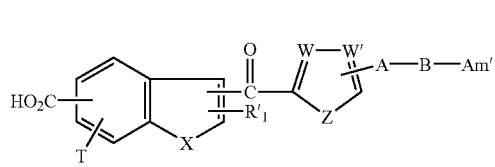

(10)

in which A, B, T, X, W, W' and Z have the same meaning as in claim 1, R'1 represents a $C_1$–$C_6$ alkyl, $C_3$–$C_6$ cycloalkyl, phenyl or benzyl group or a group (m) comprising no carboxylic or alkali metal carboxylate group and Am' represents a group ($Am_1$) as defined in claim 1, this group comprising no carboxylic or alkali metal carboxylate group, $R_{16}$ and/or $R_{17}$ and/or $R_{18}$ are different from an amino group or a $C_1$–$C_4$ alkylsulfonamido group, after protection of the amine functional group when Am' represents a group ($Am_1$) in which $R_2$ represents hydrogen, is reacted with a benzyloxyamine salt, in the presence of an acid scavenger and of benzotriazol-1-yloxytris(dimethylamino)phosphonium hexafluorophosphate, and then, if necessary, the compound formed is deprotected, which gives benzyloxyaminocarbonyl derivatives, which are hydrogenated in the presence of a suitable catalyst, to produce, in the free base form, the desired compounds, which are treated, if necessary, with a suitable organic or inorganic acid, to form a pharmaceutically acceptable salt.

28. Process according to one of claims 21 wherein the protection of the amine functional group is carried out by treatment by means of 9-fluorenylmethyl chloroformate and the deprotection is carried out by treatment with a secondary amine.

29. Process for the preparation of benzofuran or benzothiophene derivatives according to claim 1, in which Y represents the —CO— group, $R_1$ and ($Am_1$) comprise no carboxylic or alkali metal carboxylate group, $R_{16}$ and/or $R_{17}$ and/or $R_{18}$ are different from the amino group or from a $C_1$–$C_4$ alkylsulfonamido group and R represents a group (e) in which $R_{10}$ represents hydrogen, wherein a compound of formula:

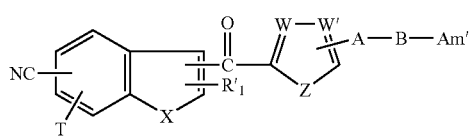

(18)

in which A, B, T, X, W, W' and Z have the same meaning as in claim 1, $R'_1$ represents a $C_1$–$C_6$ alkyl, $C_3$–$C_6$ cycloalkyl, phenyl or benzyl group or a group (m) comprising no carboxylic or alkali metal carboxylate group and Am' represents a group ($Am_1$) as defined in claim 1, this group comprising no carboxylic or alkali metal carboxylate group, $R_{16}$ and/or $R_{17}$ and/or $R_{18}$ are different from an amino group or a $C_1$–$C_4$ alkylsulfonamido group, is hydrolyzed in the presence of a strong acid, which gives the desired compounds in the free base form, which base can be treated, if necessary, with a suitable organic or inorganic acid, to form a pharmaceutically acceptable salt.

30. Process for the preparation of benzofuran or benzothiophene derivatives according to claim 1, in which Y represents the —CO— group, $R_1$ and ($Am_1$) comprise no carboxylic or alkali metal carboxylate group, $R_{16}$ and/or $R_{17}$ and/or $R_{18}$ are different from the amino group or from a $C_1$–$C_4$ alkylsulfonamido group and R represents the group (1), wherein a compound of formula:

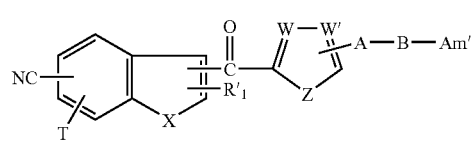

(18)

in which A, B, T, X, W, W' and Z have the same meaning as in claim 1, $R'_1$ represents a $C_1$–$C_6$ alkyl, $C_3$–$C_6$ cycloalkyl, phenyl or benzyl group or a group (m) comprising no carboxylic or alkali metal carboxylate group and Am' represents a group ($Am_1$) as defined in claim 1, this group comprising no carboxylic or alkali metal carboxylate group, $R_{16}$ and/or $R_{17}$ and/or $R_{18}$ are different from an amino group or a $C_1$–$C_4$ alkylsulfonamido group, is reacted with tributylazidotin, which gives the desired compounds in the free base form, which base can be treated, if necessary, with a suitable organic or inorganic acid, to form a pharmaceutically acceptable salt.

31. Process for the preparation of benzofuran or benzothiophene derivatives according to claim 1, in which Y represents the —CO— group, $R_1$ comprises no carboxylic or alkali metal carboxylate group and Am represents a group ($Am_1$) comprising no carboxylic or alkali metal carboxylate group and in which $R_{16}$ and/or $R_{17}$ and/or $R_{18}$ represent the amino group, wherein a nitro compound of formula:

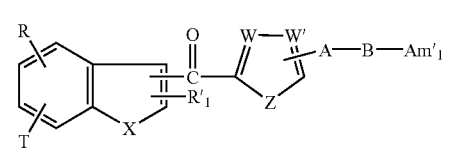

(19)

in which A, B, T, W, W', X and Z have the same meaning as in claim 1, R has the same meaning as in claim 1 but comprises no carboxylic or alkali metal carboxylate group, $R'_1$ represents a $C_1$–$C_6$ alkyl, $C_3$–$C_6$ cycloalkyl, phenyl or benzyl group or a group (m) comprising no carboxylic or alkali metal carboxylate group and $Am'_1$ represents either a group ($Am_1$) comprising no carboxylic or alkali metal carboxylate group and in which $R_{16}$ and/or $R_{17}$ and/or $R_{18}$ represent the nitro group, is hydrogenated in the presence of a suitable catalyst, which gives, in the free base form, the desired compounds, which can be reacted, if necessary, with a suitable organic or inorganic acid, to form a pharmaceutically acceptable salt.

32. Process for the preparation of benzofuran or benzothiophene derivatives according to claim 1, in which Y represents the —CO— group, $R_1$ comprises no carboxylic or alkali metal carboxylate group and Am represents a group ($Am_1$) comprising no carboxylic or alkali metal carboxylate group and in which $R_{16}$ and/or $R_{17}$ and/or $R_{18}$ represent a $C_1$–$C_4$ alkylsulfonamido group, wherein an amino compound of formula:

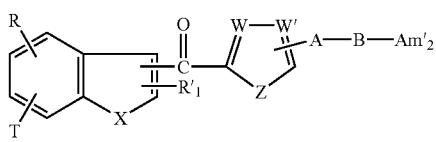
(20)

in which A, B, T, W, W', X and Z have the same meaning as in claim 1, R has the same meaning as in claim 1 but comprises no carboxylic or alkali metal carboxylate group, $R'_1$ represents a $C_1$–$C_6$ alkyl, $C_3$–$C_6$ cycloalkyl, phenyl or benzyl group or a group (m) comprising no carboxylic or alkali metal carboxylate group and $Am'_2$ represents either a group ($Am_1$) comprising no carboxylic or alkali metal carboxylate group and in which $R_{16}$ and/or $R_{17}$ and/or $R_{18}$ represent the amino group, is reacted with a halide of general formula:

(21)

or an anhydride of general formula:

(22)

in which $R'_{16}$ represents a linear or branched $C_1$–$C_4$ alkyl radical, optionally in the presence of an acid acceptor, which gives, in the free base form, the desired compounds, which can be reacted, if necessary, with a suitable organic or inorganic acid, to form a pharmaceutically acceptable salt.

33. Process for the preparation of benzofuran or benzothiophene derivatives according to claim 1, in which Y represents the —CO— group and one or two of the groups R, $R_1$, and ($Am_1$) comprise a —$CO_2R_5$ group in which $R_5$ represents hydrogen or an alkali metal atom, the other group(s) being different from a —$CO_2R_5$ group in which $R_5$ represents a $C_1$–$C_{10}$ alkyl or $C_3$–$C_6$ cycloalkyl radical, wherein a compound of formula:

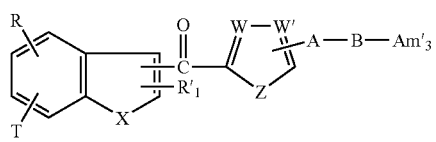
(23)

in which A, B, R, $R_1$, T, W, W', X and Z have the same meaning as in claim 1, $Am'_3$ represents a group ($Am_1$) as defined in claim 1, and R, $R_1$, and ($Am_1$) are such that one or two of them comprise(s) a —$CO_2R''_5$ group in which $R''_5$ represents a $C_1$–$C_{10}$ alkyl or $C_3$–$C_6$ cycloalkyl radical, the other group(s) being different from a —$CO_2R_5$ group in which $R_5$ represents a $C_1$–$C_{10}$ alkyl or $C_3$–$C_6$ cycloalkyl radical, is saponified in the presence of an alkali metal hydroxide, which gives, in the free base form, the desired compounds of formula (1) in which one or two of the groups R, $R_1$, and ($Am_1$) comprise(s) a —$CO_2R_5$ group in which $R_5$ represents an alkali metal atom, which compound can be treated, if necessary, with a strong acid, which gives, in the free base form, the desired compounds of formula (1) in which $R_5$ represents hydrogen, the free bases thus possibly being, if necessary, treated with a suitable organic or inorganic acid, to produce a pharmaceutically acceptable salt.

34. Process for the preparation of benzofuran or benzothiophene derivatives according to claim 1, in which Y represents the —CO— group and one of two of the groups R, $R_1$, and ($Am_1$) comprises a —$CO_2R_5$ group in which $R_5$ represents hydrogen or an alkali metal atom, and the other comprises a —$CO_2R_5$ group in which $R_5$ represents a $C_1$–$C_{10}$ alkyl or $C_3$–$C_6$ cycloalkyl group, the third group being different from a —$CO_2R_5$ group in which $R_5$ represents a $C_1$–$C_{10}$ alkyl or $C_3$–$C_6$ cycloalkyl group, wherein:

a compound of formula:

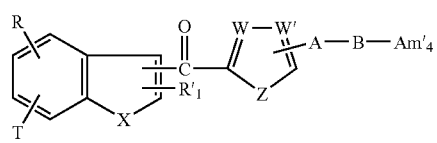
(24)

in which A, B, R, $R_1$, T, W, W', X and Z have the same meaning as in claim 1, $Am'_4$ represents a group ($Am_1$) as defined in claim 1, and R, $R_1$, and ($Am_1$) are such that one of them comprises a —$CO_2R''_5$ group in which $R''_5$ represents a $C_1$–$C_{10}$ alkyl or $C_3$–$C_6$ cycloalkyl group and another of them comprises a benzyloxycarbonyl group, the third group being different from a —$CO_2R_5$ group in which $R_5$ represents a $C_1$–$C_{10}$ alkyl or $C_3$–$C_6$ cycloalkyl group, is hydrogenated in the presence of a suitable catalyst;

a compound of formula:

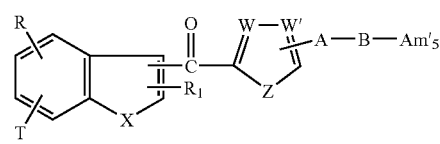
(25)

in which A, B, R, $R_1$, T, W, W', X and Z have the same meaning as in claim 1, $Am'_5$ represents a group ($Am_1$) as defined in claim 1, and R, $R_1$, and ($Am_1$) are such that one of them comprises a —$CO_2R''_5$ group in which $R''_5$ has the same meaning as above and another of them comprises a t-butoxycarbonyl group, the third group being different from a —$CO_2R_5$ group in which $R_5$ represents a $C_1$–$C_{10}$ alkyl or $C_3$–$C_6$ cycloalkyl group, is hydrolyzed in the presence of trifluoroacetic acid, which makes it possible to produce the desired compounds of formula (1) in which one of two of the groups R, $R_1$, and ($Am_1$) comprises a —$CO_2R_5$ group in which $R_5$ represents a $C_1$–$C_{10}$ alkyl or $C_3$–$C_6$ cycloalkyl group, and the other comprises a —$CO_2R_5$ group in which $R_5$ represents hydrogen, which compounds can be treated, if necessary, with a suitable basic agent, to produce, in the free base form, the desired compounds of formula (1) in which one of two of the groups R, $R_1$, and ($Am_1$) comprises a —$CO_2R_5$ group in which $R_5$ represents an alkali metal atom, the other a —$CO_2R_5$ group in which $R_5$ represents a $C_1$–$C_{10}$ alkyl or $C_3$–$C_6$ cycloalkyl group, which compounds can themselves be treated, if necessary, with a strong acid, to produce, in the free base form, the desired compounds of formula (1) in which one of two of the groups R, $R_1$, ($Am_1$) comprises a carboxylic group, the other a —$CO_2R_5$ group in which $R_5$ represents a $C_1$–$C_{10}$ alkyl or $C_3$–$C_6$ cycloalkyl group, the free bases thus formed possibly being, if necessary, treated with a suitable organic or inorganic acid, to produce a pharmaceutically acceptable salt.

35. Process for the preparation of benzofuran or benzothiophene derivatives according to claim 1, in which Y represents —CO—, R represents the cyano group and one of the groups $R_1$ or ($Am_1$) comprises a carboxylic group, wherein a compound of formula (1) according to claim 1, in which Y represents the —CO— group, R represents the cyano group, and in which A, B, $R_1$, T, W, W', X and Z have the same meaning as in claim 1, Am represents a group ($Am_1$) as defined in claim 1 and $R_1$ and ($Am_1$) are such that one of them comprises a —$CO_2R''_5$ group in which $R''_5$ represents a $C_1$–$C_{10}$ alkyl or $C_3$–$C_6$ cycloalkyl radical, is treated by means of tributyltin oxide, to produce the desired compounds in the free base form, which base can be reacted, if necessary, with an organic or inorganic acid, to form a pharmaceutically acceptable salt.

36. Process for the preparation of benzofuran or benzothiophene derivatives according to claim 1, in which Y represents the group

characterized in that a compound of formula (1) according to claim 1, in which Y represents the —CO— group and in which A, B, Am, R, $R_1$, T, W, W', X and Z have the same meaning as in claim 1, is reduced by means of an alkali metal borohydride, which gives the desired compounds in the free base form, which base can be reacted, if necessary, with an organic or inorganic acid, to produce a pharmaceutically acceptable salt.

37. Process for the preparation of benzofuran or benzothiophene derivatives according to claim 1, in which Y represents the group

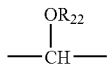

in which $R_{22}$ represents a $C_1$–$C_4$ alkyl radical wherein a compound of formula (1) according to claim 1, in which Y represents the —CHOH— group and in which A, B, Am, R, $R_1$, T, W, W', X and Z have the same meaning as in claim 1, is reacted with an alkali metal alkoxide and then with a halide of formula:

$R_{23}$-Hal in which Hal represents a halogen atom and $R_{23}$ represents a $C_1$–$C_4$ alkyl radical, which gives the desired compounds in the free base form, which base can be reacted, if necessary, with an organic or inorganic acid, to produce a pharmaceutically acceptable salt.

38. Process for the preparation of benzofuran or benzothiophene derivatives according to claim 1, in which Y represents a group

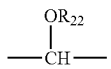

in which $R_{22}$ represents an acyl radical of formula —CO—$R_{23}$ in which $R_{23}$ represents a $C_1$–$C_4$ alkyl radical, wherein a compound of formula (1) according to claim 1, in which Y represents the —CHOH— group and in which A, B, Am, R, $R_1$, T, W, W', X and Z have the same meaning as in claim 1, is reacted with an acyl halide of formula:

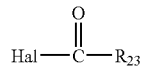

(27)

in which Hal represents a halogen atom and $R_{23}$ represents a $C_1$–$C_4$ alkyl radical, which gives the desired compounds in the free base form, which base can be reacted, if necessary, with an organic or inorganic acid, to form a pharmaceutically acceptable salt.

39. Process for the preparation of benzofuran or benzothiophene derivatives according to claim 1, in which Y represents the —$CH_2$— group, wherein a compound of formula (1) according to claim 1, in which Y represents the —CHOH— group and in which A, B, Am, R, $R_1$, T, W, W', X and Z have the same meaning as in claim 1, is reduced by means of an alkali metal borohydride, in the presence of trifluoroacetic acid, which gives the desired compounds in the free base form, which base can be reacted, if necessary, with a suitable organic or inorganic acid, to form a pharmaceutically acceptable salt.

40. A process according to claim 22 wherein the protection of the amine functional group is carried out by treatment by means of 9-fluorenylmethyl chloroformate and the deprotection is carried out by treatment with a secondary amine.

41. A process according to claim 23 wherein the protection of the amine functional group is carried out by treatment by means of 9-fluorenylmethyl chloroformate and the deprotection is carried out by treatment with a secondary amine.

42. A process according to claim 24 wherein the protection of the amine functional group is carried out by treatment by means of 9-fluorenylmethyl chloroformate and the deprotection is carried out by treatment with a secondary amine.

43. A process according to claim 25 wherein the protection of the amine functional group is carried out by treatment by means of 9-fluorenylmethyl chloroformate and the deprotection is carried out by treatment with a secondary amine.

44. A process according to claim 26 wherein the protection of the amine functional group is carried out by treatment by means of 9-fluorenylmethyl chloroformate and the deprotection is carried out by treatment with a secondary amine.

45. A process according to claim 27 wherein the protection of the amine functional group is carried out by treatment by means of 9-fluorenylmethyl chloroformate and the deprotection is carried out by treatment with a secondary amine.

46. A pharmaceutical or veterinary composition comprising as active principle, a therapeutically effective amount of at least one benzofuran or benzothiophene compound, or a pharmaceutically acceptable salt thereof, according to claim 1 in combination with a suitable excipient or pharmaceutical vehicle.

47. A pharmaceutical or veterinary composition according to claim 46 comprising from 50 to 500 mg of active principle.

48. A pharmaceutical or veterinary composition comprising as active principle, a therapeutically effective amount of at least one benzofuran or benzothiophene compound, or a pharmaceutically acceptable salt thereof, according to claim 2 in combination with a suitable excipient or pharmaceutical vehicle.

49. A pharmaceutical or veterinary composition comprising as active principle, a therapeutically effective amount of at least one benzofuran or benzothiophene compound, or a pharmaceutically acceptable salt thereof, according to claim 3 in combination with a suitable excipient or pharmaceutical vehicle.

50. A pharmaceutical or veterinary composition comprising as active principle, a therapeutically effective amount of at least one benzofuran or benzothiophene compound, or a pharmaceutically acceptable salt thereof, according to claim 4 in combination with a suitable excipient or pharmaceutical vehicle.

51. A pharmaceutical or veterinary composition comprising as active principle, a therapeutically effective amount of at least one beuzofuran or benzothiophene compound, or a pharmaceutically acceptable salt thereof, according to claim 5 in combination with a suitable excipient or pharmaceutical vehicle.

52. A pharmaceutical or veterinary composition comprising as active principle, a therapeutically effective amount of at least one beuzofuran or benzothiophene compound, or a pharmaceutically acceptable salt thereof, according to claim 6 in combination with a suitable excipient or pharmaceutical vehicle.

53. A pharmaceutical or veterinary composition comprising as active principle, a therapeutically effective amount of at least one beuzofuran or benzothiophene compound, or a pharmaceutically acceptable salt thereof, according to claim 7 in combination with a suitable excipient or pharmaceutical vehicle.

54. A pharmaceutical or veterinary composition comprising as active principle, a therapeutically effective amount of at least one beuzofuran or benzothiophene compound, or a pharmaceutically acceptable salt thereof, according to claim 8 in combination with a suitable excipient or pharmaceutical vehicle.

55. A pharmaceutical or veterinary composition comprising as active principle, a therapeutically effective amount of at least one benzofuran or benzothiophene compound, or a pharmaceutically acceptable salt thereof, according to claim 9 in combination with a suitable excipient or pharmaceutical vehicle.

56. A pharmaceutical or veterinary composition comprising as active principle, a therapeutically effective amount of at least one beuzofuran or benzothiophene compound, or a pharmaceutically acceptable salt thereof, according to claim 10 in combination with a suitable excipient or pharmaceutical vehicle.

57. A pharmaceutical or veterinary composition comprising as active principle, a therapeutically effective amount of at least one benzofuran or benzothiophene compound, or a pharmaceutically acceptable salt thereof, according to claim 11 in combination with a suitable excipient or pharmaceutical vehicle.

58. A pharmaceutical or veterinary composition comprising as active principle, a therapeutically effective amount of at least one benzofuran or benzothiophene compound, or a pharmaceutically acceptable salt thereof, according to claim 12 in combination with a suitable excipient or pharmaceutical vehicle.

59. A pharmaceutical or veterinary composition comprising as active principle, a therapeutically effective amount of at least one benzofuran or benzothiophene compound, or a pharmaceutically acceptable salt thereof, according to claim 13 in combination with a suitable excipient or pharmaceutical vehicle.

60. A pharmaceutical or veterinary composition comprising as active principle, a therapeutically effective amount of at least one benzofuran or benzothiophene compound, or a pharmaceutically acceptable salt thereof, according to claim 14 in combination with a suitable excipient or pharmaceutical vehicle.

61. A pharmaceutical or veterinary composition comprising as active principle, a therapeutically effective amount of at least one benzofuran or benzothiophene compound, or a pharmaceutically acceptable salt thereof, according to claim 15 in combination with a suitable excipient or pharmaceutical vehicle.

62. A method for the treatment of arrhythmia or hypertension which comprises administering to a patient in need of such treatment an effective amount of a compound according to claim 1.

63. A method for the treatment of arrhythmia or hypertension which comprises administering to a patient in need of such treatment an effective amount of a compound according to claim 2.

64. A method for the treatment of arrhythima or hypertension which comprises administering to a patient in need of such treatment an effective amount of a compound according to claim 3.

65. A method for the treatment of arrhythmia or hypertension which comprises administering to a patient in need of such treatment an effective amount of a compound according to claim 4.

66. A method for the treatment of arrhythmia or hypertension which comprises administering to a patient in need of such treatment an effective amount of a compound according to claim 5.

67. A method for the treatment of arrhythmia or hypertension which comprises administering to a patient in need of such treatment an effective amount of a compound according to claim 6.

68. A method for the treatment arrhythima or hypertension which comprises administering to a patient in need of such treatment an effective amount of a compound according to claim 7.

69. A method for the treatment arrhythmia or hypertension which comprises administering to a patient in need of such treatment an effective amount of a compound according to claim 8.

70. A method for the treatment arrhythmia or hypertension which comprises administering to a patient in need of such treatment an effective amount of a compound according to claim 9.

71. A method for the treatment of such arrhythmia or hypertension comprises administering to a patient in need of such treatment an effective amount of a compound according to claim 10.

72. A method for the treatment of arrhythmia or hypertension which comprises administering to a patient in need of such treatment an effective amount of a compound according to claim 11.

73. A method for the treatment of arrhythmia or hypertension which comprises administering to a patient in need of such treatment an effective amount of a compound according to claim 12.

74. A method for the treatment of arrhythmia or hypertension which comprises administering to a patient in need of such treatment an effective amount of a compound according to claim 13.

75. A method for the treatment of arrhythmia or hypertension which comprises administering to a patient in need of such treatment an effective amount of a compound according to claim 14.

76. A method for the treatment of arrhythmia or hypertension which comprises administering to a patient in need of such treatment an effective amount of a compound according to claim 15.

* * * * *